United States Patent
Dennis et al.

(10) Patent No.: US 9,266,955 B2
(45) Date of Patent: Feb. 23, 2016

(54) ANTI-FGFR4 ANTIBODIES AND METHODS OF USE

(71) Applicant: Genentech, Inc., South San Francisco, CA (US)

(72) Inventors: Mark Dennis, San Carlos, CA (US); Luc Desnoyers, San Francisco, CA (US); Dorothy French, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/046,659

(22) Filed: Oct. 4, 2013

(65) Prior Publication Data

US 2014/0037624 A1 Feb. 6, 2014

Related U.S. Application Data

(63) Continuation of application No. PCT/US2012/032491, filed on Apr. 6, 2012.

(60) Provisional application No. 61/473,106, filed on Apr. 7, 2011.

(51) Int. Cl.
*A61K 39/395* (2006.01)
*C07K 16/00* (2006.01)
*C07K 16/28* (2006.01)
*A61K 45/06* (2006.01)
*A61K 39/00* (2006.01)

(52) U.S. Cl.
CPC ......... *C07K 16/2863* (2013.01); *A61K 39/3955* (2013.01); *A61K 45/06* (2013.01); *A61K 2039/505* (2013.01); *C07K 2317/24* (2013.01); *C07K 2317/33* (2013.01); *C07K 2317/55* (2013.01); *C07K 2317/565* (2013.01); *C07K 2317/567* (2013.01); *C07K 2317/734* (2013.01); *C07K 2317/76* (2013.01); *C07K 2317/92* (2013.01); *C07K 2317/94* (2013.01)

(58) Field of Classification Search
None
See application file for complete search history.

(56) References Cited

FOREIGN PATENT DOCUMENTS

| EP | 1 918 376 A1 | 5/2008 |
|---|---|---|
| WO | 2005/066211 A2 | 7/2005 |
| WO | 2008/052796 A1 | 5/2008 |
| WO | 2010/004204 A2 | 1/2010 |
| WO | 2010/026291 A1 | 3/2011 |

OTHER PUBLICATIONS

Paul, W.E. Fundamental Immunology, 3rd Edition, 1993, pp. 292-295.*
MacCallum R.M. et al, Antibody-antigen interactions: Contact analysis and binding site topography. J. Mol. Biol., 1998, vol. 262, p. 732-745.*
Casset F, et al. A peptide mimetic of an anti-CD4 monoclonal antibody by rational design. Biochemical and Biophysical Research Communications, 2003, vol. 307, p. 198-205.*
Bendig, M.M. Humanization of rodent monoclonal antibodies by CDR grafting. Methods: A Companion to Methods in Enzymology, 1995; vol. 8, p. 83-93.*
Adams et al., "Humanization of a recombinant monoclonal antibody to produce a therapeutic HER dimerization inhibitor, pertuzumab" Cancer Immunother. 55(6):717-27 ( 2006).
Agus et al., "Targeting ligand-activated ErbB2 signaling inhibits breast and prostate tumor growth" Cancer Cell 2(2):127-137 (Aug. 2002).
Arenkov et al., "Protein microchips: use for immunoassay and enzymatic reactions" Anal Biochem. 278(2):123-31 ( 2000).
Bange et al., "Cancer progression and tumor cell motility are associated with the FGFR4 Arg(388) allele" Cancer Res. 62(3):840-7 ( 2002).
Bumbaca et al., "Highly specific off-target binding identified and eliminated during the humanization of an antibody against FGF receptor 4" MAbs 3(4):376-86 (Jul. 11, 2011).
Capellen et al., "Frequent activating mutations of FGFR3 in human bladder and cervix carcinomas" Nat. Genet. 23:18-20 (Sep. 1999).
Chen et al., "Generation and characterization of a panel of monoclonal antibodies specific for human fibroblast growth factor receptor 4 (FGFR4)" Hybridoma 24(3):152-9 (Jun. 2005).
Chesi et al., "Activated fibroblast growth factor receptor 3 is an oncogene that contributes to tumor progression in multiple myeloma" Blood 97(3):729-736 ( 2001).
Chesi et al., "Frequent translocation t(4;14)(p16.3;q32.3) in multiple myeloma is associated with increased expression and activating mutations of fibroblast growth factor receptor 3" Nat. Genet. 16:260-264 (Jul. 16, 1997).
Chizzonite et al., "IL-12: Monoclonal Antibodies Specific for the 40-kDa Subunit Block Receptor Binding and Biologic Activity on Activated Human Lymphoblasts" J Immunol 147(5):1548-1556 (Sep. 1991).
Circolo et al., "Genetic disruption of the murine complement C3 promoter region generates deficient mice with extrahepatic expression of C3 mRNA" Immunopharmacology 42:135-49 ( 1999).
Dennis MS, Biotechnolgy: Pharmaceutical Aspects. Current Trends in Monoclonal Antibody Development and Manufacturing "Chapter 2 CDR Repair: A Novel Approach to Antobody Humanization" Shire S, Gombotz W, Bechtold-Peters K, Andya J.,Co-published by the AAPS Press & Springer,:9-28 ( 2010).
Desnoyers et al., "Targeting FGF19 inhibits tumor growth in colon cancer xenograft and FGF19 transgenic hepatocellular carcinoma models" Oncogene 27(1):85-97 ( 2008).
Eswarakumar et al., "Cellular signaling by fibroblast growth factor receptors" Cytokine Growth Factor Rev. 16(2):139-49 (Apr. 2005).
Feyen et al., "Off-target activity of TNF-alpha inhibitors characterized by protein biochips" Anal Bioanal Chem. 391(5):1713-20 ( 2008).
Fodor et al., "Light-directed, spatially addressable parallel chemical synthesis" Science 251(4995):767-73 ( 1991).
Forster et al., "N12 Validation of tissue cross reactivity (TCR) studies: Tissue cross reactivity of anti-human CD209 in cynnomolgus tissues" Toxicology Letters 189S:S100 ( 2009).

(Continued)

*Primary Examiner* — Michael Pak
(74) *Attorney, Agent, or Firm* — Morrison & Foerster LLP

(57) ABSTRACT

The invention provides anti-FGFR4 antibodies and methods of using the same.

8 Claims, 22 Drawing Sheets

(56) References Cited

OTHER PUBLICATIONS

French et al., "Targeting FGFR4 Inhibits Hepatocellular Carcinoma in Preclinical Mouse Models" PLoS ONE 7(5):e36713 ( 2012).
Gallop et al., "Applications of Combinatorial Technologies to Drug Discovery Background and peptide combinatorial libraries" J Med Chem 37(9):1233-1251 (Apr. 29, 1994).
Ge et al., "UPA, a universal protein array system for quantitative detection of protein-protein, protein-DNA, protein-RNA and protein-ligand interactions" Nucleic Acids Res. 28(2):e3 ( 2000).
Gowardhan et al., "Evaluation of the fibloblast growth factor system as a potential target for therapy in human prostate cancer" Brit J Cancer 92:320-327 ( 2005).
Ho et al., "Fibroblast growth factor receptor 4 regulates proliferation, anti-apoptosis and alpha-fetoprotein secretion during hepatocellular carcinoma progression and represents a potential target for therapeutic intervention" J Hepatol. 50(1):118-27 ( 2009).
Holt et al., "Definition of a novel growth factor-dependent signal cascade for the suppression of bile acid biosynthesis" Genes Dev. 17(13):1581-91 ( 2003).
Ibrahimi et al., "Analysis of mutations in fibroblast growth factor (FGF) and a pathogenic mutation in FGF receptor (FGFR) provides direct evidence for the symmetric two-end model for FGFR dimerization" Mol Cell Biol. 25(2):671-84 ( 2005).
Jaakkola et al., "Amplification of fgfr4 ggene in human breast gynecological cancers" Int J Cancer 54(3):378-382 (May 28, 1993).
James et al., "Antibody multispecificity mediated by conformational diversity" Science 299:1362-1367 (Feb. 2003).
James et al., "The specificity of cross-reactivity: promiscuous antibody binding involves specific hydrogen bonds rather than nonspecific hydrophobic stickiness" Protein Sci, 12:2183-93 ( 2003).
Jang et al., "Mutations in fibroblast growth factor receptor 2 and fibroblast growth factor receptor 3 genes associated with human gastric and colorectal cancers" Cancer Res 61(9):3541-3 (May 2001).
Jeffers et al., "Fibroblast growth factors in cancer: therapeutic possibilities" Expert Opin Ther Targets 6(4):469-482 (Aug. 2002).
Jin et al., "Cullin3-based polyubiquitination and p62-dependent aggregation of caspase-8 mediate extrinsic apoptosis signaling" Cell 137(4):721-35 ( 2009).
Kallioniemi et al., "Tissue microarray technology for high-throughput molecular profiling of cancer" Hum Mol Genet. 10(7):657-62 ( 2001).
Kan et al., "Specificity for fibroblast growth factors determined by heparan sulfate in a binary complex with the receptor kinase" J Biol Chem 274(22):15947-15952 (May 28, 1999).
Kijanka et al., "Rapid characterization of binding specificity and cross-reactivity of antibodies using recombinant human protein arrays" J Immunol Methods 340(2):132-7. ( 2009).
Kim et al., "Antibody engineering for the development of therapeutic antibodies" Mol Cells. 20(1):17-29 ( 2005).
Kramer et al., "Molecular basis for the binding promiscuity of an anti-p24 (HIV-1) monoclonal antibody" Cell 91:799-809 ( 1997).
Krishnan et al., "Role of antibody paratope conformational flexibility in the manifestation of molecular mimicry" Biophys J. 94(4):1367-76 ( 2008).
Kurosu et al., "Tissue-specific expression of betaKlotho and fibroblast growth factor (FGF) receptor isoforms determines metabolic activity of FGF19 and FGF21." J Biol Chem 282(37):26687-95 (Sep. 2007).
Lee et al., "High-affinity human antibodies from phage-displayed synthetic Fab libraries with a single framework scaffold" J Mol Biol 340(5):1073-1093 (Jul. 23, 2004).
Lin et al., "Liver-specific activities of FGF19 require Klotho beta" J Biol Chem. 282(37):27277-84 ( 2007).
Lueking et al., "Determination and validation of off-target activities of anti-CD44 variant 6 antibodies using protein biochips and tissue microarrays" Biotechniques 45(4):Pi-v ( 2008).
Lutz et al., "lement amplification revisited" Mol Immunol. 43:2-12 ( 2006).
Lynch et al. Therapeutic Antibodies: Handbook of Experimental Pharmacology "Preclinical safety evaluation of monoclonal antibodies" Chernajovsky Y, Nissim A,Berlin:Springer-Verlag,:19-44 ( 2008).

MacCallum et al., "Antibody-antigen interactions: contact analysis and binding site topography" J Mol Biol. 262(5):732-45 ( 1996).
Manderson et al., "Continual low-level activation of the classical complement pathway" J Exp Med. 194(6):747-56. ( 2001).
Mohammadi et al., "Structural basis for fibroblast growth factor receptor activation" Cytokine & Growth Factor Reviews 16:107-137 ( 2005).
Nicholes et al., "A mouse model of hepatocellular carcinoma: ectopic expression of fibroblast growth factor 19 in skeletal muscle of transgenic mice" Am J Pathol. 160(6):2295-307 ( 2002).
Notkins, "Polyreactivity of antibody molecules" Trends Immunol 25(4):174-9 (Apr. 2004).
Ornitz et al., "Fibroblast growth factors" Genome Biol (REVIEWS3005), 2(3):1-12 ( 2001).
Ornitz et al., "Heparin is required for cell-free binding of basic fibroblast growth factor to a soluble receptor and for mitogenesis in whole cells" Mol Cell Biol. 12(1):240-7 ( 1992).
Osmers et al., "Complement in BuB/BnJ mice revisited: serum C3 levels and complement opsonic activity are not elevated" Mol Immunol. 43(10):1722-5 ( 2006).
Otte et al., "Molecular basis for the binding polyspecificity of an anti-cholera toxin peptide 3 monoclonal antibody" J Mol Recognit. 19(1):49-59 ( 2006).
Pai et al., "Inhibition of fibroblast growth factor 19 reduces tumor growth by modulating β-catenin signaling" Cancer Res. 68(13):5086-5095 (Jul. 1, 2008).
PCT IPER for PCT/US2012/032491.
PCT ISR for PCT/US2012/032491.
Plotnikov et al., "Structural basis for FGF receptor dimerization and activation" Cell 98:641-650 (Sep. 3, 1999).
Powers et al., "Fibroblast growth factors, their receptors and signaling" Endocr Relat Cancer. 7(3):165-97 (Sep. 2000).
Rosenwald et al., "Test of a statistical model for molecular recognition in biological repertoires" J Theor Biol. 21(3):327-36 ( 2002).
Sahu et al., "Covalent attachment of human complement C3 to IgG. Identification of the amino acid residue involved in ester linkage formation" J Biol Chem. 269(46):28997-9002 ( 1994).
Sahu et al., "Structure and biology of complement protein C3, a connecting link between innate and acquired immunity" Immunol Rev. 180:35-48 ( 2001).
Shariff et al., "Hepatocellular carcinoma: current trends in worldwide epidemiology, risk factors, diagnosis and therapeutics" Expert Rev Gastroenterol Hepatol. 3(4):353-67 ( 2009).
Thielges et al., "Exploring the energy landscape of antibody-antigen complexes: protein dynamics, flexibility, and molecular recognition" Biochemistry-US 47(27):7237-47 ( 2008).
Thorpe et al., "Molecular evolution of affinity and flexibility in the immune system" P Natl Acad Sci USA 104(21):8821-6 (May 2007).
Thurman et al., "The central role of the alternative complement pathway in human disease" J Immunol. 176(3):1305-10 ( 2006).
Tomlinson et al., "Transgenic Mice Expressing Human Fibroblast Growth Factor-19 Display Increased Metabolic Rate and Decreased Adiposity" Endocrinology 143(5):1741-47 ( 2002).
Vidarte, "Serine 132 is the C3 covalent attachment point on the CH1 domain of human IgG1" J Biol Chem. 276(41):38217-23 ( 2001).
Winer et al., "Development and validation of real-time quantitative reverse transcriptase-polymerase chain reaction for monitoring gene expression in cardiac myocytes in vitro" Anal Biochem 270(1):41-9 (May 1999).
Wu et al., "Co-receptor requirements for fibroblast growth factor-19 signaling" J Biol Chem 282(40):29069-72 (Oct. 2007).
Wu et al., "Development of motavizumab, an ultra-potent antibody for the prevention of respiratory syncytial virus infection in the upper and lower respiratory tract" J Mol Biol. 368(3):652-65 ( 2007).
Xiao et al., "FGFR1 is fused with a novel zinc-finger gene, ZNF198, in the t(8;13) leukaemia/lymphoma syndrome" Nat Genet. 18(1):84-7 ( 1998).
Yin et al., "Structural plasticity and the evolution of antibody affinity and specificity" J Mol Biol. 330(4):651-6 ( 2003).
Yu et al., "Elevated cholesterol metabolism and bile acid synthesis in mice lacking membrane tyrosine kinase receptor FGFR4" J Biol Chem. 275(20):15482-9 ( 2000).

* cited by examiner

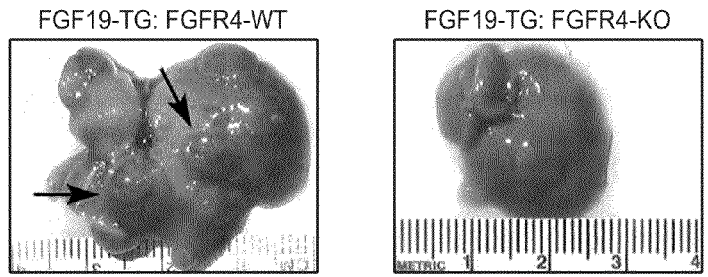
FIG. 1A
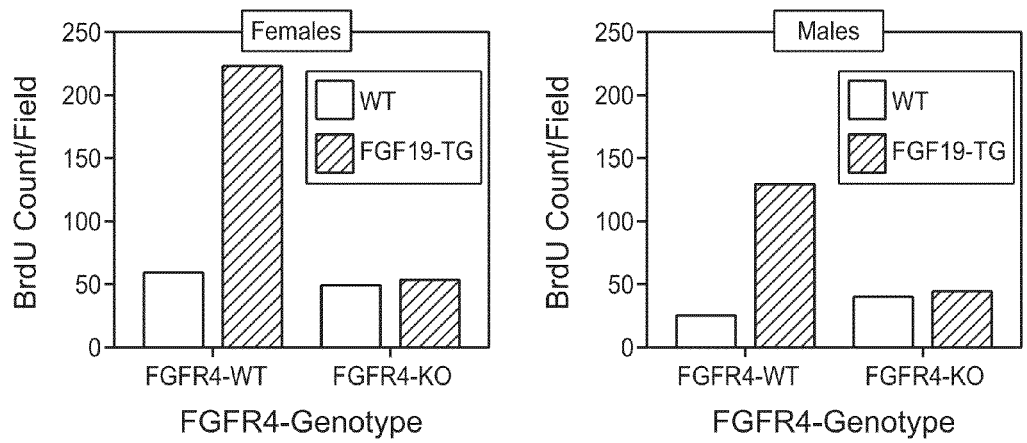
FIG. 1B
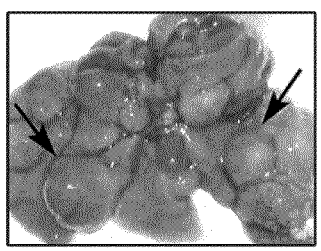
FIG. 1C
| Age (Month) | Sex | Gross Evidence of Tumor | Histological Evidence of Tumor |
|---|---|---|---|
| 4 | F | 9/10 | 10/10 |
|   | M | 9/10 | 10/10 |
| 5 | F | 10/10 | 10/10 |
|   | M | 9/10 | 10/10 |
| 6 | F | 10/10 | 10/10 |
|   | M | 10/10 | 10/10 |
| 7 | F | 10/10 | 10/10 |
|   | M | 6/6 | 6/6 |
FIG. 1D

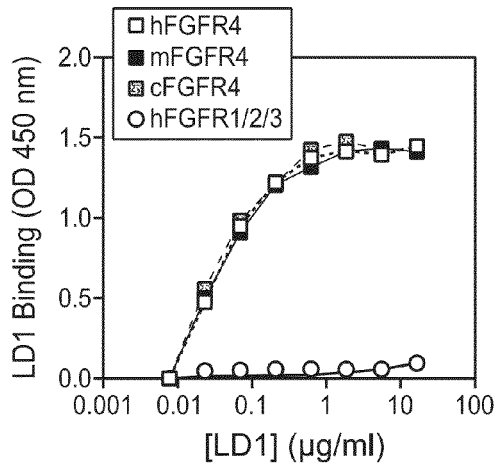
FIG. 2A
FIG. 2B
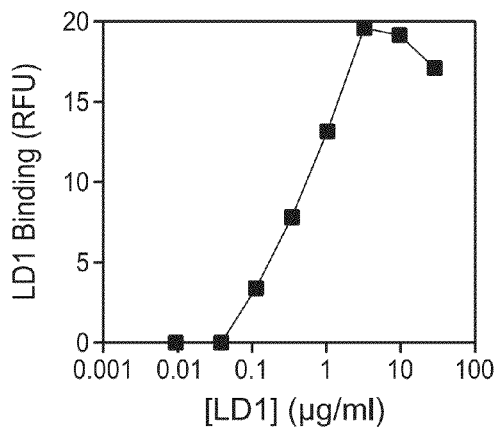
FIG. 2C
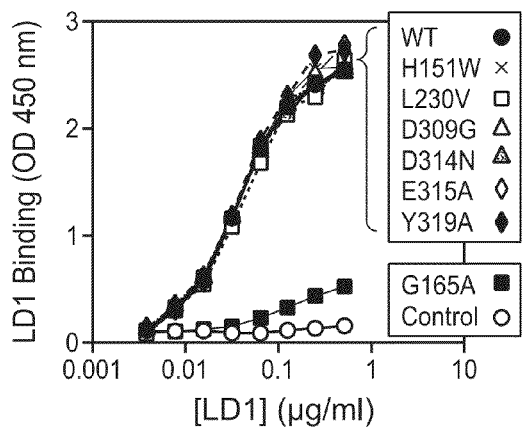
FIG. 2D

FIG. 10A

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 | 41 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| VH3  | E | V | Q | L | V | E | S | G | G | G | L | V | Q | P | G | G | S | L | R | L | S | C | A | A | S |   |   |   |   |   |   |   |   |   |   |   |   |   |   |   |   |   |   |
| LD1  | E | V | Q | L | L | Q | Q | P | G | G | A | V | L | R | P | G | T | S | L | K | L | S | C | K | A | S | G | Y | T | F | T | N | H | W | M | N |   | W | V | K | Q | R | P |
| hLD1.vB | E | V | Q | L | V | Q | S | G | G | G | L | V | Q | P | G | G | S | L | R | L | S | C | A | A | S | G | Y | T | F | T | N | H | W | M | N |   | W | V | R | Q | A | P |
| hLD1.v22 | E | V | Q | L | V | E | S | G | G | G | L | V | Q | P | G | G | S | L | R | L | S | C | A | A | S | G | Y | T | F | T | N | H | W | M | N |   | W | V | R | Q | A | P |

Kabat - CDR H1 (35–35B); Chothia - CDR H1 (26–32); Contact - CDR H1 (30–35B)

| Kabat# | 42 | 43 | 44 | 45 | 46 | 47 | 48 | 49 | 50 | 51 | 52 | a | b | c | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| VH3  | G | K | G | L | E | W | V |   |   |   |   |   |   |   |   |   |   |   |   |   |   |   |   |   |   |   |   | R | F | T | I | S | A | D | T | S | K | N | T | A | Y | L |
| LD1  | G | Q | G | L | E | W | I | G | M | I | H | P |   |   | S | D | S | E | T | T | L | D | Q | K | F | K | D | K | A | T | L | T | V | D | K | S | S | T | A | Y | M |
| hLD1.vB | G | K | G | L | E | W | V | G | M | I | H | P |   |   | S | D | S | E | T | T | L | D | Q | K | F | K | D | R | F | T | I | S | A | D | T | S | K | N | T | A | Y | L |
| hLD1.v22 | G | K | G | L | E | W | V | G | M | I | L | P |   |   | V | D | S | E | T | T | L | E | Q | K | F | K | D | R | F | T | I | S | A | D | T | S | K | N | T | A | Y | L |

Kabat - CDR H2 (50–65); Chothia - CDR H2 (52–56); Contact - CDR H2 (47–58)

| Kabat# | 81 | 82 | A | B | C | 83 | 84 | 85 | 86 | 87 | 88 | 89 | 90 | 91 | 92 | 93 | 94 | 95 | 96 | 97 | 98 | 99 | 100 | A | B | C | D | E | F | G | 101 | 102 | 103 | 104 | 105 | 106 | 107 | 108 | 109 | 110 | 111 | 112 | 113 | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| VH3  | Q | M | N | S | L | R | A | E | D | T | A | V | Y | Y | C |   |   |   |   |   |   |   |     |   |   |   |   |   |   |   |     |     |     |     |     |     |     |     |     |     |     |     |     | (SEQ ID NO: |
| LD1  | Q | L | N | R | P | T | S | E | D | S | A | V | Y | Y | C | T | R | G | D | I | S | L |     |   |   |   |   |   |   |   | F   | D   | Y   | W   | G   | Q   | G   | T   | T   | L   | T   | V   | S   | S | 35 |
| hLD1.vB | Q | M | N | S | L | R | A | E | D | T | A | V | Y | Y | C | T | R | G | D | I | S | L |     |   |   |   |   |   |   |   | F   | D   | Y   | W   | G   | Q   | G   | T   | L   | V   | T   | V   | S   | S | 36 |
| hLD1.v22 | Q | M | N | S | L | R | A | E | D | T | A | V | Y | Y | C | T | R | G | D | I | S | L |     |   |   |   |   |   |   |   | F   | D   | Y   | W   | G   | Q   | G   | T   | L   | V   | T   | V   | S   | S | 37 |
|          |   |   |   |   |   |   |   |   |   |   |   |   |   |   |   |   |   |   |   |   |   |   |     |   |   |   |   |   |   |   |     |     |     |     |     |     |     |     |     |     |     |     |     | 7) |

Kabat - CDR H3 (95–102); Chothia - CDR H3 (95–102); Contact - CDR H3 (93–101)

FIG. 10B

MGPASGSQLLVLLLLASSPLALGIPMYSIITPNVLRLESEETIVLEAHDAQGDIPVTVTVQDFLKRQVLTSEKTVLT
GASGHLRSVSIKIPASKEFNSDKEGHKYVTVVANFGETVVEKAVMVSFQSGYLFIQTDKTIYTPGSTVLYRIF
TVDNNLLPVGKTVVILIETPDGIPVKRDILSSNNQHGILPLSWNIPELVNMGQWKIRAFYEHAPKQIFSAEFEV
KEYVLPSFEVRVEPTETFYIDDPNGLEVSIIAKFLYGKNVDGTAFVIFGVQDGDKKISLAHSLTRVVIEDGVG
DAVLTRKVLMEGVRPSNADALVGKSLYVSVTVILHSGSDMVEAERSGIPIVTSPYQIHFTKTPKFFKPAMPF
DLMVFVTNPDGSPASKVLVVTQGSNAKALTQDDGVAKLSINTPNSRQPLTITVRTKKDTLPESRQATKTME
AHPYSTMHNSNNYLHLSVSRMELKPGDNLNVNFHLRTDPGHEAKIRYYTYLVMNKGKLLKAGRQVREPGQ
DLVVLSLPITPEFIPSFRLVAYYTLIGASGQREVVADSVWVDVKDSCIGTLVVKGDPRDNHLAPGQQTTLRIE
GNQGARVGLVAVDKGVFVLNKKNKLTQSKIWDVVEKADIGCTPGSGKNYAGVFMDAGLAFKTSQGLQTE
QRADLECTKPAARRRSVQLMERRMDKAGQYTDKGLRKCCEDGMRDIPMRYSCQRRARLITQGENCIKA
FIDCCNHITKLREQHRRDHVLGLARSELEEDIIPEEDIISRSHFPQSWLWTIEELKEPEKNGISTKVMNIFLKD
SITTWEILAVSLSDKKGICVADPYEIRVMQDFFIDLRLPYSVVRNEQVEIRAVLFNYREQEELKVRVELLHNPA
FCSMATAKNRYFQTIKIPPKSSVAVPYVIVPLKIGQQEVEVKAAVFNHFISDGVKKTLKVVPEGMRINKTVAIH
TLDPEKLGQGGVQKVDVPAADLSDQVPDTDSETRIILQGSPVVQMAEDAVDGERLKHLIVTPAGCGEQNMI
GMTPTVIAVHYLDQTEQWEKFGIEKRQEALELIKKGYTQQLAFKQPSSAYAAFNNRPPSTWLTAYVVKVFS
LAANLIAIDSHVLCGAVKWLLILEKQKPDGVFQEDGPVIHQEMIGGFRNAKEADVSLTAFVLIALQEARDICEG
QVNSLPGSINKAGEYIEASYMNLQRPYTVAIAGYALALMNKLEEPYLGKFLNTAKDRNRWEEPDQQLYNVE
ATSYALLALLLLKDFDSVPPVVRMLNEQRYYGGGYGSTQATFMVFQALAQYQTDVPDHKDLNMDVSFHLP
SRSSATTFRLIWENGNLLRSEETKQNEAFSLTAKGKGRGTLSVVAVYHAKLKSKVTCKKFDLRVSIRPAPE
TAKKPEEAKNTMFLEICTKYLGDVDATMSILDISMMTGFAPDTKDLELLASGVDRYISKYEMNKAFSNKNTLII
YLEKISHTEEDCLTFKVHQYFNVGLIQPGSVKVYSYYNLEESCTRFYHPEKDDGMLSKLCHSEMCRCAEEN
CFMQQSQEKINLNVRLDKACEPGVDYVYKTELTNIKLLDDFDEYTMTIQQVIKSGSDEVQAGQQRKFISHIK
CRNALKLQKGKKYLMWGLSSDLWGEKPNTSYIIGKDTWVEHWPEAEECQDQKYQKQCEELGAFTESMVV
YGCPN (SEQ ID NO:38)

*FIG. 12D*

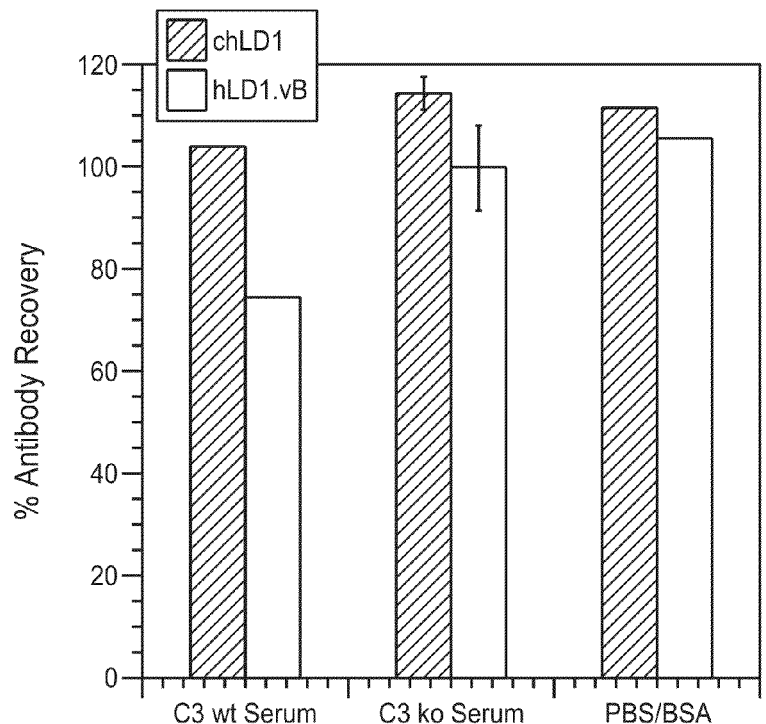

FIG. 17

MRLLLALLGVLLSVPGPPVLSLEASEEVELEPCLAPSLEQQEQELTVA
LGQPVRLCCGRAERGGHWYKEGSRLAPAGRVRGWRGRLEIASFLP
EDAGRYLCLARGSMIVLQNLTLITGDSLTSSNDDEDPKSHRDPSNRH
SYPQQAPYWTHPQRMEKKLHAVPAGNTVKFRCPAAGNPTPTIRWLK
DGQAFHGENRIGGIRLRHQHWSLVMESVVPSDRGTYTCLVENAVGSI
RYNYLLDVLERSPHRPILQAGLPANTTAVVGSDVELLCKVYSDAQPHI
QWLKHIVINGSSFGADGFPYVQVLKTADINSSEVEVLYLRNVSAEDAG
EYTCLAGNSIGLSYQSAWLTVLPEEDPTWTAAAPEARYTDIILYASGS
LALAVLLLLAGLYRGQALHGRHPRPPATVQKLSRFPLARQFSLESGS
SGKSSSSLVRGVRLSSSGPALLAGLVSLDLPLDPLWEFPRDRLVLGK
PLGEGCFGQVVRAEAFGMDPARPDQASTVAVKMLKDNASDKDLADL
VSEMEVMKLIGRHKNIINLLGVCTQEGPLYVIVECAAKGNLREFLRAR
RPPGPDLSPDGPRSSEGPLSFPVLVSCAYQVARGMQYLESRKCIHR
DLAARNVLVTEDNVMKIADFGLARGVHHIDYYKKTSNGRLPVKWMAP
EALFDRVYTHQSDVWSFGILLWEIFTLGGSPYPGIPVEELFSLLREGH
RMDRPPHCPPELYGLMRECWHAAPSQRPTFKQLVEALDKVLLAVSE
EYLDLRLTFGPYSPSGGDASSTCSSSDSVFSHDPLPLGSSSFPFGSG
VQTEFT (SEQ ID NO:39)

FIG. 18

ANTI-FGFR4 ANTIBODIES AND METHODS OF USE

CROSS REFERENCE TO RELATED APPLICATIONS

This application is continuation of International Patent Application No. PCT/US2012/032491, filed Apr. 6, 2012, which claims priority to U.S. Patent Application No. 61/473,106, filed Apr. 7, 2011, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Mar. 22, 2012, is named P4524R1WO.txt and is 37,020 bytes in size.

FIELD OF THE INVENTION

The present invention relates to anti-FGFR4 antibodies and methods of using the same.

BACKGROUND

Fibroblast growth factors (FGFs) comprise a family of 22 structurally related polypeptides with diverse biological activities; most of these signaling molecules function by binding to and activating their cognate receptors (FGFRs; designated FGFR1-4), a family of receptor tyrosine kinases (Eswarakumar et al., 2005; Ornitz and Itoh, 2001). These receptor-ligand interactions result in receptor dimerization and autophosphorylation, formation of complexes with membrane-associated and cytosolic accessory proteins, and initiation of multiple signaling cascades (Powers et al., 2000). The FGFR-FGF signaling system plays important roles in development and tissue repair by regulating cellular functions/processes such as growth, differentiation, migration, morphogenesis, and angiogenesis.

Alterations in FGFRs (i.e. overexpression, mutation, translocation, and truncation) are associated with a number of human cancers, including myeloma breast, stomach, colon, bladder, pancreatic, and hepatocellular carcinomas (Bange et al., 2002; Cappellen et al., 1999; Chesi et al., 2001; Chesi et al., 1997; Gowardhan et al., 2005; Jaakkola et al., 1993; Jang et al., 2001; Jang et al., 2000; Jeffers et al., 2002; Xiao et al., 1998). Hepatocellular carcinoma (HCC) is one of the leading global causes of cancer related deaths, resulting in over half a million fatalities per year (Shariff et al., 2009). While the role of FGFR4 in cancer remains to be fully elucidated, several findings suggest that this receptor may be an important player in HCC development and/or progression. FGFR4 is the predominant FGFR isoform present in human hepatocytes (Kan et al., 1999); we have also previously reported that liver tissue has the highest transcript levels of FGFR4 (Lin et al., 2007). In addition to FGFR4 being overexpressed in liver carcinomas (as well as several other types of human tumors), several missense genetic alterations have been observed in HCC patient samples; notably, a highly frequent G388R single nucleotide polymorphism in FGFR4 (associated with reduced survival for head and neck carcinoma, as well as a more aggressive phenotype for colon, soft tissue, prostate, and breast carcinomas was identified (Ho et al., 2009). Furthermore, it has been previously demonstrated that ectopic expression of FGF19 (i.e. FGFR4-specific ligand) in mice promotes hepatocyte proliferation, hepatocellular dysplasia, and neoplasia (Nicholes et al., 2002).

It is clear that there continues to be a need for agents that have clinical attributes that are optimal for development as therapeutic agents. The invention described herein meets this need and provides other benefits.

All references cited herein, including patent applications and publications, are incorporated by reference in their entirety.

SUMMARY

The invention provides anti-FGFR4 antibodies and methods of using the same.

In one aspect, the invention provides an isolated antibody that binds to FGFR4, wherein the anti-FGFR4 antibody binds human FGFR4 with an affinity of ≤1 nM. In some embodiment, the anti-FGFR4 antibody binds human, mouse and cynomolgus FGFR4 with an affinity of ≤1 nM. In some embodiments, the anti-FGFR4 antibody binds human FGFR4 with an affinity of ≤0.05 nM.

In some embodiments, the anti-FGFR4 antibody does not substantially bind a mouse C3 protein having the amino acid sequence shown in FIG. 12D.

In some embodiments, the anti-FGFR4 antibody binds to a denatured FGFR4. In some embodiments, the anti-FGFR4 antibody binds to denatured, reduced FGFR4. In some embodiments, binding of the anti-FGFR4 antibody to FGFR4 is detected using western blot.

In some embodiments, the anti-FGFR4 antibody does not significantly bind to human FGFR4 comprising a G165A mutation. In some embodiments, the anti-FGFR4 antibody binds a polypeptide having at least 70%, 80%, 90%, 95%, 98% sequence identity or similarity with the sequence comprising, consisting essentially of or consisting of amino acid numbers 150 to 170 of the mature human FGFR4 amino acid sequence. In some embodiments, the anti-FGFR4 antibody binds a polypeptide comprising, consisting essentially of or consisting of amino acid numbers 150 to 170 of the mature human FGFR4 amino acid sequence.

In some embodiments, the anti-FGFR4 is an antagonist of FGFR4 activity. In some embodiments, FGFR4 activity is FGF induced cell proliferation, FGF binding to FGFR4, FGF19-mediated inhibition of CYP7α7 expression in a cell exposed to FGF19, or FGF19-induced colony formation. In some embodiments, FGF1 and/or FGF19 binding to FGFR4 is inhibited. In some embodiments, the IC50 for inhibition of FGF1 binding to FGFR4 is about 0.10 nM and the IC50 for inhibition of FGF19 binding to FGFR4 is about 0.10 nM.

In some embodiments, the anti-FGFR4 antibody is a monoclonal antibody.

In some embodiments, the anti-FGFR4 antibody is a human, humanized, or chimeric antibody.

In some embodiments, the anti-FGFR4 antibody is an antibody fragment that binds FGFR4.

In some embodiments, the antibody comprises (a) HVR-H3 comprising the amino acid sequence of SEQ ID NO:3, (b) HVR-L3 comprising the amino acid sequence of SEQ ID NO:6, and (c) HVR-H2 comprising the amino acid sequence of SEQ ID NO:2.

In some embodiments, the antibody comprises (a) HVR-H1 comprising the amino acid sequence of SEQ ID NO:1 (b) HVR-H2 comprising the amino acid sequence of SEQ ID NO:2, and (c) HVR-H3 comprising the amino acid sequence of SEQ ID NO:3. In some embodiments, the antibody further comprises (a) HVR-L1 comprising the amino acid sequence of SEQ ID NO:4; (b) HVR-L2 comprising the amino acid sequence of SEQ ID NO:5; and (c) HVR-L3 comprising the amino acid sequence of SEQ ID NO:6.

In some embodiments, the antibody comprises (a) HVR-L1 comprising the amino acid sequence of SEQ ID NO:4; (b) HVR-L2 comprising the amino acid sequence of SEQ ID NO:5; and (c) HVR-L3 comprising the amino acid sequence of SEQ ID NO:6. In some embodiments, the antibody further comprises a light chain variable domain framework sequence of SEQ ID NO: 9, 10, 11 and/or 12.

In some embodiments, the antibody further comprises a heavy chain variable domain framework sequence of SEQ ID NO:13, 14, 15 and/or 16.

In some embodiments, the antibody comprises (a) a VH sequence having at least 95% sequence identity to the amino acid sequence of SEQ ID NO:7; (b) a VL sequence having at least 95% sequence identity to the amino acid sequence of SEQ ID NO:8; or (c) a VH sequence as in (a) and a VL sequence as in (b). In some embodiments, the antibody comprises a VH sequence of SEQ ID NO: 7. In some embodiments, the antibody comprises a VL sequence of SEQ ID NO: 8.

In some embodiments, the antibody comprises a VH sequence of SEQ ID NO:7 and a VL sequence of SEQ ID NO:8.

In some embodiments, the antibody is a full length IgG1 antibody.

The invention also provides isolated nucleic acids encoding any of the antibodies described herein.

The invention also provides host cells comprising any of the nucleic acids described herein.

The invention also provides methods of producing an antibody comprising culturing the host cell described herein so that the antibody is produced. In some embodiments, the method further comprises recovering the antibody from the host cell.

The invention also provides immunoconjugates comprising any of the antibodies described herein and a cytotoxic agent.

The invention also provides pharmaceutical formulations comprising any of the antibodies described herein and a pharmaceutically acceptable carrier. In some embodiments, the pharmaceutical formulation further comprises an additional therapeutic agent.

The invention also provides any of the antibodies described herein for use as a medicament.

In some embodiments, the antibodies are for use in treating cancer

In some embodiments, the antibodies are for use in inhibiting cell proliferation In some embodiments, the antibodies are for use in the manufacture of a medicament.

In some embodiments, the medicament is for treatment of cancer

In some embodiments, the medicament is for inhibiting cell proliferation.

The invention also provides methods of treating an individual having cancer comprising administering to the individual an effective amount of any of the antibodies described herein. In some embodiments, the methods further comprise administering an additional therapeutic agent to the individual.

The invention also provides methods of inhibiting cell proliferation in an individual comprising administering to the individual an effective amount of any of the antibodies described herein to inhibit cell proliferation.

In some embodiments, the cancer is cancer of the breast, lung, pancreas, brain, kidney, ovary, stomach, leukemia, uterine endometrium, colon, prostate, pituitary, mammary fibroadenoma, head and neck, soft tissue, neuroblastomas, melanoma, endometrium, testis, cholangiocarcinoma, gallbladder and/or liver.

In certain embodiments, the cancer displays FGFR4 expression (such as overexpression), amplification, or activation. In certain embodiments, the cancer displays FGFR4 amplification.

BRIEF DESCRIPTION OF THE FIGURES

FIGS. 1A-1F: FGFR4 is required for FGF19-mediated liver tumorigenesis. A, Multiple, large, raised tumors (arrows) protruding from the hepatic surface of a 10-month-old FGF19-TG:FGFR4-WT mouse (left panel). Liver from 10-month-old FGF19-TG:FGFR4-KO mouse (right panel). B, BrdU incorporation in female (left panel) and male (right panel) FGF19-TG or wild type mice bred with FGFR4-KO or FGFR4-WT mice. C, Multiple, large, raised tumors (arrows) on the surface of the liver of a 4-month-old FGF19-TG:FGFR4-WT mouse treated with DEN. D, Prevalence of liver tumors in male and female FGF19-TG mice treated with DEN as determined by gross and histological examinations. E, Liver weights from FGF19-TG or wild type female (left panel) and male (right panel) mice treated with DEN. The asterisk (*) indicates that the weight of the liver could not be measured from the 7-month time point for male FGF19-TG mice treated with DEN because none survived past 6 months of age. F, Liver weights of FGF19-TG or wild type female (left panel) and male (right panel) FGFR4-KO mice treated with DEN.

FIGS. 2A-2F: LD1 binds to FGFR4. A, LD1 binds to human (h), mouse (m), and cynomolgus (c) FGFR4 but does not bind to hFGFR1, hFGFR2, or hFGFR3. The binding of LD1 to immobilized FGFR-Fc chimeric proteins was determined by solid phase binding assay. B, Affinity of LD1 binding to mouse, cynomolgus, and human FGFR4 as determined by surface plasmon resonance. C, Binding of LD1 to hFGFR4 expressed at the cell surface of stably transfected HEK293 cells as measured by FACS (RFU=Relative Fluorescence Unit). D, The binding of LD1 to immobilized hFGFR4-Flag chimeric proteins bearing point mutations as measured by a solid phase binding assay. E, The binding of LD1 to hFGFR4-Flag chimeric proteins bearing point mutations as evaluated by Western blot. Mutated proteins were electrophoresed and sequentially immunoblotted using LD1, an anti-FGFR4 (8G11), and an anti-Flag antibody. F, Dimer model illustrating the position of G165 (black) on FGFR4 (black and white) bound to FGF19 (grey).

FIGS. 10A and 10B: Variable domain sequences of mouse and humanized variants of anti-FGFR4. The amino acid sequences of mouse LD1 and humanized variants hLD1.vB and hLD1.v22 are aligned with the (A) human kappa I (huKI) and (B) human VH subgroup III (huIII) variable domain frameworks used in trastuzumab. Differences are highlighted in dotted boxes and positions are numbered according to Kabat. Hypervariable regions that were grafted from mouse LD1 into the human variable Kappa I and subgroup III consensus frameworks were selected based on a combination of sequence, structural and contact CDR definitions (MacCallum R M et al. *J of Molec Biol* (1996); 262:732-45) and are boxed. Three vernier positions in the light chain were altered to restore affinity during humanization; these positions were not expected to be surface exposed.

FIGS. 12A-12D: Identification of an interaction between hLD1.vB and mouse C3d. (A) Detection of chLD1 (hatched bar) and hLD1.vB (white bar) following incubation for 48 h in PBS/BSA or NCR nude mouse, rat, human and cynomolgus monkey plasma. Percent recovery was determined using the FGFR4 ELISA. (B) Plasma binding analysis of $^{125}$I-chLD1 (solid line) and $^{125}$I-hLD1.vB (dashed line). The traces are off-set; a dot indicates the position of the 150 kDa peaks. The antibodies were incubated in mouse plasma for 0 and 48 h followed by analysis using size exclusion HPLC. For incubations in PBS/BSA, human plasma or cynomolgus monkey plasma see FIG. 15. All incubations gave rise to a peak at the expected 150 kDa corresponding to IgG. Higher molecular weight peaks were only observed in mouse plasma samples containing hLD1.vB. The initial time point revealed additional peaks at ca. 270 and ca. 550 kDa while at 48 h, only the 270 kDa peak was observed. The high molecular weight peaks were not observed when hLD1.vB/mouse plasma incubations were performed at pH 4, indicating that the presence of these high molecular weight peaks was pH dependent (FIG. 15). (C) Immunoprecipitation of mouse plasma. chLD1 and hLD1.vB were incubated in mouse plasma for 24 hours at 37° C. and analyzed by size-exclusion HPLC. Protein-G beads were then added to fractions followed by SDS-PAGE analysis. A band at ca. 37 kDa was detected in fractions corresponding to the 270 kDa peak present in the hLD1.vB/mouse plasma sample (lane 3), but not in samples from cynomolgus monkey or human plasma or PBS/BSA (FIG. 15). This band was not observed in mouse plasma alone (lane 4) or mouse plasma incubated with chLD1 (lane 2). The protein molecular weight marker was run in lane 1. (D) MS/MS sequence coverage of mouse C3 obtained from immunoprecipitation with hLD1.vB. The sequence for mouse C3 is shown (SEQ ID NO: 38) and the region encoding C3d is underlined. Identified peptides were as follows:

```
                                                            (SEQ ID NO: 17)
DVPAADLSDQVPDTDSETRIILQGSPVVQMAEDAVDGER (SEQ ID NO: 18)
RQEALELIKKGYTQQLAFK (SEQ ID NO: 19)
AAFNNRPPSTWLTAYVVK (SEQ ID NO: 20)
AANLIAIDSHVLCGAVK
```

-continued

```
                                                 (SEQ ID NO: 21)
QKPDGVFQEDGPVIHQEMIGGFR (SEQ ID NO: 22)
EADVSLTAFVLIALQEARDICEGQVNSLPGSINKAGEYIEASYMNLQRPYTVAIAGYALA

LMNK (SEQ ID NO: 23)
WEEPDQQLYNVEATSY (SEQ ID NO: 24)
YYGGGYGSTQATFMVFQALAQYQTDVPDHK (SEQ ID NO: 25)
GTLSVVAVYHAK (SEQ ID NO: 26)
DLELLASGVDR (SEQ ID NO: 27)
NTLIIYLEK.
```

Figure 13A:
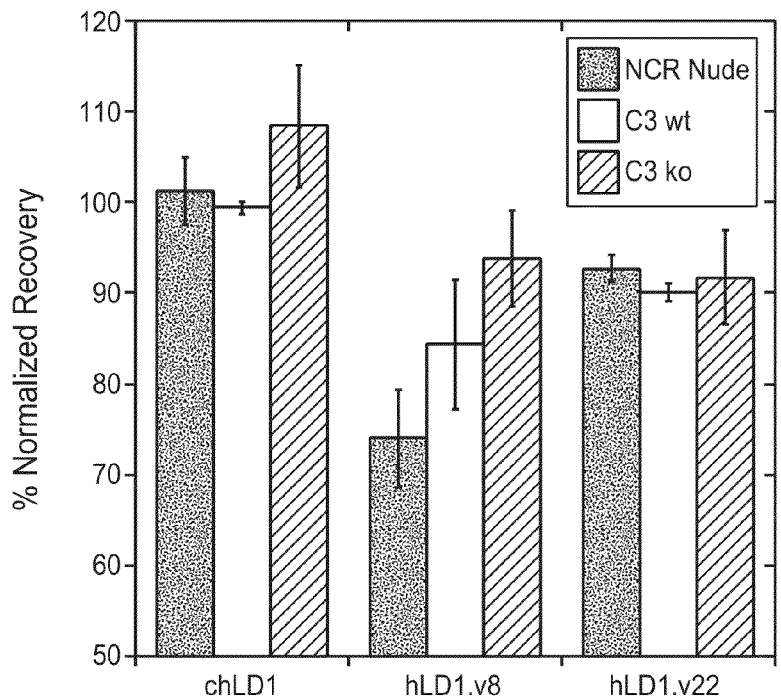
Figure 13B:
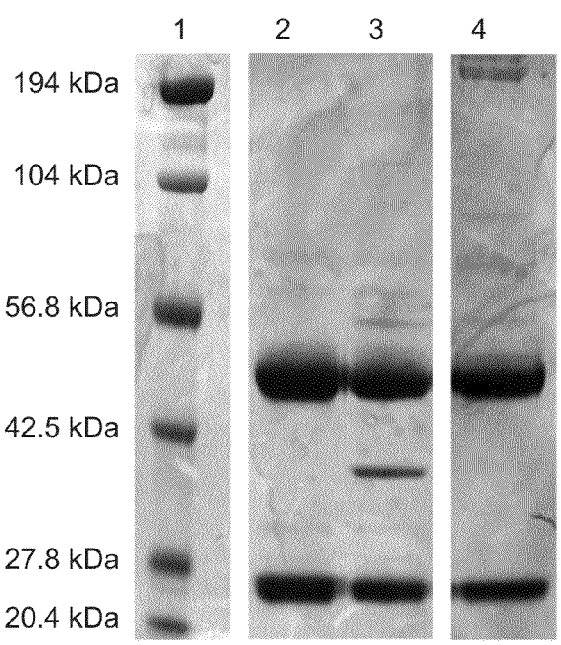

FIGS. 13A-13B: An affinity matured anti-FGFR4 variant lacked C3d binding. (A) Detection of FGFR4 binding of chLD1, hLD1.vB and hLD1.v22 incubated 16 hours in NCR nude, C3 wildtype (wt) and C3 ko mouse serum prior to assessment using the FGFR4 ELISA. Samples were normalized to identical samples incubated in PBS/0.5% BSA. (B) Lack of mouse C3d immunoprecipitation by hLD1.v22. Immunoprecipitation from NCR nude mouse plasma using chLD1 (lane 2), hLD1.vB (lane 3) and hLD1.v22 (lane 4) was analyzed by SDS-PAGE. The band at ~37 kDa was only detected in the hLD1.vB/mouse plasma sample. The protein molecular weight marker was run in lane 1.

Figure 14C:
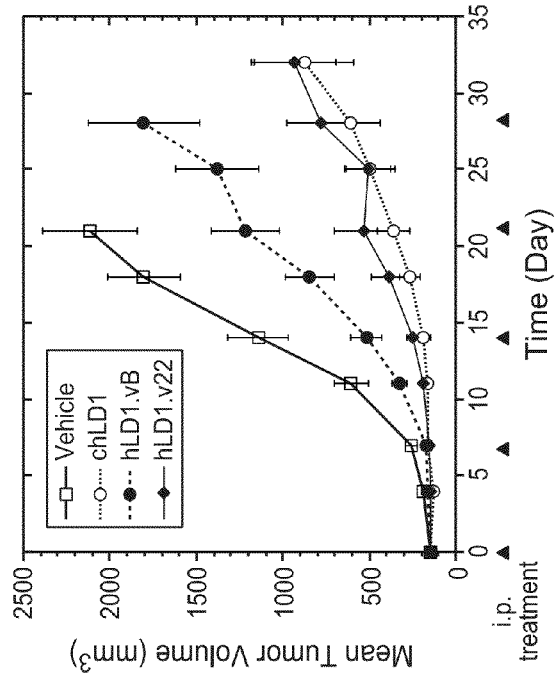
Figure 14A:
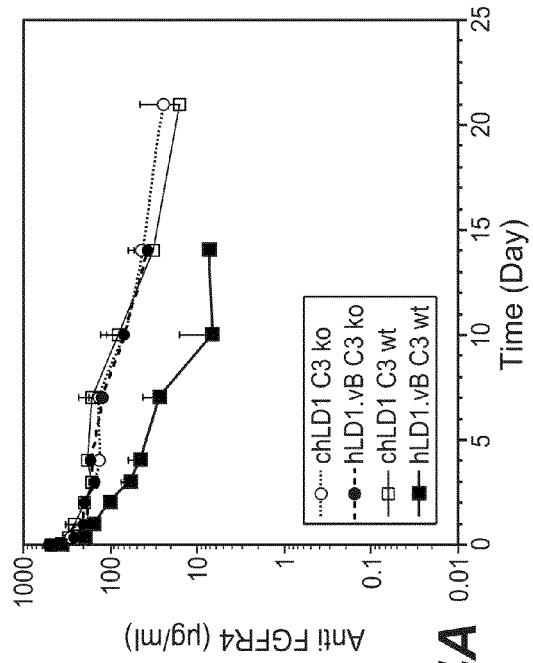
Figure 14B:
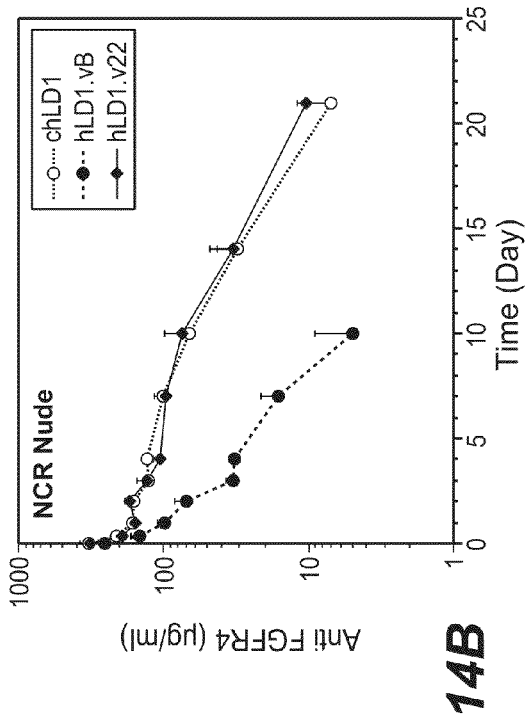

FIGS. 14A-14C: Loss of C3d binding restores Pharmacokinetics and Efficacy. (A) Pharmacokinetic analysis of chLD1 and hLD1.vB in C3 wt and C3 ko mice. Antibodies were dosed IV at 20 mg/kg; their concentration in blood was monitored using the FGFR4 ELISA. The clearance of hLD1.vB in C3 k mice is similar to that of chLD1 in both C3 ko and C3 wt mice. (B) Pharmacokinetic analysis of chLD1 hLD1.vB and hLD1.v22 in NCR nude mice. Antibodies were dosed IV at 20 mg/kg; their concentration in blood was monitored using the FGFR4 ELISA. The clearance of hLD1.v22 is similar to that of chLD1. (C) Comparison of chLD1 hLD1.vB and hLD1.v22 in an HUH7 human HCC xenograft model in CRL nu/nu mice. Antibodies were dosed at 30 mg/kg weekly (10 mice per group) and tumor volumes were monitored for 4 weeks. At day 21 chLD1 and hLD1.v22 (p value=7×10⁻⁷ and 3×10⁻⁵, respectively) were effective at reducing tumor growth relative to the PBS control (open square) while hLD1.vB was only marginally effective (p value=0.011).

Figure 15A:
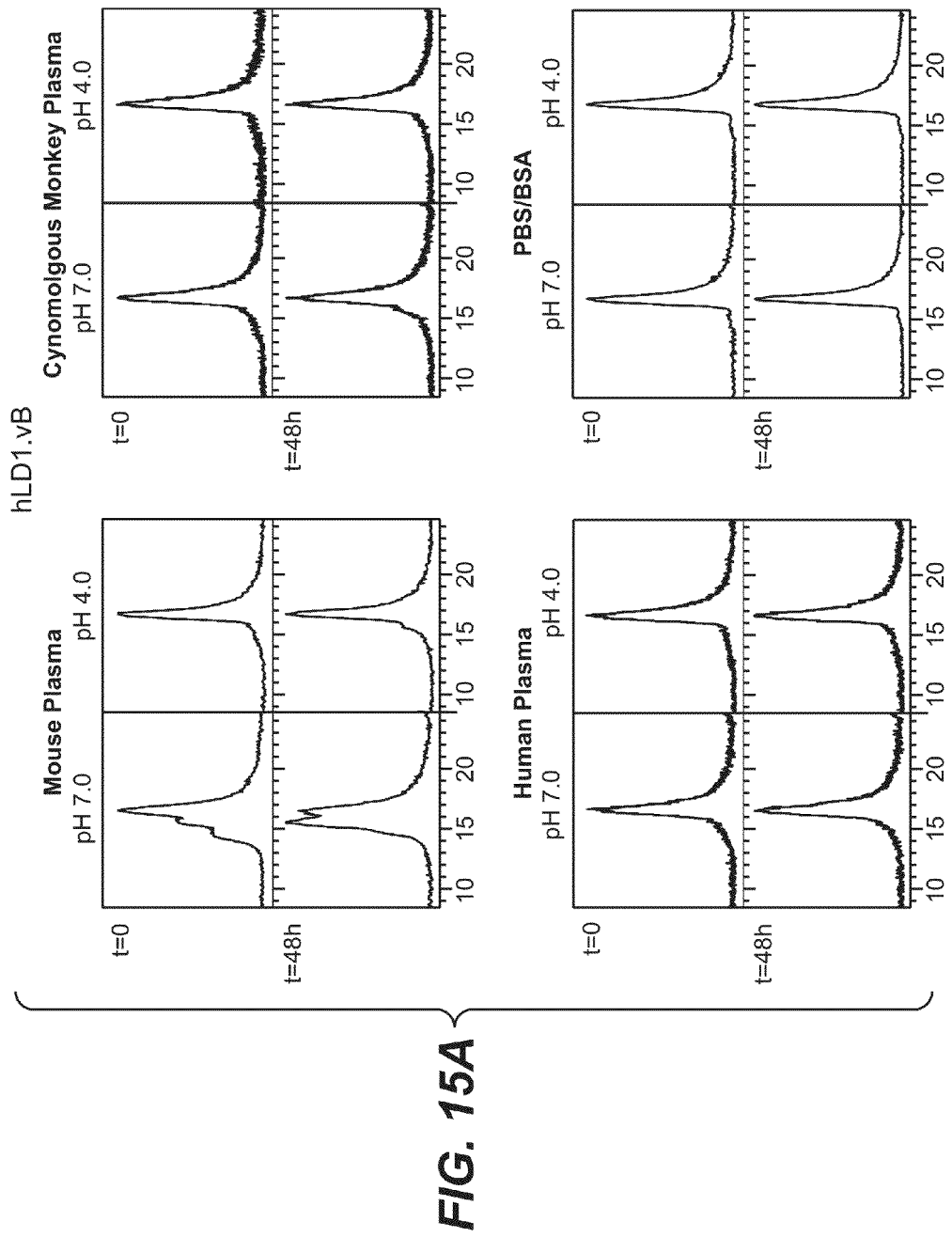
Figure 15B:
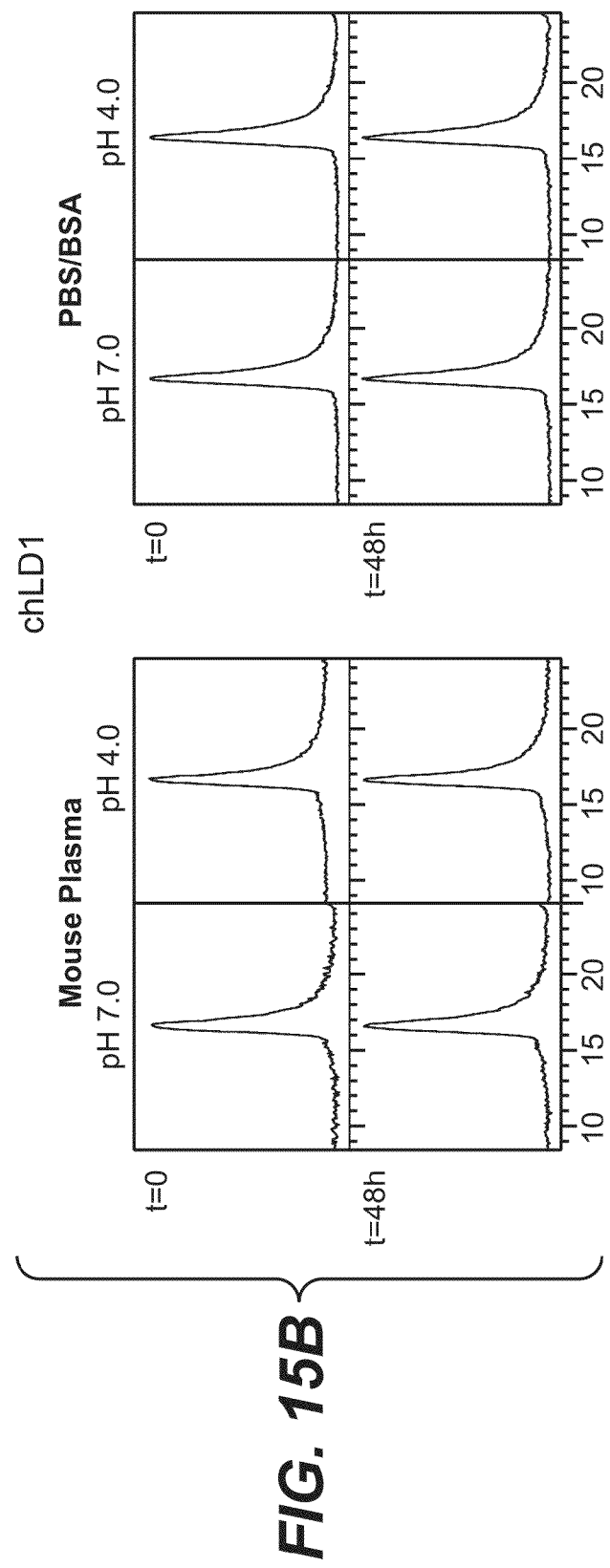
Figure 15C:
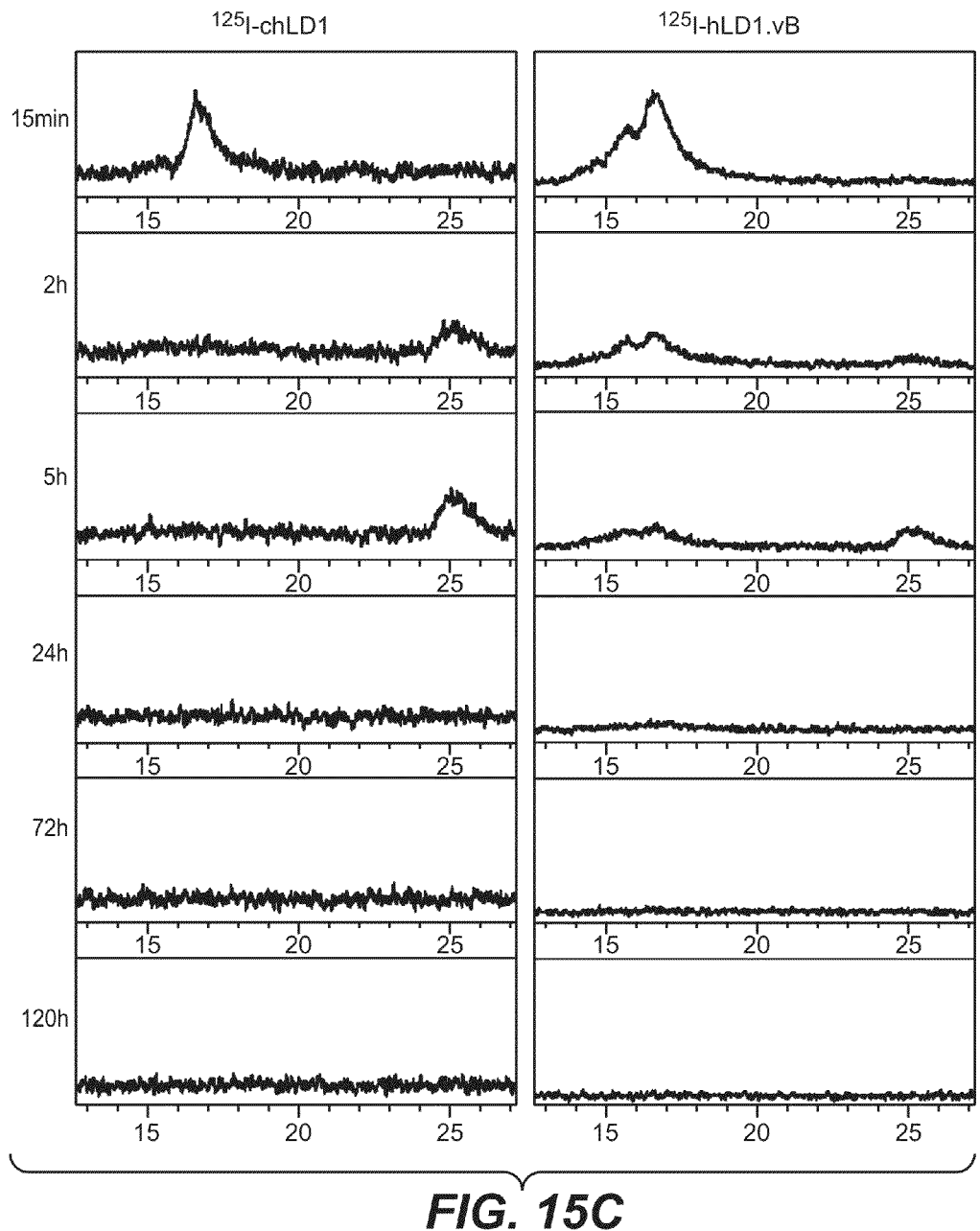

FIGS. 15A-15C: Size-exclusion HPLC analysis of radiolabeled chLD1 and hLD1.vB in plasma from in vitro (A-B) and in vivo study (C) samples. $^{125}$I-hLD1.vB (A) and $^{125}$I-chLD1 (B) were added to PBS/BSA or mouse, human and cynomolgus monkey plasma and analyzed by size-exclusion HPLC at 0 or 48 h. All traces revealed a peak at the expected 150 kDa (peak on the right) for IgG. Higher molecular weight peaks at ca. 270 (peak in the middle) and ca. 550 kDa (peak on the left) were observed only in the initial mouse plasma sample containing hLD1.vB; at 48 h only the additional 270 kDa peak was observed. These high molecular weight peaks were not observed with hLD1.vB in mouse plasma at pH 4.0 indicating that generation of the high molecular weight peaks was pH dependent. High molecular weight peaks were not detected in cynomolgus monkey or human plasma or in any plasma with chLD1 added; (C) In vivo mouse plasma samples. Mice were dosed with ~0.1 mg/kg of antibody with a specific activity of 12.52 µCi/µg for chLD1 and 9.99 µCi/ug for hLD1.vB. Serum samples were collected at 0.25, 2, 5, 24, 72 and 120 h. All traces revealed a peak at the expected 150 kDa (peak on the right) for IgG. Higher molecular weight peaks at ~270 (peak in the middle) and ~550 kDa (peak on the left) were observed only in the hLD1.vB serum samples. High molecular weight peaks were not observed with chLD1.

FIGS. 16A-16D: Immunoprecipitation and SDS-PAGE analysis. Antibodies were incubated in plasma for 24 h at 37° C., then fractionized by size-exclusion HPLC. Protein-G beads were added to size exclusion HPLC fractions containing high molecular weight peaks. The pull-down samples were analyzed by SDS-PAGE. (A) In vitro rat plasma; (B) In vitro cynomolgus monkey plasma; (C) In vitro human plasma. A ~37 kDa protein was detected in rat samples incubated with hLD1.vB, but not in the cynomolgus monkey and human samples (lane 4 of their respective gels). No band at ~37 kDa protein was observed in any of the blank plasma (lane 2 of each gel) or in the chLD1 samples (lane 3 of each gel). The protein molecular weight marker was run in lane 1. (D) In vivo mouse plasma. Mice were dosed with hLD1.vB or chLD1 as described in the "METHODS". Protein-G beads were then added to the collected serum samples from the 2 h post dose time point and analyzed by SDS-PAGE. A band at ~37 kDa was detected in the hLD1.vB (lane 3), but not the chLD1 serum sample (lane 2). The protein molecular weight marker was run in lane 1.

FIG. 17: ELISA detection of chLD1 and hLD1.vB added to C3 wt serum, C3 ko mouse serum, and PBS/BSA. The antibodies were incubated overnight in serum or PBS/BSA and then analyzed by ELISA. Relative to PBS/BSA, hLD1.vB was fully recovered in C3 ko mouse serum, but not C3 wt mouse serum. chLD1 was fully recovered from all matrices.

FIG. 18: shows an exemplary human FGFR4 amino acid sequence of GenBank Accession No. AAB25788.

DETAILED DESCRIPTION OF EMBODIMENTS OF THE INVENTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

An anti-angiogenic agent refers to a compound which blocks, or interferes with to some degree, the development of blood vessels. An anti-angiogenic agent may, for instance, be a small molecule or antibody that binds to a growth factor or growth factor receptor involved in promoting angiogenesis. In one embodiment, an anti-angiogenic agent is an antibody that binds to vascular endothelial growth factor (VEGF), such as bevacizumab (AVASTIN®).

The terms "anti-FGFR4 antibody" and "an antibody that binds to FGFR4" refer to an antibody that is capable of binding FGFR4 with sufficient affinity such that the antibody is useful as a diagnostic and/or therapeutic agent in targeting FGFR4. In one embodiment, the extent of binding of an anti-FGFR4 antibody to an unrelated, non-FGFR4 protein is less than about 10% of the binding of the antibody to FGFR4 as measured, e.g., by a radioimmunoassay (RIA). In certain embodiments, an antibody that binds to FGFR4 has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-FGFR4 antibody binds to an epitope of FGFR4 that is conserved among FGFR4 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "FGFR4," as used herein, refers to any native FGFR4 from any vertebrate source, including mammals such as primates (e.g. humans) and rodents (e.g., mice and rats), unless otherwise indicated. The term encompasses "full-length," unprocessed FGFR4 as well as any form of FGFR4 that results from processing in the cell. The term also encompasses naturally occurring variants of FGFR4, e.g., splice variants or allelic variants. The amino acid sequence of an exemplary human FGFR4 is shown in FIG. 18.

"FGFR4 activation" refers to activation, or phosphorylation, of the FGFR4 receptor. Generally, FGFR4 activation results in signal transduction (e.g. that caused by an intracellular kinase domain of an FGFR4 receptor phosphorylating tyrosine residues in FGFR4 or a substrate polypeptide). FGFR4 activation may be mediated by FGFR4 ligand (Gas6) binding to an FGFR4 receptor of interest. Gas6 binding to FGFR4 may activate a kinase domain of FGFR4 and thereby result in phosphorylation of tyrosine residues in the FGFR4 and/or phosphorylation of tyrosine residues in additional substrate polypeptides(s).

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The terms "cell proliferative disorder" and "proliferative disorder" refer to disorders that are associated with some degree of abnormal cell proliferation. In one embodiment, the cell proliferative disorder is cancer.

A "chemotherapeutic agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1 (see, e.g., Nicolaou et al., *Angew. Chem. Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™) and docetaxel (TAXOTERE®); chlorambucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCl-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyl-transferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "cytostatic agent" refers to a compound or composition which arrests growth of a cell either in vitro or in vivo. Thus, a cytostatic agent may be one which significantly reduces the percentage of cells in S phase. Further examples of cytostatic agents include agents that block cell cycle progression by inducing G0/G1 arrest or M-phase arrest. The humanized anti-Her2 antibody trastuzumab (HERCEPTIN®) is an example of a cytostatic agent that induces G0/G1 arrest. Classical M-phase blockers include the vincas (vincristine and vinblastine), taxanes, and topoisomerase II inhibitors such as doxorubicin, epirubicin, daunorubicin, etoposide, and bleomycin. Certain agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Cancer*, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

A cancer or biological sample which "displays FGFR4 expression, amplification, or activation" is one which, in a diagnostic test, expresses (including overexpresses) FGFR4, has amplified FGFR4 gene, and/or otherwise demonstrates activation or phosphorylation of a FGFR4.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

"Inhibiting cell growth or proliferation" means decreasing a cell's growth or proliferation by at least 10%, 20%, 30%, 40%, 50%, 60%, 70%, 80%, 90%, 95%, or 100%, and includes inducing cell death.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extra-chromosomally or at a chromosomal location that is different from its natural chromosomal location.

"Isolated nucleic acid encoding an anti-FGFR4 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The phrase "little to no binding" with respect to an antibody of the invention, as used herein, means the antibody does not show a biologically meaningful amount of binding. As would be understood in the art, amount of an activity may be determined quantitatively or qualitatively, so long as a comparison between an antibody of the invention and a reference counterpart can be done. The activity can be measured or detected according to any assay or technique known in the art, including, e.g., those described herein. The amount of activity for an antibody of the invention and its reference counterpart can be determined in parallel or in separate runs.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

A "VH subgroup III consensus framework" comprises the consensus sequence obtained from the amino acid sequences in variable heavy subgroup III of Kabat et al. In one embodiment, the VH subgroup III consensus framework amino acid sequence comprises at least a portion or all of each of the following sequences: EVQLVESGGGLVQPGGSL-RLSCAAS (SEQ ID NO:13)-H1-WVRQAPGKGLEWV (SEQ ID NO:14)-H2-RFTISRDNSKNTLYLQMNSL-RAEDTAVYYC (SEQ ID NO:15)-H3-WGQGTLVTVSS (SEQ ID NO:16).

A "VL subgroup I consensus framework" comprises the consensus sequence obtained from the amino acid sequences in variable light kappa subgroup I of Kabat et al. In one embodiment, the VH subgroup I consensus framework amino acid sequence comprises at least a portion or all of each of the following sequences:

```
                                          (SEQ ID NO: 28)-
    DIQMTQSPSSLSASVGDRVTITC (SEQ ID NO: 29)-
    L1-WYQQKPGKAPKLLIY (SEQ ID NO: 30)-
    L2-GVPSRFSGSGSGTDFTLTISSLQPEDFATYYC (SEQ ID NO: 31)
    L3-FGQGTKVEIK.
```

The term "wasting" disorders (e.g., wasting syndrome, cachexia, sarcopenia) refers to a disorder caused by undesirable and/or unhealthy loss of weight or loss of body cell mass. In the elderly as well as in AIDS and cancer patients, wasting disease can result in undesired loss of body weight, including both the fat and the fat-free compartments. Wasting diseases can be the result of inadequate intake of food and/or metabolic changes related to illness and/or the aging process. Cancer patients and AIDS patients, as well as patients following extensive surgery or having chronic infections, immunologic diseases, hyperthyroidism, Crohn's disease, psychogenic disease, chronic heart failure or other severe trauma, frequently suffer from wasting disease which is sometimes also referred to as cachexia, a metabolic and, sometimes, an eating disorder. Cachexia is additionally characterized by hypermetabolism and hypercatabolism. Although cachexia and wasting disease are frequently used interchangeably to refer to wasting conditions, there is at least one body of research which differentiates cachexia from wasting syndrome as a loss of fat-free mass, and particularly, body cell mass (Mayer, 1999, J. Nutr. 129(1S Suppl.):2565-2595). Sarcopenia, yet another such disorder which can affect the aging individual, is typically characterized by loss of muscle mass. End stage wasting disease as described above can develop in individuals suffering from either cachexia or sarcopenia.

II. Compositions and Methods

In one aspect, the invention is based, in part, on identification of a variety of FGFR4 binding agents (such as antibodies and fragments thereof). In certain embodiments, antibodies that bind to FGFR4 are provided. Antibodies of the invention are useful, e.g., for the diagnosis or treatment of cancer, liver disease, and wasting.

A. Exemplary Anti-FGFR4 Antibodies

In one aspect, the invention provides isolated antibodies that bind to FGFR4.

In certain embodiments, an anti-FGFR4 antibody binds human FGFR4 with an affinity of ≤1 nM. In some embodiments, an anti-FGFR4 antibody binds human FGFR4 with an affinity of ≤0.05 nM.

In certain embodiments, an anti-FGFR4 antibody binds mouse FGFR4 with an affinity of ≤1 nM.

In certain embodiments, an anti-FGFR4 antibody binds cynomolgus FGFR4 with an affinity of ≤1 nM.

In certain embodiments, an anti-FGFR4 antibody binds human, mouse and cynomolgus FGFR4 with an affinity of ≤1 nM.

In certain embodiments, an anti-FGFR4 antibody does not substantially bind human FGFR1, human FGFR2 and/or human FGFR3. In certain embodiment, an anti-FGFR4 antibody shows little or no binding to human FGFR1, human FGFR2 and/or human FGFR3.

In certain embodiments, an anti-FGFR4 antibody does not substantially bind mouse C3 protein (in some embodiment, a mouse C3 protein having the amino acid sequence shown in FIG. 12D). In certain embodiment, an anti-FGFR4 antibody shows little or no binding to a mouse C3 protein (in some embodiment, a mouse C3 protein having the amino acid sequence shown in FIG. 12D).

In certain embodiments, the anti-FGFR4 antibody is a humanized anti-FGFR4 antibody wherein monovalent affinity of the antibody to human FGFR4 is substantially the same as monovalent affinity of a murine antibody comprising a light chain and heavy chain variable sequence as depicted in SEQ ID NO:8 and 7, respectively. In some embodiments, the anti FGFR4 antibody is a humanized and affinity matured antibody.

In certain embodiments, an anti-FGFR4 antibody is an antagonist of FGFR4 activity.

In certain embodiments, an anti-FGFR4 antibody inhibits FGF binding to FGFR4. In some embodiments, FGF1 and/or FGF19 binding to FGFR4 is inhibited. In some embodiments, the IC50 for inhibition of FGF1 binding to FGFR4 is about 0.10 nM. In some embodiments, the IC50 for inhibition of FGF19 binding to FGFR4 is about 0.10 nM.

In certain embodiments, an anti-FGFR4 antibody inhibits cell proliferation. In some embodiments, proliferation is FGF-induced cell proliferation. In some embodiments, cell proliferation is BAF3/FGFR4 transgenic cell proliferation.

In certain embodiments, an anti-FGFR4 antibody inhibits FGF (e.g., FGF1) stimulated proliferation of cells that express FGFR4. In some embodiments, the cell is a HUH7 cell.

In certain embodiments, an anti-FGFR4 antibody inhibits FGF19-mediated inhibition of CYP7α7 expression in a cell exposed to FGF19.

In certain embodiments, an anti-FGFR4 antibody inhibits FGF19-induced phosphorylation of FGFR4, MAPK, FRS2 and/or ERK2 in a cell exposed to FGF19.

In certain embodiments, an anti-FGFR4 antibody inhibits FGF19-induced colony formation. In some embodiments, colony formation is HCC cell line colony formation. In some embodiments, the HCC cell line is JHH5.

In certain embodiments, an anti-FGFR4 antibody binds to a denatured FGFR4. In some embodiments, an anti-FGFR4 antibody binds to a reduced, denatured FGFR4. In some embodiments, binding of reduced, denatured FGFR4 is assayed using a western blot.

In certain embodiments, an anti-FGFR4 antibody binds FGFR4 expressed at a cell surface. In some embodiments, the cell is a HUH7 or JHH5 cell.

In certain embodiments, an anti-FGFR4 antibody does not significantly bind to human FGFR4 comprising a G165A mutation. In certain embodiments, an anti-FGFR4 antibody shows little or no binding to human FGFR4 comprising a G165A mutation.

In certain embodiments, an anti-FGFR4 antibody binds a polypeptide comprising, consisting essentially of or consisting of amino acid numbers 150 to 170 of the mature human FGFR4 amino acid sequence. In certain embodiments, an anti-FGFR4 antibody binds a polypeptide comprising, consisting essentially of or consisting of amino acid numbers 145 to 180 of the mature human FGFR4 amino acid sequence.

In certain embodiments, an anti-FGFR4 antibody binds a polypeptide having at least 70%, 80%, 90%, 95%, 98% sequence identity or similarity with the sequence comprising, consisting essentially of or consisting of amino acid numbers 150 to 170 of the mature human FGFR4 amino acid sequence. In certain embodiments, an anti-FGFR4 antibody binds a polypeptide having at least 70%, 80%, 90%, 95%, 98% sequence identity or similarity with the sequence comprising, consisting essentially of or consisting of amino acid numbers 145-180 of the mature human FGFR4 amino acid sequence.

In certain embodiments, an anti-FGFR4 antibody inhibits FGFR4 dimerization.

In certain embodiments, an anti-FGFR4 antibody binds at a FGFR4 dimerization interface.

In certain embodiments, an anti-FGFR4 antibody inhibits tumor growth. In some embodiments, tumor growth is liver tumor growth.

In one aspect, the invention provides an anti-FGFR4 antibody comprising at least one, two, three, four, five, or six HVRs selected from (a) HVR-H1 comprising the amino acid sequence of NHWMN (SEQ ID NO:1); (b) HVR-H2 comprising the amino acid sequence of MILPVDSETTLEQK-FKD (SEQ ID NO:2); (c) HVR-H3 comprising the amino acid sequence of GDISLFDY (SEQ ID NO:3); (d) HVR-L1 comprising the amino acid sequence of RTSQDISNFLN (SEQ ID NO:4); (e) HVR-L2 comprising the amino acid sequence of YTSRLHS (SEQ ID NO:5); and (f) HVR-L3 comprising the amino acid sequence of QQGNALPYT (SEQ ID NO:6).

In one aspect, the invention provides an antibody comprising at least one, at least two, or all three VH HVR sequences selected from (a) HVR-H1 comprising the amino acid sequence of SEQ ID NO:1; (b) HVR-H2 comprising the amino acid sequence of SEQ ID NO:2; and (c) HVR-H3 comprising the amino acid sequence of SEQ ID NO:3. In one embodiment, the antibody comprises HVR-H3 comprising the amino acid sequence of SEQ ID NO:3. In another embodiment, the antibody comprises HVR-H3 comprising the amino acid sequence of SEQ ID NO:3 and HVR-L3 comprising the amino acid sequence of SEQ ID NO:6. In a further embodiment, the antibody comprises HVR-H3 comprising the amino acid sequence of SEQ ID NO:3, HVR-L3 comprising the amino acid sequence of SEQ ID NO:6, and HVR-H2 comprising the amino acid sequence of SEQ ID NO:2. In a further embodiment, the antibody comprises (a) HVR-H1 comprising the amino acid sequence of SEQ ID NO:1; (b) HVR-H2 comprising the amino acid sequence of SEQ ID NO:2; and (c) HVR-H3 comprising the amino acid sequence of SEQ ID NO:3.

In another aspect, the invention provides an antibody comprising at least one, at least two, or all three VL HVR sequences selected from (a) HVR-L1 comprising the amino acid sequence of SEQ ID NO:4; (b) HVR-L2 comprising the amino acid sequence of SEQ ID NO:5; and (c) HVR-L3 comprising the amino acid sequence of SEQ ID NO:6. In one embodiment, the antibody comprises (a) HVR-L1 comprising the amino acid sequence of SEQ ID NO:4; (b) HVR-L2 comprising the amino acid sequence of SEQ ID NO:5; and (c) HVR-L3 comprising the amino acid sequence of SEQ ID NO:6.

In another aspect, an antibody of the invention comprises (a) a VH domain comprising at least one, at least two, or all three VH HVR sequences selected from (i) HVR-H1 comprising the amino acid sequence of SEQ ID NO:1, (ii) HVR-H2 comprising the amino acid sequence of SEQ ID NO:2, and (iii) HVR-H3 comprising an amino acid sequence selected from SEQ ID NO:3; and (b) a VL domain comprising at least one, at least two, or all three VL HVR sequences selected from (i) HVR-L1 comprising the amino acid sequence of SEQ ID NO:4, (ii) HVR-L2 comprising the amino acid sequence of SEQ ID NO:5, and (c) HVR-L3 comprising the amino acid sequence of SEQ ID NO:6.

In another aspect, the invention provides an antibody comprising (a) HVR-H1 comprising the amino acid sequence of SEQ ID NO:1; (b) HVR-H2 comprising the amino acid sequence of SEQ ID NO:2; (c) HVR-H3 comprising the amino acid sequence of SEQ ID NO:3; (d) HVR-L1 comprising the amino acid sequence of SEQ ID NO:4; (e) HVR-L2 comprising the amino acid sequence of SEQ ID NO:5; and (f) HVR-L3 comprising an amino acid sequence selected from SEQ ID NO:6.

In another aspect, an anti-FGFR4 antibody comprises a heavy chain variable domain (VH) sequence having at least 90%, 91%, 92%, 93%, 94%, 95%, 96%, 97%, 98%, 99%, or 100% sequence identity to the amino acid sequence of
EVQLVESGGGLVQPGGSLRLSCAASGYTFTNHWMNWVRQAPGKGLEWVGMILPVDSETTLEQKFKDRETISADTSKNTAYLQMNSLRAEDTAVYYCTRGDISLFDYWGQGTLVTVSS (SEQ ID NO:7). In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR4 antibody comprising that sequence retains the ability to bind to FGFR4. In certain embodiments, a total of 1 to 10 amino acids have been substituted, inserted and/or deleted in SEQ ID NO:7. In certain embodiments, substitutions, insertions, or deletions occur in regions outside the HVRs (i.e., in the FRs). Optionally, the anti-FGFR4 antibody comprises the VH sequence in SEQ ID NO:7, including post-translational modifications of that sequence. In a particular embodiment, the VH comprises one, two or three HVRs selected from: (a) HVR-H1 comprising the amino acid sequence of SEQ ID NO:1, (b) HVR-H2 comprising the amino acid sequence of SEQ ID NO:2, and (c) HVR-H3 comprising the amino acid sequence of SEQ ID NO:3.

In another aspect, an anti-FGFR4 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of DIQMTQSPSSLSASVGDRVTITCRTSQDISNFLNWYQQKPGKAFKILISYTSRLHSGVPSRFSGSG SGTDFTLTISSLQPEDFATYYCQQGNALPYTFGQGTKVEIKR (SEQ ID NO:8). In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR4 antibody comprising that sequence retains the ability to bind to FGFR4. In certain embodiments, a total of 1 to 10 amino acids have been substituted, inserted and/or deleted in SEQ ID NO:8. In certain embodiments, the substitutions, insertions, or deletions occur in regions outside the HVRs (i.e., in the FRs). Optionally, the anti-FGFR4 antibody comprises the VL sequence in SEQ ID NO:8, including post-translational modifications of that sequence. In a particular embodiment, the VL comprises one, two or three HVRs selected from (a) HVR-L1 comprising the amino acid sequence of SEQ ID NO:4; (b) HVR-L2 comprising the amino acid sequence of SEQ ID NO:5; and (c) HVR-L3 comprising the amino acid sequence of SEQ ID NO:6.

In another aspect, an anti-FGFR4 antibody is provided, wherein the antibody comprises a VH as in any of the embodiments provided above, and a VL as in any of the embodiments provided above. In one embodiment, the antibody comprises the VH and VL sequences in SEQ ID NO:7 and SEQ ID NO:8, respectively, including post-translational modifications of those sequences.

In any of the above embodiments, an anti-FGFR4 antibody is humanized. In one embodiment, an anti-FGFR4 antibody comprises HVRs as in any of the above embodiments, and further comprises an acceptor human framework, e.g. a human immunoglobulin framework or a human consensus framework. The antibodies of the invention can comprise any suitable framework variable domain sequence, provided binding activity to FGFR4 is substantially retained. For example, in some embodiments, antibodies of the invention comprise a human subgroup III heavy chain framework consensus sequence. In one embodiment of these antibodies, the framework consensus sequence comprises a substitution at position 71, 73, and/or 78. In some embodiments of these antibodies, position 71 is A, 73 is T and/or 78 is A. In one embodiment, these antibodies comprise heavy chain variable domain framework sequences of huMAb4D5-8 (HERCEPTIN®, Genentech, Inc., South San Francisco, Calif., USA) (also referred to in U.S. Pat. Nos. 6,407,213 & 5,821,337, and Lee et al., J. Mol. Biol. (2004), 340(5):1073-1093). In one embodiment, the framework sequence comprises the following acceptor human framework: DIQMTQSPSSLSASVGDRVTITC (SEQ ID NO:9)-L1-WYQQKPGKAFKILIS (SEQ ID NO:10)-L2-GVPSRFSGSGSGTDFTLTISSLQPEDFATYYC (SEQ ID NO:11)-L3-FGQGTKVEIK (SEQ ID NO:12).

In a further aspect, the invention provides an anti-FGFR4 antibody that binds to the same epitope as an anti-FGFR4 antibody provided herein. For example, in certain embodiments, an antibody is provided that binds to the same epitope as an anti-FGFR4 antibody comprising a VH sequence of SEQ ID NO:7 and a VL sequence of SEQ ID NO:8. In certain embodiments, an antibody is provided that binds to an epitope within a fragment of FGFR4 consisting of amino acids 145-180 of a sequence shown in FIG. 18 (SEQ ID NO: 39).

In a further aspect, the invention provides an anti-FGFR4 antibody that competes for binding to human FGFR4 with an anti-FGFR4 antibody comprising a VH sequence of SEQ ID NO: 7 and a VL sequence of SEQ ID NO: 8.

In a further aspect of the invention, an anti-FGFR4 antibody according to any of the above embodiments is a monoclonal antibody, including a chimeric, humanized or human antibody. In one embodiment, an anti-FGFR4 antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

In a further aspect, an antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ M$^{-1}$s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm bandpass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Plückthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall' Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348: 552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101 (34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for FGFR4 and the other is for any other antigen. In certain embodiments, bispecific antibodies may bind to two different epitopes of FGFR4. Bispecific antibodies may also be used to localize cytotoxic agents to cells which express FGFR4. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to FGFR4 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166: 1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., Blood 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, Nature 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-FGFR4 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-FGFR4 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-FGFR4 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Vol.* 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TR1 cells, as described, e.g., in Mather et al., *Annals N.Y. Acad. Sci.* 383: 44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, N.J.), pp. 255-268 (2003).

C. Assays

Anti-FGFR4 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with antibody LD1 for binding to FGFR4. In certain embodiments, such a competing antibody binds to the same epitope (e.g., a linear or a conformational epitope) that is bound by antibody LD1. Detailed exemplary methods for mapping an epitope to which an antibody binds are provided in Morris (1996) "Epitope Mapping Protocols," in *Methods in Molecular Biology* vol. 66 (Humana Press, Totowa, N.J.). In an exemplary competition assay, immobilized FGFR4 is incubated in a solution comprising a first labeled antibody that binds to FGFR4 (e.g., antibody LD1) and a second unlabeled antibody that is being tested for its ability to compete with the first antibody for binding to FGFR4. The second antibody may be present in a hybridoma supernatant. As a control, immobilized FGFR4 is incubated in a solution comprising the first labeled antibody but not the second unlabeled antibody. After incubation under conditions permissive for binding of the first antibody to FGFR4, excess unbound antibody is removed, and the amount of label associated with immobilized FGFR4 is measured. If the amount of label associated with immobilized FGFR4 is substantially reduced in the test sample relative to the control sample, then that indicates that the second antibody is competing with the first antibody for binding to FGFR4. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying anti-FGFR4 antibodies thereof having biological activity. Biological activity may include, e.g., inhibition of: FGF (e.g., FGF1) stimulated proliferation of cells (e.g. HUH7 cells) that express FGFR4, FGF19-mediated inhibition of CYP7α7 expression in a cell exposed to FGF19, FGF19-induced phosphorylation of FGFR4, MAPK, FRS2 and/or ERK2 in a cell exposed to FGF19, and FGF19-induced colony formation (in some embodiments, HCC cell line colony formation).

Antibodies having such biological activity in vivo and/or in vitro are also provided.

In certain embodiments, an antibody of the invention is tested for such biological activity. Assays for testing such biological activity are described herein.

In certain embodiments, an antibody of the invention is tested for its ability to inhibit cell growth or proliferation in vitro. Assays for inhibition of cell growth or proliferation are well known in the art. Certain assays for cell proliferation, exemplified by the "cell killing" assays described herein, measure cell viability. One such assay is the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al (1993) *J. Immunol. Meth.* 160: 81-88, U.S. Pat. No. 6,602,677. The assay may be conducted in 96- or 384-well format, making it amenable to automated high-throughput screening (HTS). See Cree et al (1995) *Anti-Cancer Drugs* 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

Another assay for cell proliferation is the "MTT" assay, a colorimetric assay that measures the oxidation of 3-(4,5-dimethylthiazol-2-yl)-2,5-diphenyltetrazolium bromide to formazan by mitochondrial reductase. Like the CellTiter-Glo™ assay, this assay indicates the number of metabolically active cells present in a cell culture. See, e.g., Mosmann (1983) *J. Immunol. Meth.* 65:55-63, and Zhang et al. (2005) *Cancer Res.* 65:3877-3882.

Cells for use in any of the above in vitro assays include cells or cell lines that naturally express FGFR4 or that have been engineered to express FGFR4. Such cells include tumor cells that overexpress FGFR4 relative to normal cells of the same tissue origin. Such cells also include cell lines (including tumor cell lines) that express FGFR4 and cell lines that do not normally express FGFR4 but have been transfected with nucleic acid encoding FGFR4. Exemplary cell lines provided herein for use in any of the above in vitro assays include HCC cell line HUH7.

In one aspect, an anti-FGFR4 antibody thereof is tested for its ability to inhibit cell growth or proliferation in vivo. In certain embodiments, an anti-FGFR4 antibody thereof is tested for its ability to inhibit tumor growth in vivo. In vivo model systems, such as xenograft models, can be used for such testing. In an exemplary xenograft system, human tumor cells are introduced into a suitably immunocompromised non-human animal, e.g., an athymic "nude" mouse. An antibody of the invention is administered to the animal. The ability of the antibody to inhibit or decrease tumor growth is measured. In certain embodiments of the above xenograft system, the human tumor cells are tumor cells from a human patient. Such xenograft models are commercially available from Oncotest GmbH (Frieberg, Germany). In certain embodiments, the human tumor cells are cells from a human tumor cell line, such as the HUH7 HCC tumor cell line. In certain embodiments, the human tumor cells are introduced into a suitably immunocompromised non-human animal by subcutaneous injection or by transplantation into a suitable site, such as a mammary fat pad. In certain embodiments, the xenograft model is a transgenic mouse that overexpresses FGF19, e.g., as described herein and in nicholes et al, *Am J Pathol* 160:2295-2307.

It is understood that any of the above assays may be carried out using an immunoconjugate of the invention in place of or in addition to an anti-FGFR4 antibody.

It is understood that any of the above assays may be carried out using anti-FGFR4 antibody and an additional therapeutic agent, such as a chemotherapeutic agent.

D. Immunoconjugates

The invention also provides immunoconjugates comprising an anti-FGFR4 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethyl-lauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770, 701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, STAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-FGFR4 antibodies provided herein is useful for detecting the presence of FGFR4 in a biological sample. The term "detecting" as used herein encompasses quantitative or qualitative detection. In certain embodiments, a biological sample comprises a cell or tissue, such as breast, pancreas, esophagus, lung and/or brain.

In one embodiment, an anti-FGFR4 antibody for use in a method of diagnosis or detection is provided. In a further aspect, a method of detecting the presence of FGFR4 in a biological sample is provided. In certain embodiments, the method comprises contacting the biological sample with an anti-FGFR4 antibody as described herein under conditions permissive for binding of the anti-FGFR4 antibody to FGFR4, and detecting whether a complex is formed between the anti-FGFR4 antibody and FGFR4. Such method may be an in vitro or in vivo method. In one embodiment, an anti-FGFR4 antibody is used to select subjects eligible for therapy with an anti-FGFR4 antibody, e.g. where FGFR4 is a biomarker for selection of patients.

Exemplary disorders that may be diagnosed using an antibody of the invention include cancer (for example, cancer of the breast, lung, pancreas, brain, kidney, ovary, stomach, leukemia, uterine endometrium, colon, prostate, pituitary, mammary fibroadenoma, head and neck, soft tissue, neuroblastomas, melanoma, endometrium, testis, cholangiocarcinoma, gallbladder and liver).

In certain embodiments, labeled anti-FGFR4 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-FGFR4 antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide an EGFR antagonist (such as erlotinib), an anti-angiogenic agent (such as VEGF antagonist, such as an anti-VEGF antibody) or a chemotherapeutic agent (such as a taxoid or a platinum agent). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-FGFR4 antibodies provided herein may be used in therapeutic methods.

In one aspect, an anti-FGFR4 antibody for use as a medicament is provided. In further aspects, an anti-FGFR4 antibody for use in treating cancer is provided. In further embodiments, an anti-FGFR4 antibody for use in treating liver disease (e.g., cirrhosis) is provided. In further embodiments, an anti-FGFR4 antibody for use in treating wasting disorders is provided. In certain embodiments, an anti-FGFR4 antibody for use in a method of treatment is provided. In certain embodiments, the invention provides an anti-FGFR4 antibody for use in a method of treating an individual having cancer comprising administering to the individual an effective amount of the anti-FGFR4 antibody. In certain embodiments, the invention provides an anti-FGFR4 antibody for use in a method of treating an individual having a liver disorder (such as cirrhosis) comprising administering to the individual an effective amount of the anti-FGFR4 antibody. In one such embodiment, the method further comprises administering to the individual an effective amount of at least one additional therapeutic agent, e.g., as described below. In further embodiments, the invention provides an anti-FGFR4 antibody for use in inhibiting cell proliferation. In certain embodiments, the invention provides an anti-FGFR4 antibody for use in a method of inhibiting cell proliferation in an individual comprising administering to the individual an effective of the anti-FGFR4 antibody to inhibit cell proliferation. An "individual" according to any of the above embodiments is preferably a human.

In a further aspect, the invention provides for the use of an anti-FGFR4 antibody in the manufacture or preparation of a medicament. In one embodiment, the medicament is for treatment of cancer. In a further embodiment, the medicament is for use in a method of treating cancer comprising administering to an individual having cancer an effective amount of the medicament. In one embodiment, the medicament is for treatment of a liver disorder (such as cirrhosis, non-alcoholic fatty liver disease, biliary cirrhosis, sclerosing cholengitis, progressive familial intrahepatic cholestasis). In a further embodiment, the medicament is for use in a method of treating a liver disorder (such as cirrhosis, non-alcoholic fatty liver disease, biliary cirrhosis, sclerosing cholengitis, progressive familial intrahepatic cholestasis) comprising administering to an individual having the liver disorder an effective amount of the medicament. In one such embodiment, the method further comprises administering to the individual an effective amount of at least one additional therapeutic agent, e.g., as described below. In a further embodiment, the medicament is for inhibiting cell proliferation. In a further embodiment, the medicament is for use in a method of inhibiting cell proliferation in an individual comprising administering to the individual an amount effective of the medicament to inhibit cell proliferation. An "individual" according to any of the above embodiments may be a human.

In a further aspect, the invention provides a method for treating a cancer. In one embodiment, the method comprises administering to an individual having such cancer an effective amount of an anti-FGFR4 antibody. In one such embodiment, the method further comprises administering to the individual an effective amount of at least one additional therapeutic agent, as described below. An "individual" according to any of the above embodiments may be a human.

In a further aspect, the invention provides a method for treating a liver disorder (such as cirrhosis, non-alcoholic fatty liver disease, biliary cirrhosis, sclerosing cholengitis, progressive familial intrahepatic cholestasis). In one embodiment, the method comprises administering to an individual having such a liver disorder an effective amount of an anti-FGFR4 antibody. In one such embodiment, the method further comprises administering to the individual an effective amount of at least one additional therapeutic agent, as described below. An "individual" according to any of the above embodiments may be a human.

In a further aspect, the invention provides a method for treating a wasting disorder. In one embodiment, the method comprises administering to an individual having such a wasting disorder an effective amount of an anti-FGFR4 antibody. In one such embodiment, the method further comprises administering to the individual an effective amount of at least one additional therapeutic agent, as described below. An "individual" according to any of the above embodiments may be a human.

In a further aspect, the invention provides a method for inhibiting cell proliferation in an individual. In one embodiment, the method comprises administering to the individual an effective amount of an anti-FGFR4 antibody to inhibit cell proliferation. In one embodiment, an "individual" is a human.

In a further aspect, the invention provides pharmaceutical formulations comprising any of the anti-FGFR4 antibodies provided herein, e.g., for use in any of the above therapeutic methods. In one embodiment, a pharmaceutical formulation comprises any of the anti-FGFR4 antibodies provided herein and a pharmaceutically acceptable carrier. In another embodiment, a pharmaceutical formulation comprises any of the anti-FGFR4 antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is a chemotherapeutic agent. In certain embodiments, an additional therapeutic agent is an anti-angiogenesis agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-FGFR4 antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-FGFR4 antibody.

III. Examples

A. Treatment with Anti-FGFR4 Antibodies Inhibited Hepatocellular Carcinoma

Materials and Methods

In Silico Expression Analysis.

For expression analysis, box- and whisker-plots were generated for FGFR4 with the normalized gene expression data extracted from the BioExpress™ database (Gene Logic, Gaithersburg, Md.). The distribution of FGFR4 expression in normal and cancer tissues was evaluated using the signals associated with probe 204579_at.

Immunohistochemistry.

Formalin-fixed paraffin-embedded tissue sections were treated for antigen retrieval using Trilogy (Cell Marque, Rocklin, Calif.) and then incubated with 10 μg/ml anti-FGFR4 antibody (8G11; Genentech, South San Francisco, Calif.). The immunostaining was accomplished using a biotinylated secondary antibody, an ABC-HRP reagent (Vector Laboratories, Burlingame, Calif.), and a metal-enhanced DAB colorimetric peroxidase substrate (Thermo Fisher Scientific, Rockford, Ill.).

Semi-Quantitative RT-PCR.

Total RNA was extracted using the RNeasy kit (Qiagen, Valencia, Calif.). Specific primers and fluorogenic probes were used to amplify and quantitate gene expression (31). The gene-specific signals were normalized to the RPL19 housekeeping gene. All TaqMan qRT-PCR reagents were purchased from Applied Biosystems (Foster City, Calif.). A minimum of a triplicate set of data was analyzed for each condition. Data are presented as the mean±SEM.

Immunoprecipitation and Immunoblotting.

Lysates of cultured cells or frozen tissues were prepared with RIPA lysis buffer (Millipore, Billerica, Mass.) supplemented with Completed EDTA-free protease inhibitor cocktail (Roche, Indianapolis, Ind.), phosphatase inhibitor cocktails 1 and 2 (Sigma-Aldrich, St. Louis, Mo.), 2 mM sodium fluoride, and 2 mM sodium orthovanadate. Equal amounts of protein, as determined by BCA assay (Thermo Fisher Scientific) were analyzed by immunoblot analysis using antibodies against FGFR4 (8G11; Genentech), FGFR3 (Santa Cruz Biotechnology, Santa Cruz, Calif.), FGFR2 (GeneTex, Irvine, Calif.) and FGFR1 (Santa Cruz Biotechnology). For the human liver lysates, the immunoblot analysis was preceded by the immunoprecipitation of FGFR4 as described previously (16).

Generation of FGFR4 Monoclonal Antibodies.

FGFR4 null mice were immunized with recombinant human and mouse FGFR4-Fc chimeric proteins (Genentech). Spleens were harvested after 8 weeks and hybridomas were generated. Cultured supernatants were collected and screened by solid phase antibody binding assay against the immunogens. Positive cell lines were further screened using solid phase receptor binding assay for their efficacy at inhibiting FGF1 and FGF19 binding to human and mouse FGFR4. The LD1-producing hybridoma was subcloned twice to insure monoclonality.

Molecular Cloning of LD1.

Total RNA was extracted from hybridoma cells producing muLD1 using the RNeasy Mini kit (Qiagen). The variable light and variable heavy domains were amplified using reverse transcription-PCR (RT-PCR). The forward primers were specific for the $NH_2$-terminal amino acid sequence of the variable light and variable heavy regions. Respectively, the light chain and heavy chain reverse primers were designed to anneal to regions in the constant light and constant heavy domain 1 that are highly conserved across species. Amplified variable light chain was cloned into a mammalian expression vector containing the human κ constant domain. Amplified variable heavy chain was inserted into a mammalian expression vector encoding the full-length human IgG1 constant domain. The chimeric antibody was transiently expressed as previously described (16). Experiments described in this Part A of the Examples (including FIGS. 1-9) used chimeric LD1.

Solid Phase Antibody Binding Assay.

Maxisorp 96 well plates were coated overnight at 4° C. with 50 µl of 2 µg/ml anti-human immunoglobulin Fc fragment-specific (Jackson ImmunoResearch Laboratories, West Grove, Pa.) or anti-FLAG antibody (Sigma-Aldrich). The non-specific binding sites were saturated with 200 µl PBS/3% bovine serum albumin (BSA) for 1 hour and FGFRs-IgG (Genentech and R&D Systems, Minneapolis, Minn.) or FLAG tagged-FGFR4 (FGFR4ΔTM-FLAG) were incubated in PBS/0.3% BSA for 1 hour. The plates were washed and incubated for 1 hour with anti-FGFR4 antibodies in PBS/0.3% BSA. The bound antibodies were detected using an HRP-conjugated anti-IgG (Jackson ImmunoResearch Laboratories) and the TMB peroxidase colorigenic substrate (KPL, Gaithersburg, Md.).

Flow Cytometry Analysis.

Cells for flow cytometry analysis were resuspended with PBS containing 5 mM EDTA and washed with PBS containing 2% heat-inactivated fetal bovine serum (FBS). All subsequent steps were carried out on ice. Cells ($1 \times 10^6$) were incubated with a primary antibody (LD1 or isotype control) for 30 minutes, followed by incubation with phycoerythrin (PE)-conjugated anti-human IgG antibody (Jackson ImmunoResearch). Cells were analyzed with a FACScan flow cytometer (BD Biosciences, San Jose, Calif.).

DNA Constructs.

The human FGFR4 (hFGFR4) cDNA was cloned as described previously (16). The extracellular domain of FGFR4 was also subcloned into the expression vector pCMV-Tag4A (Stratagene, La Jolla, Calif.) to obtain a secreted form of FGFR4 with a FLAG tag at the C-terminal end (FGFR4ΔTM-Flag). Single nucleotide mutations were introduced in the FGFR4ΔTM-Flag construct using the QuikChange XL Site-Directed Mutagenesis Kit (Stratagene). We also generated a human FGFR4-FGFR1 chimeric construct (hFGFR4/R1) that contained the extracellular and the transmembrane domains of human FGFR4 (amino acid residues M1-G392 of FGFR4) fused to the cytoplasmic domain of human FGFR1 (amino acid residues K398-R820 of FGFR1). The amino acid sequence joining FGFR4 (bold) to FGFR1 (plain) is . . . AVLLLLAGLYRGKMKSG.(SEQ ID NO: 32) . . . . The hFGFR4 cDNA or hFGFR4/R1 cDNA was ligated into the pQCXIP retroviral bicistronic expression vector (Clontech Laboratories, Mountain View, Calif.).

FGFR4ΔTM-Flag-Conditioned Medium.

HEK293 cells were transfected with the wild type or mutant FGFR4ΔTM-Flag constructs or the corresponding empty vector and maintained in serum free PS25 medium for 72 to 96 hours. The resulting media were filtered, supplemented with HEPES pH 7.2 (final concentration 40 mM), and protease inhibitors and stored at 4° C. until used.

Cell Culture and Stable Cell Lines.

HEK293, HEPG2, and HEP3B cells were obtained from American Type Culture Collection (ATCC, Manassas, Va.) and maintained in F-12:DMEM mix (50:50) supplemented with 10% FBS and 2 mM L-glutamine. HUH7 and PLC/PRF/5 cells were cultured in DMEM high glucose, 10% FBS. JHH4, JHH5, and JHH7 cells were purchased from the Japanese Cancer Research Resources Bank (Tokyo, Japan) and maintained in Williams Medium E supplemented with 10% FBS and 2 mM L-glutamine. SNU449 cells were obtained from ATCC and maintained in RPMI 1640 containing 10% FBS and 2 mM L-glutamine. BaF3 cells were maintained in RPMI 1640 (Life Technologies, Carlsbad, Calif.) supplemented with 10% FBS, 1 ng/ml IL-3, and 2 mM L-glutamine. L6 cells were obtained from ATCC and maintained in DMEM high glucose supplemented with 10% FBS.

Cultures of BaF3 and L6 cells were infected with the empty, hFGFR4, or hFGFR4/R1 retroviral expression vectors according to the manufacturer's recommendations and selected in media containing 2.5 µg/mL puromycin (Life Technologies) for 10 to 12 days. From the selected pools, the fifth percentile of highest expressing cells was isolated by Fluorescence Activated Cell Sorting (FACS) using an anti-FGFR4 antibody (8G11; Genentech). The resulting pools of cells expressing high levels of FGFR4, high levels of FGFR4/R1, and the control cells stably transfected with an empty vector were maintained in complete medium containing 2.5 µg/mL puromycin.

Mitogenic Assays.

BaF3/control, BaF3/FGFR4, and BaF3/FGFR4/R1 cells were washed twice and seeded in 96-well plates (22,500 cells/well) in RPMI 1640 supplemented with 10% FBS, 2 mM L-glutamine, and 2 µg/ml heparin. FGFs were added to each well and the cells were incubated at 37° C. for 72 hours. The relative cell density was measured using CellTiter-Glo (Promega, Madison, Wis.) according to the manufacturer's recommendations.

Anti-FGFR4 Antibody Inhibition of FGF Pathway Activation.

Cells were serum starved for 24 hours in the absence or presence of LD1 or an isotype control antibody. They were then stimulated with 5 ng/ml FGF1 (FGF acidic, R&D Systems) and 10 µg/ml heparin for 5 minutes. The cells were lysed with RIPA lysis buffer (Millipore) supplemented with Complete EDTA-free protease inhibitor cocktail (Roche), phosphatase inhibitor cocktails 1 and 2 (Sigma-Aldrich), 2 mM sodium fluoride, and 2 mM sodium orthovanadate. Equal amounts of protein were analyzed by immunoblot using antibodies against phospho-ERK1/2, phospho-FRS2, ERK1/2 (Cell Signaling Technology, Danvers, Mass.), and FRS2 (Millipore).

Clonogenic Assay.

HUH7 (5,000 cells/well), PLC/PRF/5 (2,000 cells/well), JHH5 (500 cells/well), or JHH5/hFGFR4 shRNA (500 cells/well) cells were seeded in 2 ml medium/well in 6 well plates, in triplicate. Three hours after seeding, the HUH7 and PLC/PRF/5 cells were treated without or with anti-FGFR4 antibody (chLD1; Genentech). Antibody was replaced twice weekly for the duration of the experiment (14 days). For the JHH5 and JHH5/hFGFR4 shRNA cells, treatment without or with 2 mg/ml doxycycline was initiated 3 hours after seeding, and replaced three times weekly for the duration of the experiment. Cells were washed with PBS and stained with 0.5% crystal violet solution. Colonies were counted using MetaMorph software (Molecular Devices, Sunnyvale, Calif.).

In Vivo Experiments.

All animal protocols were approved by an Institutional Animal Care and Use Committee. Female nu/nu mice that were 5 to 6 weeks old were obtained from Charles River Laboratories International (Wilmington, Mass.). The mice were provided standard feed and water ad libitum until 12 hours before injection, at which time feed was removed. Mice were given intraperitoneal (IP) injections (10 mg/kg) of a control or an anti-FGFR4 (chLD1) antibody. Eighteen hours later the mice received vehicle (PBS) or 1 mg/kg FGF19 intravenously (IV). After 30 minutes, mice from all groups were necropsied and tissue samples were collected, frozen in liquid nitrogen, and stored at $-70°$ C. Total RNA from frozen tissue samples was prepared using the RNeasy kit (Qiagen). Groups of 3 to 5 animals were analyzed for each condition. Data are presented as the mean±SEM and were analyzed by the Student's t-test.

For xenograft experiments, 6- to 8-week-old nu/nu female mice (Charles River Laboratories International) were inoculated subcutaneously with $5 \times 10^6$ cells (200 ul/mouse) and Matrigel (BD Biosciences). After 7 days, mice bearing tumors of equivalent volumes (~150 mm$^3$) were randomized into groups (n=10) and treated IP twice weekly. Tumors were measured with an electronic caliper (Fowler Sylvac Ultra-Cal Mark III; Fred V. Fowler Company, Newton, Mass.) and average tumor volume was calculated using the formula: $(W^2 \times L)/2$ where W and L are the smaller diameter and larger diameter, respectively. Data are presented as the mean tumor volume±SEM and were analyzed by the Student's t-test.

The FGF19 transgenic mice were produced as described previously (32). The FGFR4 null mutant (FGFR4-KO) animals were constructed as reported previously (33) and provided by W. L. McKeehan under a Material Transfer Agreement (University of Texas Southwestern Medical Center, Dallas, Tex.). Mice that both overexpressed FGF19 and lacked the FGFR4 receptor (FGF19-TG:FGFR4-KO) were fabricated by crossing young adult FGF19-TG males with young adult FGFR4-KO females. The presence of both gene engineering events was confirmed at weaning by PCR on tail DNA.

Results

FGFR4 is Required for Hepatocarcinogenesis in FGF19 Transgenic Mice.

Figure 1E:
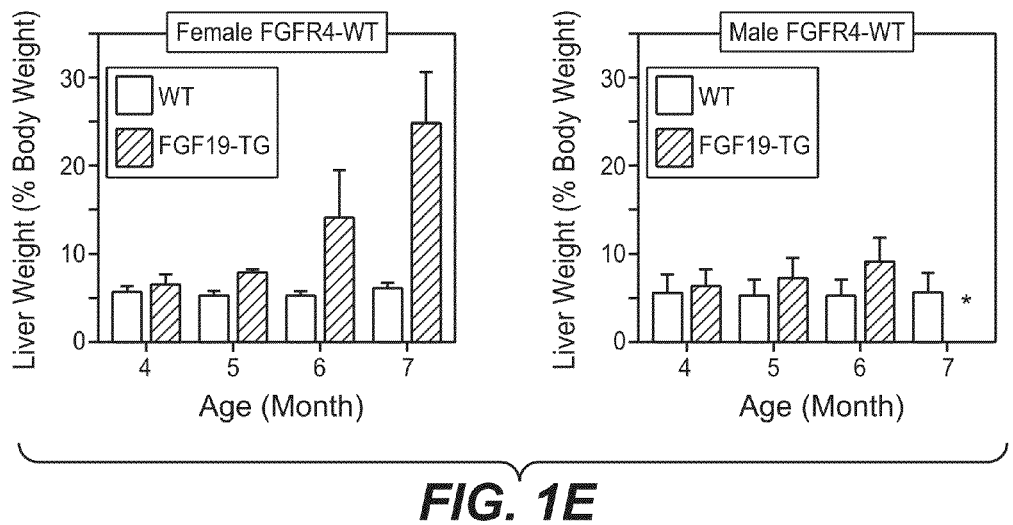
Figure 1F:
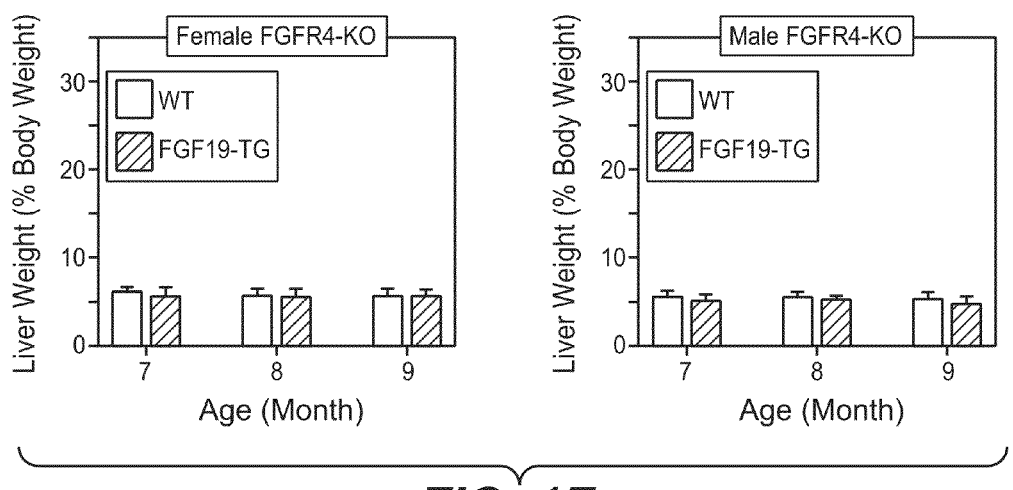

The exogenous expression of FGF19 in transgenic mice was previously shown to cause HCC by the age of 10 months (18). To assess whether FGFR4 is involved in this FGF19-mediated tumorigenesis we bred the FGF19 transgenic (FGF19-TG) mice with FGFR4 knockout (FGFR4-KO) mice or FGFR4 wild type (FGFR4-WT) mice. The mice were necropsied at various time points and liver carcinogenesis was assessed by performing gross and histological examinations and by measuring preneoplastic hepatocellular proliferation (i.e. BrdU incorporation). The development of HCC in FGF19-TG:FGFR4-WT mice was as previously described (18). Contrary to the FGF19-TG:FGFR4-WT mice, the FGF19-TG:FGFR4-KO mice did not develop gross or histological evidence of hepatocellular neoplasia at any time during this experiment (FIG. 1A). Also, preneoplastic hepatocellular proliferation was significantly elevated in FGF19-TG mice that had the FGFR4-WT genotype, but was not evident in the FGF19-TG:FGFR4-KO littermates (FIG. 1B). Consistent with the previously reported higher frequency and severity of tumor development in female FGF19-TG mice (18), the BrdU incorporation was increased in FGF19-TG:FGFR4-WT females as compared to the corresponding males (compare left and right panels of FIG. 1B). We also evaluated the effect of diethylnitrosamine (DEN), a potent liver carcinogen, on the development of HCC in FGF19-TG mice. The administration of DEN accelerated the development of HCC in FGF19-TG:FGFR4-WT mice. The entire range of preneoplastic and neoplastic lesions—altered (basophilic) hepatic foci, pericentral hepatocyte dysplasia, well differentiated hepatocellular neoplasms, and aggressive hepatocellular carcinomas—was seen in livers from all DEN-treated FGF19-TG:FGFR4-WT animals by 4 months of age (FIG. 1D) as compared to 10 months of age for the non-DEN treated FGF19-TG:FGFR4-WT mice. The cardinal morphologic characteristic of livers from almost all FGF19-TG:FGFR4-WT mice at all time points was grossly evident nodules of HCC on multiple lobes (FIG. 1C). The tumor burden was evaluated by measuring liver weight. The relative liver weights increased progressively at all time points in FGF19-TG:FGFR4-WT mice treated with DEN (FIG. 1E). Interestingly, the increase in liver weight was more pronounced in females (2.7-fold at 6 months) than in males (1.8-fold at 6 months) (compare left and right panels of FIG. 1E). It should be noted that none of the males survived past 6 months of age (FIG. 1E). The hepatocarcinogenesis observed in the FGF19-TG:FGFR4-WT mice treated with DEN was abolished by the removal of FGFR4 expression in the FGFR4-KO mice. Accordingly, the relative liver weight of FGF19-TG:FGFR4-KO mice remained constant during adulthood (FIG. 1F). These results suggest that FGFR4 expression is required for FGF19-promoted hepatocarcinogenesis in mice.

Generation of an Anti-FGFR4 Neutralizing Monoclonal Antibody.

To evaluate whether targeting FGFR4 could have a therapeutic impact in HCC we generated an FGFR4-specific monoclonal antibody by immunizing FGFR4-KO mice with recombinant mouse and human FGFR4. One of the resulting clones, designated as LD1, was selected for the specificity of its binding to mouse, cynomolgus monkey, and human FGFR4 (FIG. 2A). This antibody did not bind to mouse or human FGFR1, FGFR2, or FGFR3 (FIG. 2A). Surface plasmon resonance analysis revealed that LD1 bound to mouse, cynomolgus monkey, and human FGFR4 with comparable affinity (FIG. 2B). We used flow cytometry to evaluate whether LD1 bound to FGFR4 present at the cell surface. The specific binding of LD1 to HEK293 cells stably transfected with human FGFR4 was proportional to the concentration of antibody added (FIG. 2C). There was no binding of LD1 to control HEK293 cells stably transfected with an empty vector. Together these data demonstrate that LD1 binds specifically to mouse, cynomolgus monkey, and human FGFR4 and also recognizes the human receptor when expressed at the cell surface.

Figure 2E:
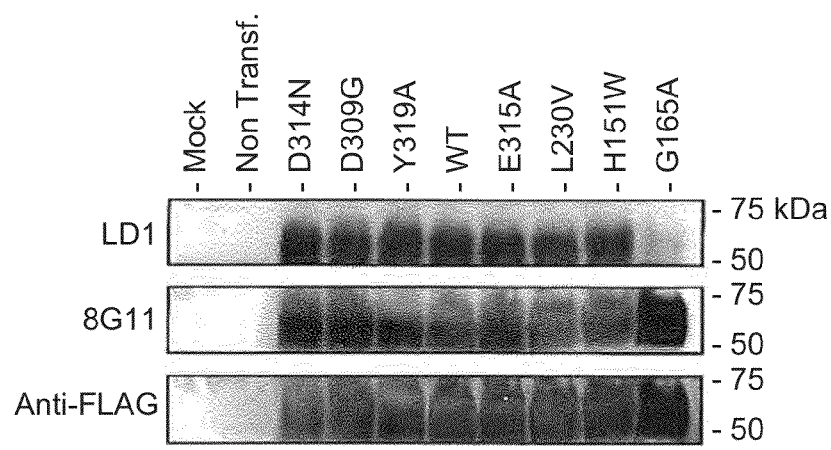
Figure 2F:
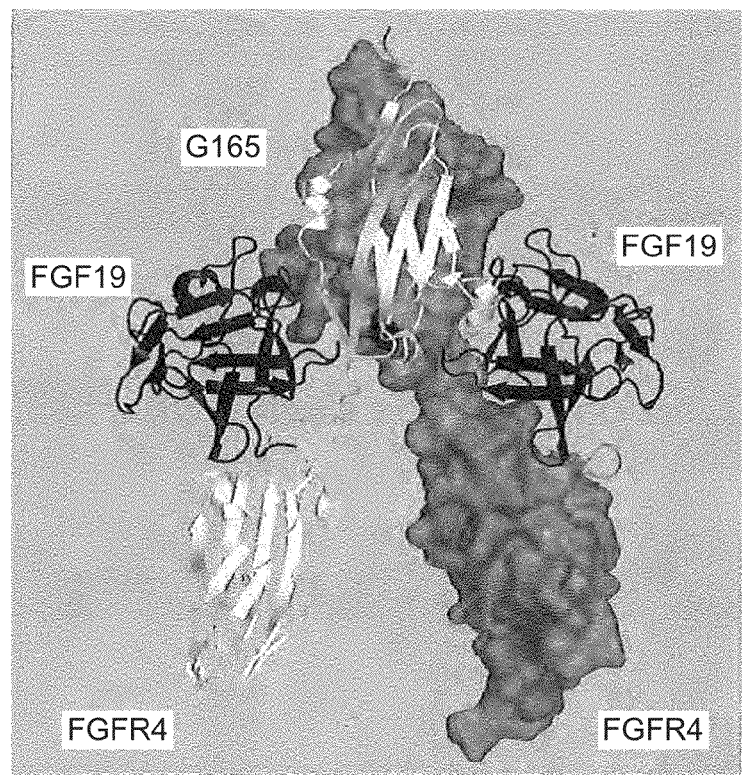

To map the FGFR4 epitope for LD1, we compared the amino acid sequences of mouse and human FGFR1, FGFR2, FGFR3, and FGFR4. Eight amino acids were selected based on their similarity between the FGFR4 orthologs and their dissimilarity in the FGFR1-3 orthologs. These amino acids in FGFR4 were substituted with the amino acids present at the equivalent positions in FGFR3 to generate eight different mutant constructs of human FGFR4. These constructs were expressed and evaluated for LD1 binding using a solid phase binding assay. LD1 bound equally well to wild type FGFR4 and most of the mutant constructs; G165A was the only FGFR4 mutant for which LD1 binding was compromised (FIG. 2D). LD1 did not bind to the negative control wild type FGFR3 (FIG. 2D). We also tested the binding of LD1 to the mutant constructs using immunoblot analysis. All previously described protein constructs were reduced, denatured, electrophoresed, and electro-transferred to nitrocellulose. The nitrocellulose membrane was sequentially incubated with LD1, an anti-FGFR4 antibody recognizing a different epitope (8G11), or an anti-FLAG antibody. The anti-FLAG antibody and 8G11 detected wild type FGFR4 and all FGFR4 mutant constructs while LD1 detected all constructs equally well with the exception of the G165A mutant (FIG. 2E). No protein band was detected by any of the antibodies in the control lanes (FIG. 2E). We generated a three-dimensional model of an FGFR4 dimer bound to two molecules of FGF19 to visualize the location of G165 (FIG. 2F). G165 is localized in the center of the FGFR4-FGF19 complex at the point of contact between the two FGFR4 units. Together these results show that G165 is critical for the interaction of LD1 with human FGFR4. The binding of LD1 to reduced and denatured FGFR4 also suggests that the epitope does not depend on ternary confirmation.

Figure 3A:
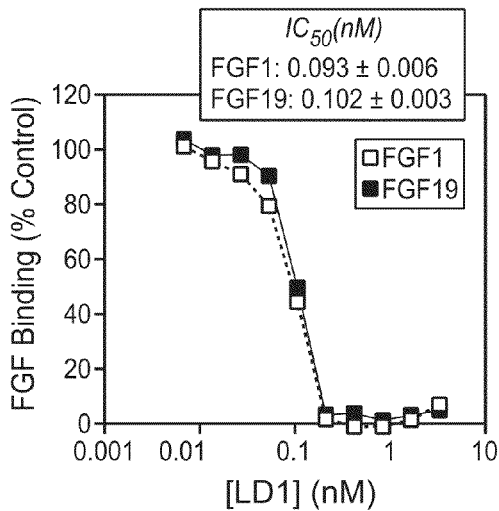
FIGS. 3A-3D: LD1 inhibits FGFR4 activities. A, LD1 inhibits FGFR4 binding to FGF1 and FGF19 as determined by solid phase binding assay. B, LD1 inhibits FGF1-stimulated proliferation of BaF3 cells stably expressing FGFR4/R1. C, LD1 inhibits FGFR4 signaling in L6 cells stably expressing FGFR4. D, Cell surface expression of FGFR4 protein in a subset of liver tumor cell lines as determined by FACS analysis using LD1.
Figure 3B:
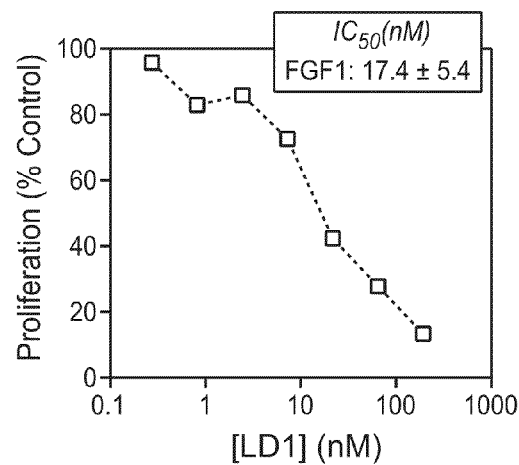

Next we tested whether LD1 could block the binding of FGF1 and FGF19 to FGFR4 using a solid phase receptor-binding assay. The LD1 inhibition of FGF binding was dose-dependent and reached an IC50 of 0.093±0.006 nM for FGF1 and 0.102±0.003 nM for FGF19 (FIG. 3A). To evaluate whether LD1 could inhibit the functions of FGFR4 expressed at the cell surface we first utilized a BaF3 murine pro-B cell line stably transfected with a chimeric construct that encodes for the extracellular domain of FGFR4 and the intracellular domain of FGFR1 (BaF3/FGFR4/R1). The wild type BaF3 cell line is an interleukin-3 (IL-3)-dependent cell line that does not express any FGFRs. BaF3 cells transfected with FGFRs proliferate in the absence of IL-3 when stimulated with FGF and heparin (21). The transfection of this construct allowed us to substitute FGFs for IL-3 to support the growth of the BaF3 cells. In the presence of 5 nM FGF1, LD1 inhibited the proliferation of BaF3/FGFR4/R1 cells with an IC50 of 17.4±5.4 nM (FIG. 3B).

Figure 3C:
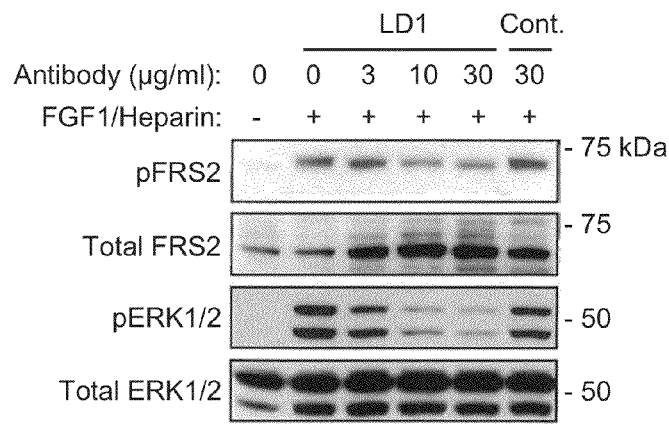

We also used the L6 rat skeletal muscle cell line stably transfected with a vector expressing FGFR4 (L6/FGFR4) to evaluate the effect of LD1 on FGF signaling. The addition of FGF1 and heparin to the L6/FGFR4 cell cultures activated the FGFR pathway as demonstrated by the phosphorylation of FGFR substrate 2 (FRS2) and extracellular signal-regulated kinase 1/2 (ERK1/2) while LD1 inhibited the ligand-induced phosphorylation of these secondary messengers in a dose-dependent manner (FIG. 3C). Interestingly, the addition of LD1 also triggered an increase in total FRS2 content in these cells (FIG. 3C).

Figure 3D:
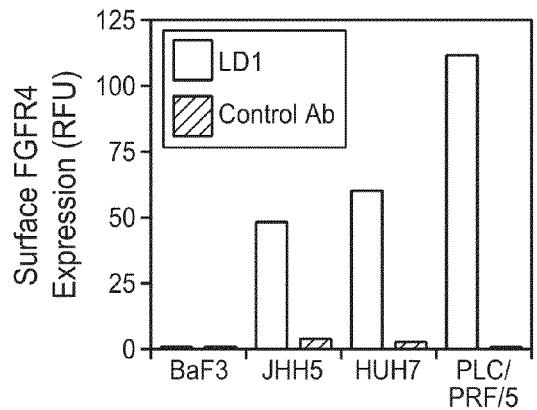

Using flow cytometry we evaluated the binding of LD1 and confirmed the expression of FGFR4 at the cell surface of a subset of HCC cell lines. LD1 bound most highly to PLC/PRF/5 and bound to a lesser extent to HUH7 and JHH5 cells (FIG. 3D). The binding of a control antibody to the surface of these cells was negligible (FIG. 3D). Furthermore, the binding of LD1 and the control antibody to the surface of BaF3 cells, which were used as a negative control because they do not express FGFR4, was also negligible (FIG. 3D).

LD1 Inhibits FGFR4 Functions in Liver Cancer Cell Lines.

Figure 4A:
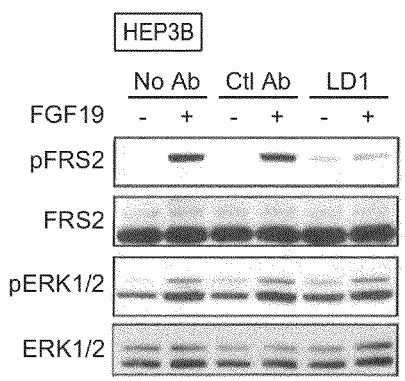
FIGS. 4A-4F: LD1 inhibits FGFR4 biological activities in liver cancer cell lines. A, LD1 inhibits FGFR4 signaling in HEP3B cells as evaluated by Western blot. B, LD1 inhibits the FGFR4-regulated CYP7α1 repression in HEP3B cells. CYP7α1 levels are represented as fold expression relative to the level in untreated cells. C, LD1 inhibits FGFR4-regulated c-Fos expression in a panel of liver cancer cell lines. The results are represented as fold expression relative to the c-Fos level in untreated cells. D, Inhibition of colony formation by repression of FGFR4 expression in JHH5 cells stably transfected with an FGFR4 shRNA doxycycline-inducible vector. E, LD1 inhibits HCC cell line colony formation. F, Enumeration of LD1-inhibited liver cancer cell line colony formation. The values are represented as percent of the number of colonies enumerated in the absence of added LD1.
Figure 7A:
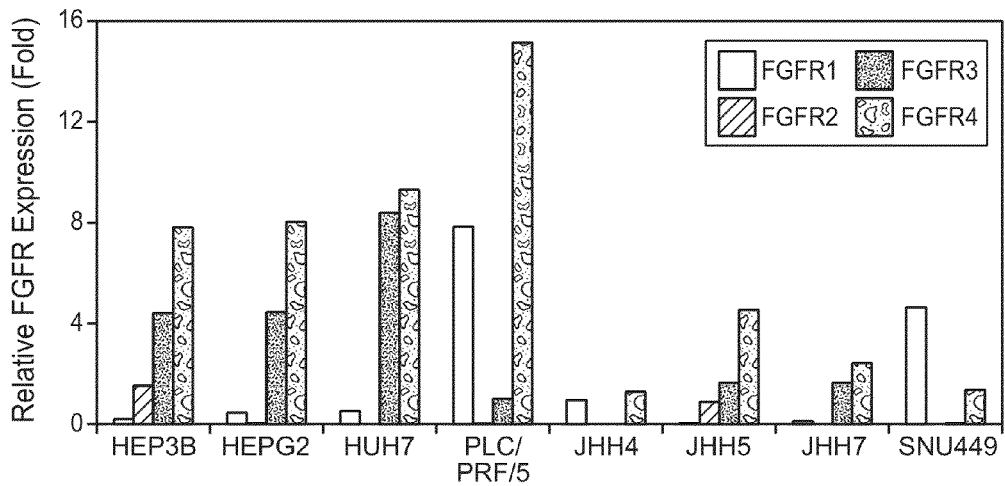
FIGS. 7A and 7B: Expression of FGFRs in liver cancer cell lines. A, FGFR4 mRNA expression in a panel of liver tumor cell lines as determined by qRT-PCR. The values are represented as fold expression relative to the FGFR1 levels in the JHH4 cell line. B, FGFR4 protein expression in the same panel of cell lines as in FIG. S1A as determined by Western blot.
Figure 7B:
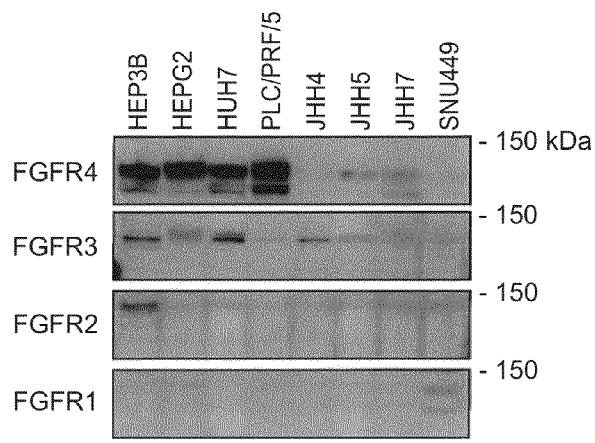

The inhibitory activity of LD1 was characterized using liver cancer cell lines with various levels of endogenous FGFR (i.e. FGFR1-4) expression (FIG. 7). In HEP3B cells, the addition of FGF19 triggered the phosphorylation of FRS2 and ERK1/2 while LD1 inhibited the FGF19-stimulated phosphorylation of FRS2 (FIG. 4A), similar to its effect on L6/FGFR4 cells. LD1, however, did not appreciably alter the phosphorylation of ERK1/2 (FIG. 4A).

Figure 4B:
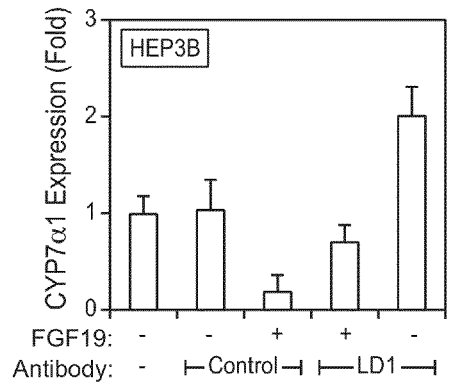
Figure 8:
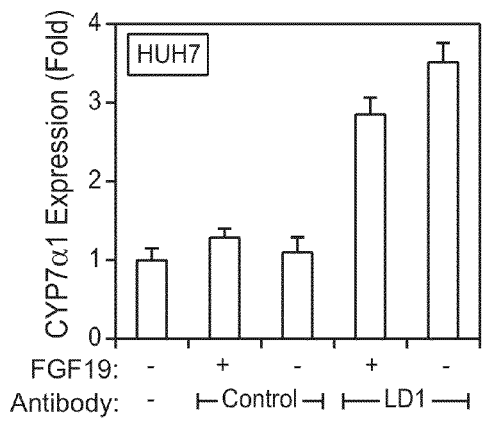
FIG. 8: LD1 inhibits FGFR4 biological activities in HUH7 cells. LD1 inhibits the FGFR4-regulated CYP7α1 repression in HUH7 cells. CYP7α1 levels are represented as fold expression relative to the level in untreated cells.

The expression of cytochrome P450 7α1 (CYP7α1) and c-Fos are modulated by FGF19 in liver cell lines (16, 22). We tested whether LD1 could inhibit this FGF19-mediated gene modulation. In HEB3B cells, the addition of FGF19 reduced the expression of CYP7α1 by 81% (FIG. 4B). The addition of LD1 restored 67% of the basal expression of CYP7α1 (FIG. 4B). In the absence of added FGF19, LD1 increased CYP7α1 expression by 2-fold (FIG. 4B). Although the addition of FGF19 did not affect the expression of CYP7α1 in HUH7 cells, the addition of LD1 had a similar effect as in HEP3B cells, increasing the expression of this gene by 2.9- and 3.5-fold in the presence or the absence of FGF19, respectively (FIG. 8). The addition of a negative control antibody had no effect on the expression of CYP7α1 in either HEP3B or HUH7 cells (FIGS. 4B and 8, respectively). Interestingly, the addition of LD1 leads to the upregulation of CYP7α1 expression in the absence of exogenously added FGFR4 ligand in both HEP3B and HUH7 cells. This indicates that LD1 inhibits the FGFR4 basal activity possibly maintained by an FGFR4 ligand autocrine/paracrine loop.

Figure 4C:
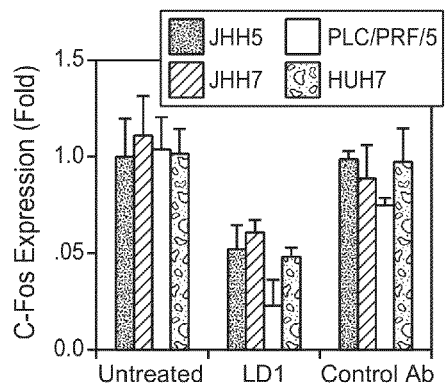

To further evaluate the effect of LD1 on the basal activity of FGFR4 we measured the expression of c-Fos in the absence of exogenously added FGFR4 ligand. The activation of the FGFR4 pathway was previously shown to increase the expression of c-Fos (16). The addition of LD1 decreased the basal expression of c-Fos by 50% in JHH5, JHH7, and HUH7 cell lines and by 75% in the PLC/PRF/5 cell line; addition of a control antibody had no effect on basal c-Fos expression (FIG. 4C). These results demonstrate the ability of LD1 to inhibit the basal activity of FGFR4.

LD1 Inhibits Colony Formation.

Figure 4D:
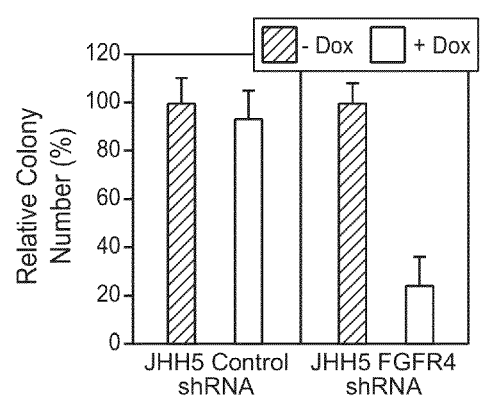

We first measured colony formation by JHH5 cells stably transfected with a doxycycline-inducible FGFR4 specific shRNA or a control shRNA. Although there was no difference in the ability of JHH5 cells transfected with the control construct to form colonies in the absence or presence of doxycycline, the addition of doxycycline to the JHH5 cells transfected with the FGFR4 shRNA construct inhibited colony formation by 76% as compared to cells in the absence of doxycycline (FIG. 4D). This result suggests that FGFR4 is involved in the colony formation of liver cancer cell lines.

Figure 4E:
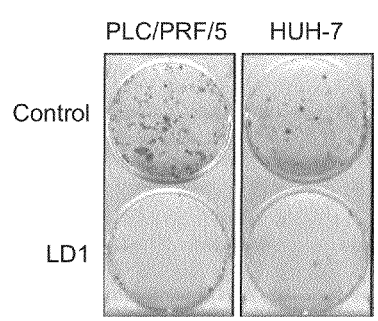
Figure 4F:
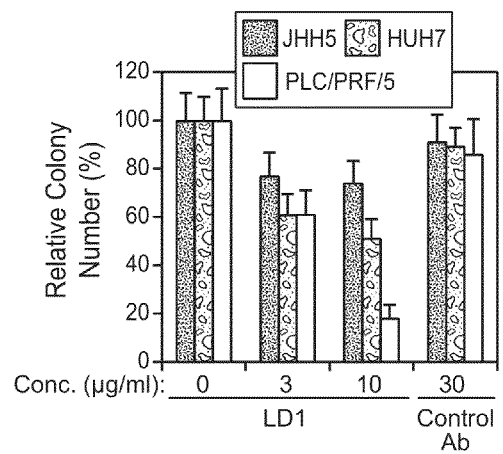

Next we tested the ability of LD1 to inhibit colony formation by a panel of liver cancer cell lines. The addition of LD1 to cultures of JHH5, HUH7, and PLC/PRF/5 cells caused a dose-dependent reduction in colony formation, reaching a maximum inhibition of 26%, 50%, and 82%, respectively (FIG. 4F). Representative examples of PLC/PRF/5 and HUH7 cell cultures are shown in FIG. 4E. The addition of a control antibody did not affect colony formation (FIGS. 4E and 4F). These results indicate that LD1 inhibits FGFR4-mediated colony formation in liver cancer cell lines.

LD1 Inhibits FGFR4 In Vivo Activity.

Figure 5A:
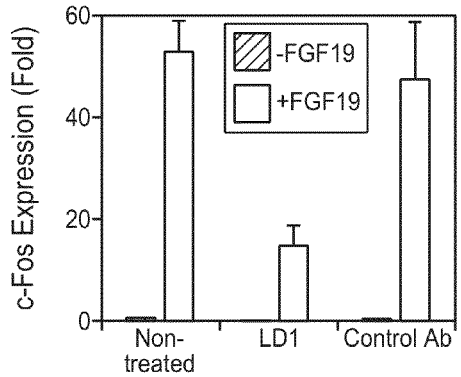
FIGS. 5A-5E: In vivo efficacy of LD1. A, LD1 inhibits FGF19-regulated c-Fos expression in mouse liver. The results are represented as fold expression relative to c-Fos levels in the livers of non-treated mice. B, LD1 (30 mg/kg; twice weekly) inhibits HUH7 xenograft tumor growth in vivo. C, Effects of LD1 on the mRNA expression of FGFR4, CYP7α1, c-Fos, and egr-1 in HUH-7 xenograft tumors from FIG. 5B. D, Multiple, large, raised tumors (arrows) protruding from the hepatic surface of a DEN-accelerated FGF19-TG:FGFR4-WT mouse treated with a control antibody (upper panel). Liver of DEN-accelerated FGF19-TG:FGFR4-WT mouse treated with LD1 (lower panel). E, Liver weights of DEN-accelerated FGF19-TG:FGFR4-WT mice treated with control antibody, LD1, or 1A6 (anti-FGF19 antibody).

We evaluated the in vivo efficacy of LD1 by measuring the FGF19-triggered c-Fos induction in the livers of mice injected with LD1 or a control antibody. We chose to monitor the c-Fos response to FGF19 because c-Fos induction in the liver is sensitive to FGF19 stimulation (16). C-Fos expression was 53-fold higher in the livers of mice treated with FGF19 compared with livers of mice treated with phosphate buffered saline (PBS) (FIG. 5A). The administration of LD1 18 hours prior to the injection of FGF19 reduced the c-Fos induction by 3.5-fold (FIG. 5A). LD1 also reduced the basal level of c-Fos expression in naïve mice by 6-fold (FIG. 5A). The injection of a control antibody did not alter the basal or the FGF19-stimulated expression of c-Fos compared to the non-treated mice (FIG. 5A). These data demonstrate the in vivo efficacy of LD1 at inhibiting the basal and the FGF19-stimulated FGFR4 activity.

LD1 Inhibits Tumor Growth In Vivo.

Figure 5B:
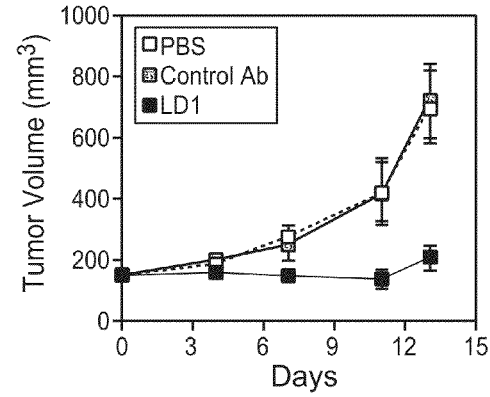
Figure 5C:
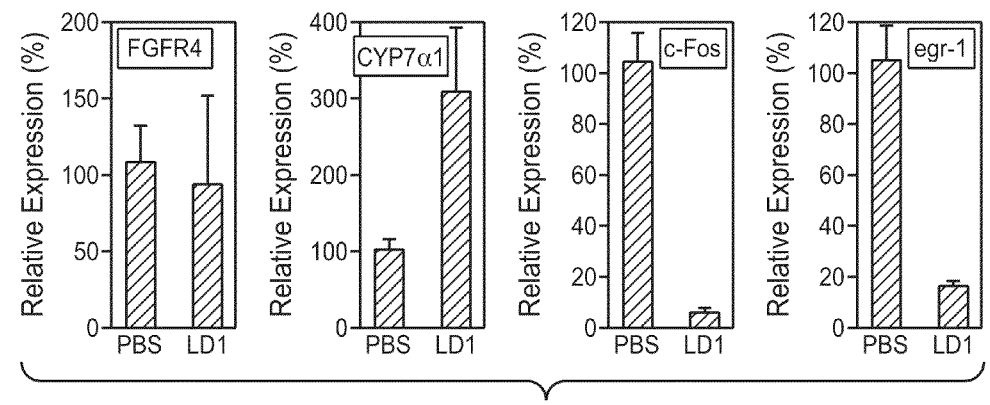
Figure 9:
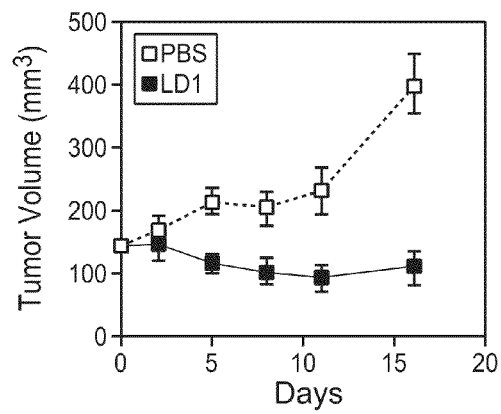
FIG. 9: In vivo efficacy of LD1. LD1 (30 mg/kg) inhibits HUH7 xenograft tumor growth in vivo. The anti-tumor efficacy of LD1 was evaluated in a biweekly modality.

To examine the in vivo efficacy of LD1 at inhibiting tumor growth we first utilized the HUH7 liver cancer cell line xenograft model. Mice bearing established tumors (approximately 150 mm$^3$) were dosed weekly with 30 mg/kg LD1, 30 mg/kg control antibody, or PBS. After 13 days, the HUH7 tumors of mice treated with either PBS or control antibody grew to an average size of 720 mm$^3$ (FIG. 5B). However, the HUH7 tumors of mice treated with LD1 grew to an average size of 28 mm$^3$, a 96% inhibition of tumor growth as compared to control antibody or PBS (FIG. 5B). In a repeat experiment, the administration of 30 mg/kg of LD1 twice per week caused complete tumor growth inhibition (FIG. 9). At necropsy, the tumors were excised and the effect of LD1 on the expression of FGFR4 and FGFR4-regulated genes was evaluated. The administration of LD1 did not affect FGFR4 expression in HUH7 xenograft tumors (FIG. 5C). However, LD1 increased the expression of CYP7α1 by 3-fold compared to the level of expression of CYP7α1 measured in the tumors of PBS treated mice (FIG. 5C). LD1 also reduced the expression of c-Fos and egr-1 by 17- and 6-fold, respectively, compared to PBS-treated mice (FIG. 5C).

Figure 5D:
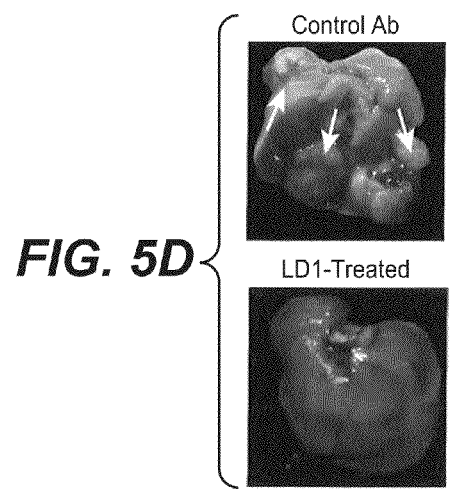
Figure 5E:
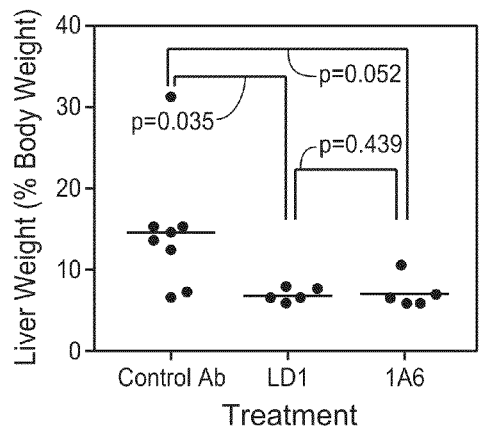

To further evaluate the in vivo efficacy of LD1 we used the FGF19-TG mouse model. FGF19-TG mice were treated with DEN at 15 days of age to accelerate tumorigenesis and then randomly grouped into 3 cohorts at 4 weeks of age. One group received a control antibody and the other two groups received either LD1 or an anti-FGF19 antibody (1A6) on a weekly basis. 1A6 was previously shown to prevent tumor formation in FGF19-TG mice (23). After 6 months the mice were necropsied and the livers were excised for analyses. The livers of mice treated with the control antibody had grossly evident large nodules on multiple lobes (FIG. 5D). However, the livers of mice treated with LD1 (FIG. 5D) or 1A6 had no evidence of neoplasia. We also measured liver weights to evaluate tumor burden because this parameter was previously shown to strongly correlate with percent tumor volume in the FGF19-TG model (18, 23). The weight of the livers from mice treated with LD1 or 1A6 was significantly (p=0.035 and p=0.052, respectively) lower than the weight of the livers from mice treated with control antibody (FIG. 5E). The difference in liver weight between mice treated with LD1 and the mice treated with 1A6 was not significant (p=0.439) (FIG. 5E). Together these data clearly demonstrate the in vivo efficacy of LD1 at inhibiting hepatocellular carcinoma in preclinical models.

FGFR4 Expression is Altered in Cancer.

Figure 6A:
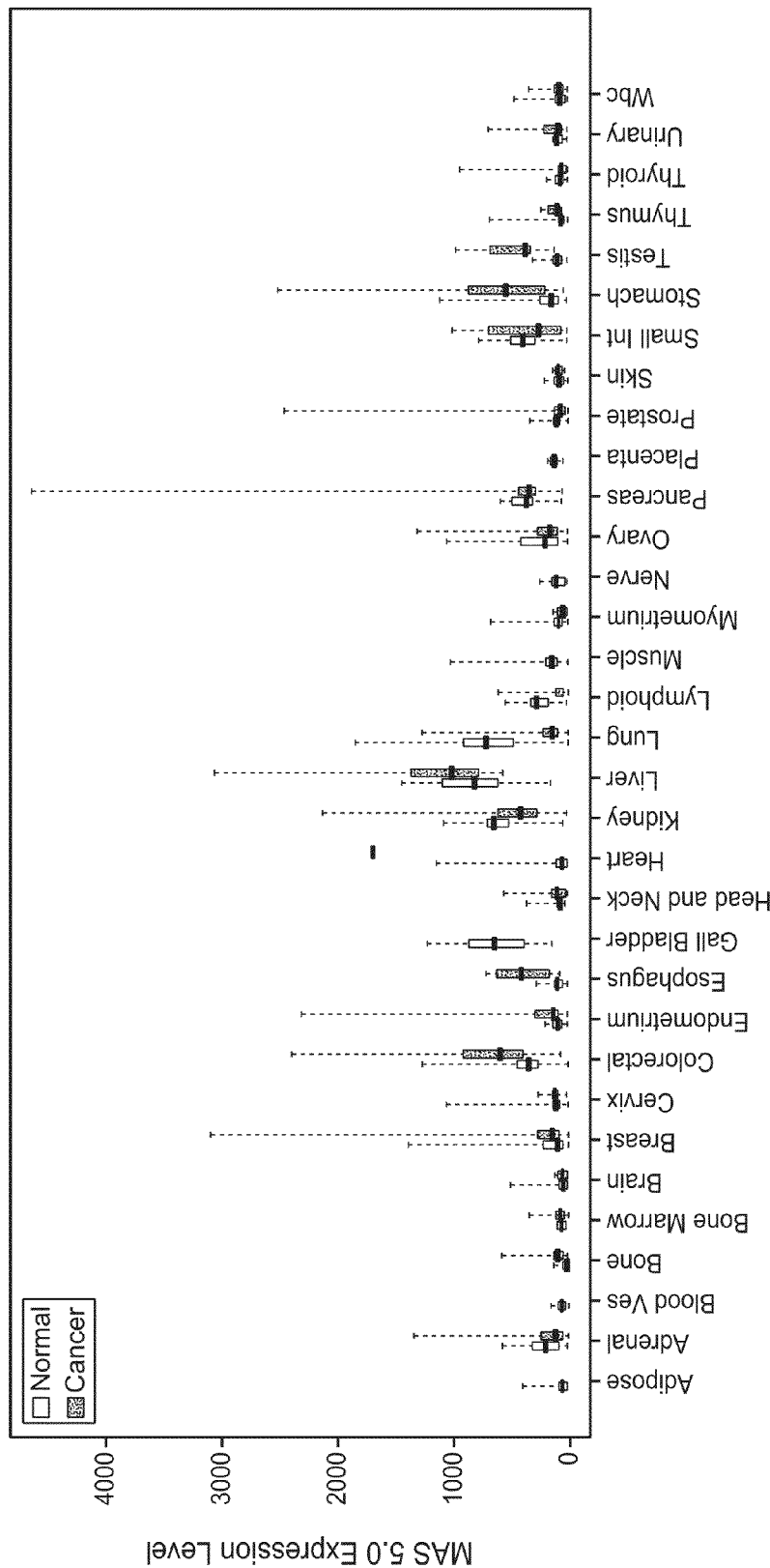
FIGS. 6A-6C: FGFR4 expression is deregulated in cancer. A, Whisker-box plots show FGFR4 expression in human tumors and normal tissues as determined by mRNA analysis of the BioExpress database. The center line indicates the median; the box represents the interquartile range between the first and third quartiles. "Whiskers" extend from the interquartile to the positions of extreme values. B, FGFR4 immunostaining in samples of breast (×100 magnification) and pancreas (×100 magnification) adenocarcinomas, and hepatocellular carcinoma (×200 magnification and ×400 magnification). C, FGFR4 mRNA expression in a panel of human normal liver and liver tumors as determined by qRT-PCR. The value for each sample is represented as fold expression relative to the level observed in sample N1.
Figure 6B:
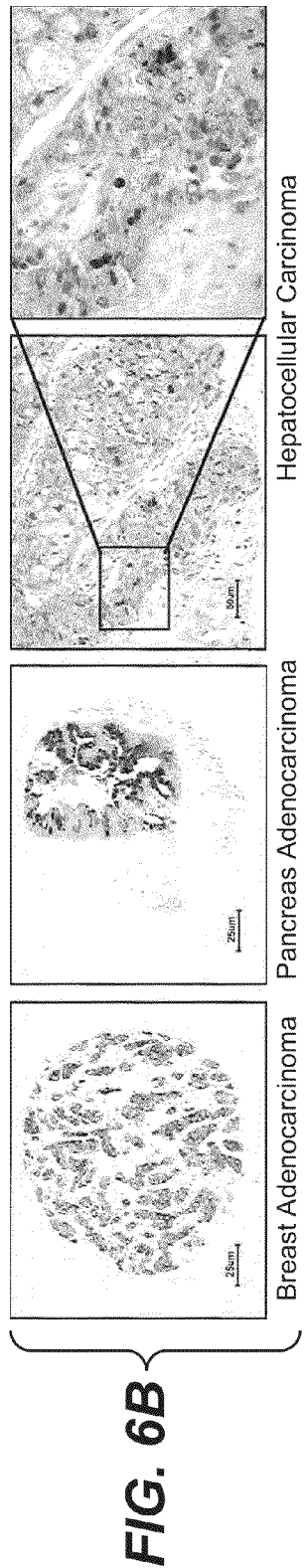

We evaluated FGFR4 expression in a variety of human normal and cancerous tissues by analyzing the BioExpress database (Gene Logic, Inc., Gaithersburg, Md., USA). FGFR4 expression is highly variable in most types of cancer. Compared to normal tissues, FGFR4 expression was elevated in liver, colorectal, stomach, esophageal, and testicular cancers, but diminished in kidney, lung, lymphoid, and small intestine cancers (FIG. 6A). Using immunohistochemistry (IHC) we localized FGFR4 in a panel of lung, breast, pancreas, and ovarian adenocarcinomas, lung squamous cell carcinoma, hepatocellular carcinoma, thyroid carcinoma, and normal lung, pancreas, and thyroid samples. The detection of FGFR4 gave rise to membranous and cytoplasmic staining in normal and neoplastic epithelial cells (representative examples are shown in FIG. 6B). Compared to normal tissues, higher grades of staining were generally found in tumor samples. Moderate to marked labeling by anti-FGFR4 was apparent in tumors from pancreas (in 41% of specimens), breast (46%), lung (31%), ovary (41%), colon (90%), liver (33%), and thyroid (11%) (Table 2 and ref. 23).

TABLE 2

FGFR4 expression in normal and cancer tissues. Prevalence of FGFR4 expression in normal and cancer tissues as determined by histopathological evaluation of FGFR4 immunostaining.

| | Number of Samples | Grades | | | |
|---|---|---|---|---|---|
| | | 0 | 1+ | 2+ | 3+ |
| Lung Adenocarcinoma | 29 | 7 (24%) | 13 (45%) | 7 (24%) | 2 (7%) |
| Lung Squamous Cell Carcinoma | 23 | 7 (30%) | 15 (65%) | 1 (4%) | 0 |
| Breast Adenocarcinoma | 63 | 1 (2%) | 33 (52%) | 25 (40%) | 4 (6%) |
| Thyroid carcinoma | 86 | 16 (19%) | 60 (70%) | 9 (10%) | 1 (1%) |
| Pancreatic Adenocarcinoma | 67 | 4 (6%) | 36 (54%) | 24 (36%) | 3 (5%) |
| Ovarian Adenocarcinoma | 80 | 9 (11%) | 38 (48%) | 26 (32%) | 7 (9%) |
| Normal lung | 4 | 3 (75%) | 1 (25%) | 0 | 0 |
| Normal Thyroid | 9 | 2 (22%) | 7 (78%) | 0 | 0 |
| Normal Pancreas | 23 | 2 (9%) | 17 (74%) | 3 (13%) | 1 (4%) |

Figure 6C:
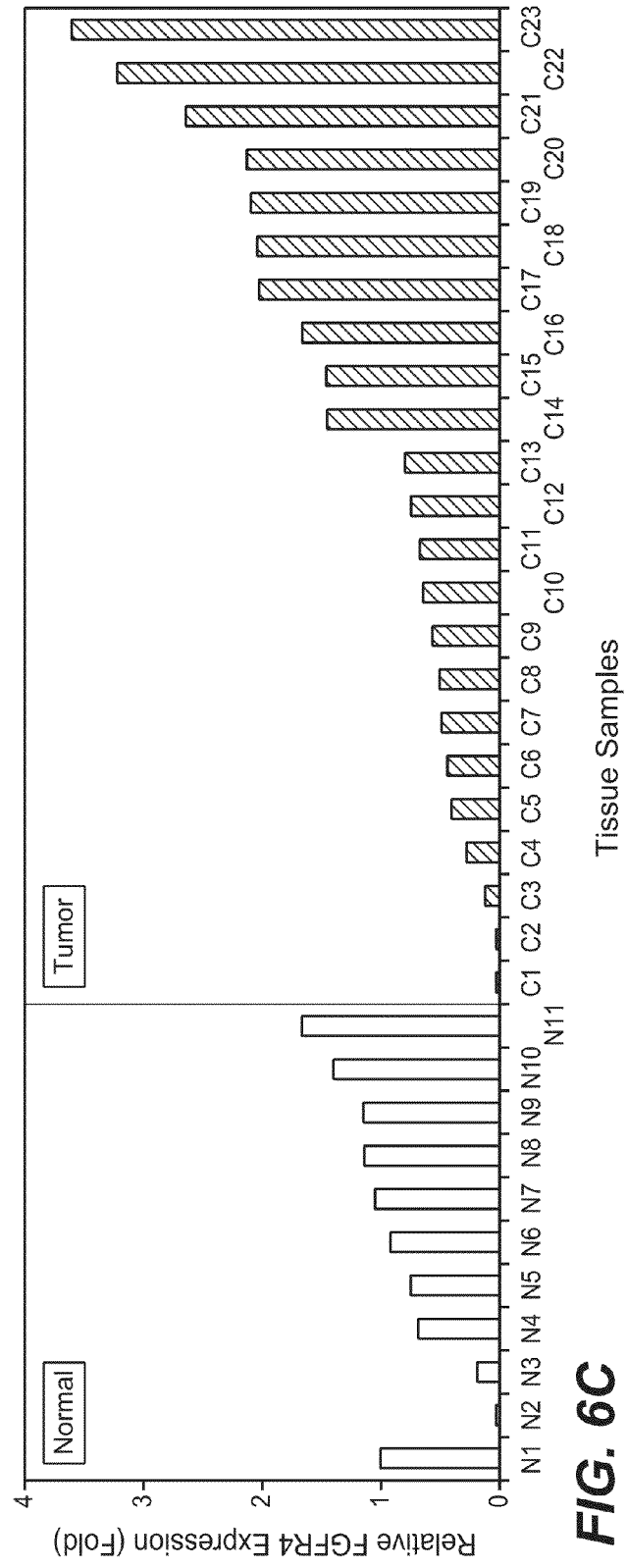

The widespread expression of FGFR4 in human HCC was also previously confirmed by in situ hybridization (23). Because a link between FGFR4 and HCC has already been suggested we decided to further evaluate FGFR4 expression in 23 primary human liver tumors and 11 normal livers using quantitative real-time polymerase chain reaction (qRT-PCR). The expression of FGFR4 in each sample was normalized to the expression of this receptor in the first normal liver sample (N1). The average level of FGFR4 was moderately increased in liver tumors (1.22-±0.05-fold) compared to normal livers (0.90-±0.04-fold), but the difference did not reach statistical significance (p=0.23) when that population was considered as a whole (FIG. 6C). However, FGFR4 expression was significantly higher (more than 2-fold) in a subset of tumors (7/23; 30%). These results illustrate that FGFR4 expression is deregulated in several types of cancer. The increased expression of FGFR4 in a subset of liver tumors suggests that it may represent an attractive target for the treatment of liver cancer in a diagnostic-selected patient population.

In this study, we provide evidence that FGFR4 participates in hepatocellular carcinoma and that treatment with an FGFR4 inactivating antibody can provide anti-tumor benefits. To evaluate the participation of FGFR4 in liver tumorigenesis we used genetically engineered mouse models. The exogenous expression of FGF19 was shown to promote hepatocyte proliferation, hepatocellular dysplasia, and the development of HCC in mice. In addition, we and others have demonstrated that Klotho β is required for the liver-specific activities of FGF19 (16, 19, 24). Because KLB and FGFR4 are most highly expressed in liver, we hypothesized that the deregulation of the FGFR4 pathway is responsible for the FGF19-mediated liver tumorigenesis. To test this hypothesis we bred FGF19-TG mice with FGFR4-KO mice. Preneoplastic hepatocellular proliferation and hepatocellular neoplasia were found only in FGF19-TG mice with an FGFR4-WT background. The liver tumorigenesis was abrogated in the FGFR4-KO mice. We further challenged the mice by administering a potent hepatocarcinogen, diethylnitrosamine. Treatment with DEN accelerated the development of HCC in FGF19-TG mice with an FGFR4-WT background, whereas no evidence of liver neoplasia was found in the FGFR4-KO mice. The clear conclusion is that FGFR4 is required for FGF19-promoted liver tumorigenesis.

Together these data suggest a link between FGFR4, liver tumorigenesis, and liver cancer progression. Consequently, FGFR4 is a potential therapeutic target and its inhibition may provide a therapeutic benefit to liver cancer patients. To this end we developed an anti-FGFR4 neutralizing antibody (LD1). LD1 binds to FGFR4 and inhibits ligand binding, pathway activation, regulation of gene expression, cell proliferation, and colony formation in vitro. The site at which LD1 binds to FGFR4 was localized by evaluating the interaction of LD1 with FGFR4 constructs bearing point mutations at sites that are similar between the FGFR4 orthologs but dissimilar in the FGFR1-3 orthologs; these amino acid residues in FGFR4 were substituted with the amino acid residues present at the equivalent positions in FGFR3. LD1 bound to wild type FGFR4 and all of the mutant FGFR4 constructs with the exception of the G165A mutant. The replacement of a glycine by an alanine at position 165 of FGFR4 nearly abolished LD1 binding. The exquisite specificity of LD1 for FGFR4 combined with the high identity of this region between FGFRs emphasizes the importance of this residue for LD1 binding. Glycine 165 in FGFR4 corresponds to alanine 171 in FGFR1. Interestingly, alanine 171 is the residue at the closest approach in the FGFR1 dimer interface (25). Across the axis of the dimer, the side chain of alanine 171 of one receptor makes a hydrophobic contact with alanine 171 of the adjacent receptor. The sequence conservation in this region of the FGFRs is consistent with this region forming a receptor-receptor interface (25). Thus, the binding of LD1 to this equivalent region of FGFR is likely disrupting receptor dimerization. Ligand-induced receptor dimerization is essential for the activation of FGFRs (26, 27). Therefore, inhibition of FGFR4 dimerization is a potential mechanism of action for LD1. A similar mechanism of action has already been described for other therapeutic antibodies (28).

We showed that in vivo, LD1 acts on liver cancer xenograft tumors by inhibiting the modulation of genes downstream from FGFR4 and by blocking tumor growth. In addition, the administration of LD1 inhibited the formation and development of HCCs in FGF19-TG mice.

These data demonstrate that FGFR4 is involved in promoting tumorigenesis and cancer progression. In particular, our results suggest that FGFR4 may play an important role in hepatocellular carcinoma. Several lines of evidence support this hypothesis. FGFR4 is the predominant FGFR isoform present in human hepatocytes (15). We have previously reported that liver tissue has the highest FGFR4 and KLB transcript levels, both of which are essential for ligand-stimulated activity by this signaling complex (16). Furthermore, ectopic expression of FGF19 (i.e. FGFR4-specific ligand) in mice promotes hepatocyte proliferation, hepatocellular dysplasia, and neoplasia (18) and FGF19-induced hepatocyte proliferation has been reported to be uniquely mediated by FGFR4 (24). A recent report suggests that FGFR4 also contributes significantly to HCC progression by modulating alpha-fetoprotein secretion, proliferation, and anti-apoptosis (17). FGFR4 expression has also been shown to promote resistance to chemotherapy (29). It should be noted that one group has reported a protective role, rather than an HCC promoting effect, for FGFR4 in mice (30). It is possible that contextual factors including the identity and concentration of ligand, as well as the levels of FGFRs and co-receptor expression might modulate the role of FGFR4 in tumorigenesis. For example, we found FGFR4 expression to be significantly increased in a subset of primary liver tumors, suggesting that FGFR4 may represent an attractive target for the treatment of liver cancer in a diagnostic-selected patient population. Given the accumulating evidence for the participation of FGFR4 in liver tumorigenesis and HCC progression, we believe that a therapeutic intervention that includes an anti-FGFR4 neutralizing antibody is likely to be beneficial in the treatment of liver cancer.

PARTIAL REFERENCE LIST

1. Ornitz, D. M., and Itoh, N. 2001. Fibroblast growth factors. Genome Biol 2:REVIEWS3005.
2. Eswarakumar, V. P., Lax, I., and Schlessinger, J. 2005. Cellular signaling by fibroblast growth factor receptors. Cytokine Growth Factor Rev 16:139-149.
3. Powers, C. J., McLeskey, S. W., and Wellstein, A. 2000. Fibroblast growth factors, their receptors and signaling. Endocr Relat Cancer 7:165-197.
4. Bange, J., Prechtl, D., Cheburkin, Y., Specht, K., Harbeck, N., Schmitt, M., Knyazeva, T., Muller, S., Gartner, S., Sures, I., et al. 2002. Cancer progression and tumor cell motility are associated with the FGFR4Arg(388) allele. Cancer Res 62:840-847.
5. Cappellen, D., De Oliveira, C., Ricol, D., de Medina, S., Bourdin, J., Sastre-Garau, X., Chopin, D., Thiery, J. P., and Radvanyi, F. 1999. Frequent activating mutations of FGFR3 in human bladder and cervix carcinomas. Nat Genet. 23:18-20.
6. Chesi, M., Brents, L. A., Ely, S. A., Bais, C., Robbiani, D. F., Mesri, E. A., Kuehl, W. M., and Bergsagel, P. L. 2001. Activated fibroblast growth factor receptor 3 is an oncogene that contributes to tumor progression in multiple myeloma. Blood 97:729-736.
7. Chesi, M., Nardini, E., Brents, L. A., Schrock, E., Ried, T., Kuehl, W. M., and Bergsagel, P. L. 1997. Frequent translocation t(4; 14)(p16.3; q32.3) in multiple myeloma is associated with increased expression and activating mutations of fibroblast growth factor receptor 3. Nat Genet. 16:260-264.
8. Gowardhan, B., Douglas, D. A., Mathers, M. E., McKie, A. B., McCracken, S. R., Robson, C. N., and Leung, H. Y. 2005. Evaluation of the fibroblast growth factor system as a potential target for therapy in human prostate cancer. Br J Cancer 92:320-327.
9. Jaakkola, S., Salmikangas, P., Nylund, S., Partanen, J., Armstrong, E., Pyrhonen, S., Lehtovirta, P., and Nevanlinna, H. 1993. Amplification of fgfr4 gene in human breast and gynecological cancers. Int J Cancer 54:378-382.
10. Jang, J. H., Shin, K. H., and Park, J. G. 2001. Mutations in fibroblast growth factor receptor 2 and fibroblast growth factor receptor 3 genes associated with human gastric and colorectal cancers. Cancer Res 61:3541-3543.
11. Jang, J. H., Shin, K. H., Park, Y. J., Lee, R. J., McKeehan, W. L., and Park, J. G. 2000. Novel transcripts of fibroblast growth factor receptor 3 reveal aberrant splicing and activation of cryptic splice sequences in colorectal cancer. Cancer Res 60:4049-4052.
12. Jeffers, M., LaRochelle, W. J., and Lichenstein, H. S. 2002. Fibroblast growth factors in cancer: therapeutic possibilities. Expert Opin Ther Targets 6:469-482.
13. Xiao, S., Nalabolu, S. R., Aster, J. C., Ma, J., Abruzzo, L., Jaffe, E. S., Stone, R., Weissman, S. M., Hudson, T. J., and Fletcher, J. A. 1998. FGFR1 is fused with a novel zinc-finger gene, ZNF198, in the t(8; 13) leukaemia/lymphoma syndrome. Nat Genet. 18:84-87.
14. Shariff, M. I., Cox, I. J., Gomaa, A. I., Khan, S. A., Gedroyc, W., and Taylor-Robinson, S. D. 2009. Hepatocellular carcinoma: current trends in worldwide epidemiology, risk factors, diagnosis and therapeutics. Expert Rev Gastroenterol Hepatol 3:353-367.
15. Kan, M., Wu, X., Wang, F., and McKeehan, W. L. 1999. Specificity for fibroblast growth factors determined by heparan sulfate in a binary complex with the receptor kinase. J Biol Chem 274:15947-15952.
16. Lin, B. C., Wang, M., Blackmore, C., and Desnoyers, L. R. 2007. Liver-specific activities of FGF19 require Klotho beta. J Biol Chem 282:27277-27284.
17. Ho, H. K., Pok, S., Streit, S., Ruhe, J. E., Hart, S., Lim, K. S., Loo, H. L., Aung, M. O., Lim, S. G., and Ullrich, A. 2009. Fibroblast growth factor receptor 4 regulates proliferation, anti-apoptosis and alpha-fetoprotein secretion during hepatocellular carcinoma progression and represents a potential target for therapeutic intervention. J Hepatol 50:118-127.
18. Nicholes, K., Guillet, S., Tomlinson, E., Hillan, K., Wright, B., Frantz, G. D., Pham, T. A., Dillard-Telm, L., Tsai, S. P., Stephan, J. P., et al. 2002. A mouse model of hepatocellular carcinoma:ectopic expression of fibroblast growth factor 19 in skeletal muscle of transgenic mice. Am Pathol 160:2295-2307.
19. Kurosu, H., Choi, M., Ogawa, Y., Dickson, A. S., Goetz, R., Eliseenkova, A. V., Mohammadi, M., Rosenblatt, K. P., Kliewer, S. A., and Kuro-o, M. 2007. Tissue-specific expression of betaKlotho and fibroblast growth factor (FGF) receptor isoforms determines metabolic activity of FGF19 and FGF21. J Biol Chem 282:26687-26695.
20. Pai, R., Dunlap, D., Qing, J., Mohtashemi, I., Hotzel, K., and French, D. M. 2008. Inhibition of fibroblast growth factor 19 reduces tumor growth by modulating beta-catenin signaling. Cancer Res 68:5086-5095.
21. Ornitz, D. M., Yayon, A., Flanagan, J. G., Svahn, C. M., Levi, E., and Leder, P. 1992. Heparin is required for cell-free binding of basic fibroblast growth factor to a soluble receptor and for mitogenesis in whole cells. Mol Cell Biol 12:240-247.
22. Holt, J. A., Luo, G., Billin, A. N., Bisi, J., McNeill, Y. Y., Kozarsky, K. F., Donahee, M., Wang da, Y., Mansfield, T. A., Kliewer, S. A., et al. 2003. Definition of a novel growth factor-dependent signal cascade for the suppression of bile acid biosynthesis. Genes Dev 17:1581-1591.
23. Desnoyers, L. R., Pai, R., Ferrando, R. E., Hotzel, K., Le, T., Ross, J., Carano, R., D'Souza, A., Qing, J., Mohtashemi, I., et al. 2008. Targeting FGF19 inhibits tumor growth in colon cancer xenograft and FGF19 transgenic hepatocellular carcinoma models. Oncogene 27:85-97.
24. Wu, X., Ge, H., Gupte, J., Weiszmann, J., Shimamoto, G., Stevens, J., Hawkins, N., Lemon, B., Shen, W., Xu, J., et al. 2007. Co-receptor requirements for fibroblast growth factor-19 signaling. J Biol Chem 282:29069-29072.
25. Plotnikov, A. N., Schlessinger, J., Hubbard, S. R., and Mohammadi, M. 1999. Structural basis for FGF receptor dimerization and activation. Cell 98:641-650.
26. Ibrahimi, O. A., Yeh, B. K., Eliseenkova, A. V., Zhang, F., Olsen, S. K., Igarashi, M., Aaronson, S. A., Linhardt, R. J., and Mohammadi, M. 2005. Analysis of mutations in fibroblast growth factor (FGF) and a pathogenic mutation in FGF receptor (FGFR) provides direct evidence for the symmetric two-end model for FGFR dimerization. Mol Cell Biol 25:671-684.
27. Mohammadi, M., Olsen, S. K., and Ibrahimi, O. A. 2005. Structural basis for fibroblast growth factor receptor activation. Cytokine Growth Factor Rev 16:107-137.
28. Agus, D. B., Akita, R. W., Fox, W. D., Lewis, G. D., Higgins, B., Pisacane, P. I., Lofgren, J. A., Tindell, C., Evans, D. P., Maiese, K., et al. 2002. Targeting ligand-activated ErbB2 signaling inhibits breast and prostate tumor growth. Cancer Cell 2:127-137.
29. Roidl, A., Berger, H. J., Kumar, S., Bange, J., Knyazev, P., and Ullrich, A. 2009. Resistance to chemotherapy is associated with fibroblast growth factor receptor 4 up-regulation. Clin Cancer Res 15:2058-2066.
30. Huang, X., Yang, C., Jin, C., Luo, Y., Wang, F., and McKeehan, W. L. 2009. Resident hepatocyte fibroblast growth factor receptor 4 limits hepatocarcinogenesis. Mol Carcinog 48:553-562.
31. Winer, J., Jung, C. K., Shackel, I., and Williams, P. M. 1999. Development and validation of real-time quantitative reverse transcriptase-polymerase chain reaction for monitoring gene expression in cardiac myocytes in vitro. Anal Biochem 270:41-49.
32. Tomlinson, E., Fu, L., John, L., Hultgren, B., Huang, X., Renz, M., Stephan, J. P., Tsai, S. P., Powell-Braxton, L., French, D., et al. 2002. Transgenic mice expressing human fibroblast growth factor-19 display increased metabolic rate and decreased adiposity. Endocrinology 143:1741-1747.
33. Yu, C., Wang, F., Kan, M., Jin, C., Jones, R. B., Weinstein, M., Deng, C. X., and McKeehan, W. L. 2000. Elevated cholesterol metabolism and bile acid synthesis in mice lacking membrane tyrosine kinase receptor FGFR4. J Biol Chem 275:15482-15489.

B. Highly Specific Off-Target Binding Identified and Eliminated During the Humanization of an Antibody Against FGF Receptor 4

Materials and Methods

FGFR4 was biotinylated using Sulfo-NHS-LC-biotin (Pierce; cat 21335).

Generation of Chimeric LD1

As described herein, the extracellular domain of human FGF receptor 4 (FGFR4), expressed in CHO cells and purified as described[14] was used to immunize balb/c mice. A hybridoma expressing LD1 was identified when clones were screened for the ability to block FGF19 binding to FGFR4 in a protein-based ELISA.

The murine LD1 variable domains were cloned from total RNA extracted from LD1 producing hybridoma cells using standard methods. The variable light (VL) and variable heavy (VH) domains were amplified using RT-PCR with degenerate reverse primers to the constant light (CL) and constant heavy domain 1 (CH1) and forward primers specific for the N-terminal amino acid sequence of the VL and VH regions. These variable domains were then cloned in-frame into vectors that contained the respective human light and heavy chain constant regions.

Humanization and Affinity Maturation of LD1

Hypervariable regions of LD1 were grafted into the human kappa I (huKI) and human VH subgroup III (huIII) variable domain frameworks used in trastuzumab. Framework repair was used to optimize FGFR4 binding affinity through the addition of mouse vernier position until a minimum combination of framework changes was identified that fully restored FGFR4 binding affinity[33].

hLD1.vB, displayed as a monovalent Fab-P3 fusion on phage, was affinity matured using a soft randomization strategy. Sequence diversity was introduced separately into each hypervariable region such that a bias towards the murine hypervariable region sequence was maintained using a poisoned oligonucleotide synthesis strategy[34]. For each diversified position, the codon encoding the wild-type amino acid was poisoned with a 70-10-10-10 mixture of nucleotides resulting in an average 50 percent mutation rate at each position.

The hLD1.vB diversified phage libraries were panned using a soluble selection method[35]. This approach relied upon a short binding period with low concentrations of biotinylated FGFR4 in solution, followed by a short 5 min capture of phage-bound to FGFR4 on immobilized neutravidin. Excess unlabeled FGFR4 (greater than 100 nM) was added prior to the capture step for increased off-rate selection stringency. Bound phage were eluted by incubating the wells with 100 mM HCl for 30 min, neutralized with 1 M Tris, pH 8 and amplified using XL1-Blue cells and M13/KO7 helper phage. Phage antibodies were reformatted into full-length IgG, transiently expressed in mammalian cells and purified by Protein A chromatography.

Affinity Determinations

Affinity determinations were performed by surface plasmon resonance using a BIAcore™-2000. Approximately 50 RU of hLD1.vB IgG was immobilized in 10 mM Sodium Acetate pH 4.8 on a CM5 sensor chip and serial 2-fold dilutions of the FGFR4 (0.48-1000 nM) in PBST were injected at a flow rate of 30 µl/min. Each sample was analyzed with 4-minute association and 10-minute dissociation. After each injection the chip was regenerated using 10 mM glycine pH 1.7. Binding response was corrected by subtracting the RU from a flow cell with an irrelevant IgG immobilized at similar density. A 1:1 Languir model of simultaneous fitting of kon and koff was used for kinetics analysis.

Xenograft Experiments

All animal protocols were approved by Genentech's Institutional Animal Care and Use Committee. Female nu/nu (nude-CRL) mice at seven weeks of age were obtained from Charles River Laboratories International (strain code 088). Mice were maintained under specific pathogen-free conditions. HUH7 cells ($5 \times 10^6$; Japan Health science Research Resources Bank, cat JCRB0403) were implanted subcutaneously into the flank of mice in a volume of 0.2 mL in HBSS/Matrigel (1:1 v/v; BD Biosciences, cat 354234). Tumors were measured twice weekly with a caliper and tumor volume was calculated using the formula: $V=0.5 \times L \times W^2$, where L and W are the length and width of the tumor, respectively. When the mean tumor volume reached 145 mm$^3$, mice were randomized into groups (n=15) and treated once weekly with 0.2 mL intraperitoneal injections of vehicle (PBS), 30 mg/kg chLD1, 30 mg/kg hLD1.vB, or 30 mg/kg hLD1.v22. Following treatment, tumor volumes were measured as described above. Percent tumor growth inhibition (% TGI) was calculated using the following formula, in which C=the mean tumor volume on Day 21 of the control vehicle group and T=the mean volume on Day 21 from each group of mice given the test treatment: % TGI=$100 \times ((C-T)/C)$. Data were analyzed and log-rank tests were used to evaluate tumor doubling differences between groups with JMP software, Version 6.0 (SAS Institute; Cary, N.C.). Data are presented as the mean tumor volume±SEM.

Pharmacokinetic Studies in Mice

NCR nude mice were supplied by Taconic (cat NCRNU). C3 knock-out mice[36] were back-crossed to C57BL/6 mice for at least 10 generations. Offspring were intercrossed to produce C3 knock-out mice and wild-type controls. In this study, they are referred to as C3 ko and C3 wt mice, respectively.

Mice weighing between 15.5 and 38.3 g were administered a 1, 5 or 20 mg/kg body weight IV bolus dose of anti-FGFR4 antibody via the tail vein. Blood samples were collected via retro orbital bleed or cardiac stick (n=3 mice per time point) and serum isolated at selected time points up to 28 day post dose. Serum samples were stored at −80° C. until assayed for anti-FGFR4 antibody serum concentrations using an ELISA.

Anti-FGFR4 antibody serum concentration-time profiles were used to estimate PK parameters using WinNonlin Enterprise Version 5.2.1 (Pharsight Corp.,). Since a single concentration-time profile was determined for each group, one estimate of each PK parameter was obtained and is reported, along with the standard error (SE) of the fit of each PK parameter. The nominal dose administered for each group was used for modeling.

Radioiodinations

Antibodies were radioiodinated using an indirect iodogen addition method[37]. The radiolabeled proteins were purified using NAPS™ columns (GE Healthcare Life Sciences, cat. 17-0853-01) pre-equilibrated in PBS. The specific activities of molecules used in the in vitro studies were 14.38 µCi/µg for chLD1 and 15.05 µCi/µg for hLD1.vB. The specific activities of molecules used in the in vivo study were 12.52 µCi/µg for chLD1 and 9.99 µCi/µg for hLD1.vB. Following radioiodination, the radioiodinated antibodies were characterized by size-exclusion high-performance liquid chromatography (HPLC), sodium dodecyl sulfate polyacrylamide gel electrophoresis (SDS-PAGE), and ELISA as intact and retaining comparable antigen binding to the unlabeled antibodies.

In Vitro Incubations

For incubations in serum, antibodies were added to NCR nude, C3 ko or C3 wt mouse serum[36], and PBS+0.5% BSA at a final concentration of 200 µg/ml. Aliquots (100 µl) were made and incubated at 37° C. with gentle rotation. The samples were transferred to dry ice at 0, 4, 8, 24, 48, and 96 h and stored at −70° C. until ELISA analysis.

For incubations in plasma, antibodies were added to cynomolgus monkey, human, rat (Bioreclamation LLC, cat. CYN-PLLIHP, HMLLIHP, and RATPLLIHP, respectively), and NCR nude mouse plasma (Taconic, cat NCRNU-E) and PBS+0.5% BSA at a final concentration of 200 µg/ml±$^{125}$I-antibodies at a final concentration of $5 \times 10^6$ CPM/ml. Aliquots (100 µl) were made and incubated at 37° C. with gentle rotation. At 0, 24, and 48 h the samples were transferred to dry ice and stored at −70° C. until analysis by size-exclusion HPLC ($^{125}$I-antibody+unlabeled antibody samples) or subjected to protein-G extraction followed by SDS-PAGE (unlabeled antibody samples).

Tissue Distribution Study

Female NCR nude mice received an IV bolus dose of $^{125}$I-chLD1 at 300 µCi/kg±unlabeled chLD1 at 20 mg/kg or $^{125}$I-hLD1.vB at 300 µCi/kg±unlabeled hLD1.vB at 20 mg/kg. Blood was collected at 15 minutes and 2, 5, 24, 72, and 120 h post-dose and processed for serum. The serum was frozen at −70° C. until analyzed by size-exclusion HPLC and subjected to protein-G extraction followed by SDS-PAGE separation. Total radioactive counts were also obtained using a Wallac 1480 Wizard 3" (EC&G Wallac, cat. 1480-011). Liver, lungs, kidneys, and heart were collected at 2, 72, and 120 hours post-dose and frozen at −70° C. until analysis for total radioactivity. All animals were handled in accordance with IACUC guidelines.

IgG and FGFR4 ELISA

FGFR4 specific IgG was measured using the FGFR4 ELISA. FGFR4 was immobilized on microtiter plates, LD1 standard (chLD1, hLD1.vB, or hLD1.v22) and samples diluted in Magic Buffer+0.35M NaCl (1×PBS pH 7.4, 0.5% BSA, 0.05% Tween-20, 0.25% Chaps, 5 mM EDTA, 0.2% BgG, 0.35M NaCl, 15 ppm Proclin) were added and capture IgG was detected with a F(ab')$_2$ goat anti-huIgG Fc conjugated to horseradish peroxidase (HRP, Jackson, cat#109-036-098).

Total antibody was determined using the Human Fc ELISA by incubating diluted samples on microtiter plates coated with F(ab')$_2$ rabbit anti-huIgG Fc (Jackson, cat#309-006-008) and detected with F(ab')$_2$ goat anti-huIgG Fc conjugated to HRP (Jackson, cat#109-036-098). TMB peroxidase substrate solution was used for color development (Moss, cat#TMBE-1000) and 1M H$_3$PO$_4$ was added to stop the reaction. Plates were read on a microplate reader (Biotek EL311 or equivalent) at 450/620 nm.

Size-Exclusion HPLC

Size-exclusion HPLC was performed in PBS using a Phenomenex™ BioSep-SEC-S 3000 column (300×7.8 mm, 5 µm column (Torrance, cat. 00H-2146-KO) with samples starting at pH 4.0 and pH 7.0. Samples at pH 7.0 were diluted in PBS; samples at pH 4.0 were generated by lowering the pH with 200 mM Citric Acid, pH 3.0. The flow rate was 0.5 ml/min for 30 minutes, isocratic. The ChemStation analog-to-digital converter was set to 25,000 units/mV, peak width 2 seconds, slit 4 nM (Agilent Technologies; cat 35900E). Radioactivity was detected with a raytest Ramona 90 (raytest USA Inc.; Wilmington, N.C.) in line with a standard Agilent 1100 HPLC module system (Santa Clara, Calif.).

Protein-G Bead Extraction and SDS-PAGE Separation

Triton X-100 (final concentration of 1% (v/v)) was added to fractions collected from the size-exclusion HPLC followed by the addition of Protein-G beads (GE Lifesciences Inc, cat. 17-0885-01). Samples were incubated overnight at 4° C. with gentle rotation and then the beads were washed four times with PBS+1% Triton X-100. Each sample was split and half of the sample was reduced using NuPage® Sample Reducing Agen (cat. NP0004)t. Beads were treated with NuPAGE® 4×LDS Sample Buffer (pH 8.4) (cat. NP00007)±NuPAGE® Sample Reducing Agent and incubated at 99° C. for 5 min; then applied to NuPAGE® 4-12% Bis-Tris gels (cat. NP0321BOX) with NuPAGE® 1×MOPS SDS Running buffer (cat. NP0001). Gels were stained with Coomassie Blue R250 dye. All NuPAGE® reagents were obtained from Invitrogen, Corp.

Mass Spectrometric and Bioinformatics Analysis

Samples excised from SDS-PAGE were treated as previously described[38]. Briefly, following rapid in-solution microwave-assisted tryptic digestion peptides were separated by reverse phase chromatography and eluted directly into a nanospray ionization source with a spray voltage of 2 kV and were analyzed using an LTQ XL-Orbitrap mass spectrometer (ThermoFisher). Precursor ions were analyzed in the FTMS at 60,000 resolution. MS/MS was performed in the LTQ with the instrument operated in data dependent mode whereby the top 10 most abundant ions were subjected for fragmentation. Data was searched using the Mascot Search Algorithm (Matrix Sciences) or by de novo interpretation.

For searching Mascot data: Search criteria included a full MS tolerance of 20 ppm, MS/MS tolerance of 0.5 Da with GlyGly on Lys, Oxidation of Methionine, +57 Da on Cys and Phosphorylation of ST and Y as variable modifications with up to 3 mis-cleavages. Data was searched against the Mammalian subset of the Swissprot database.

Results

Humanization and Characterization of LD1

Figure 10A:
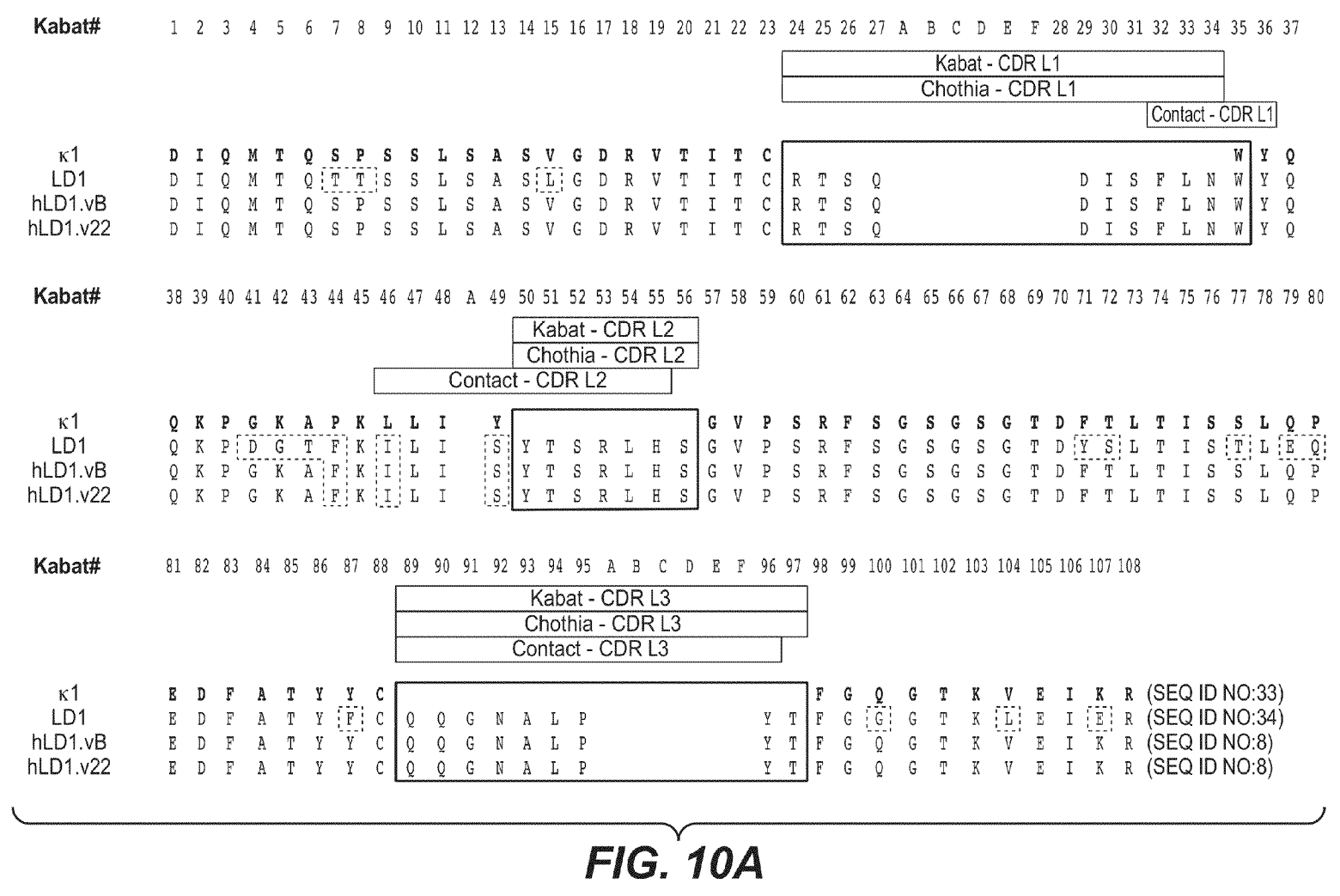

The human chimeric antibody LD1 (chLD1) has been shown to bind human FGFR4, block signaling by FGF19 and other FGF ligands and suppress tumor growth in a HUH7 human hepatocelluar carcinoma (HCC) xenograft model[14]. As a first step in the humanization of LD1, the variable light and heavy domains of chLD1 were aligned with the human kappa I (huKI) and human VH subgroup III (huIII) variable domain frameworks used in trastuzumab (FIG. 10). Hypervariable regions from chLD1 were grafted into these human variable frameworks to generate a direct CDR-graft (hLD1.vA)[15, 16]. When compared to chLD1 by surface plasmon resonance for binding FGFR4, the affinity of hLD1.vA was decreased by about 5-fold (not shown). Substitution of mouse sequence at various vernier positions in both the variable light and heavy domains was explored as a means to improve binding and led to the identification of three important mouse vernier positions in the LC: P44F, L46I and Y49S. These changes were incorporated in hLD1.vB that had an affinity for FGFR4 comparable to chLD1 (Table 3).

TABLE 3

Binding Kinetics of anti-FGFR4 antibody variants. The association and dissociation rates of human FGFR4 binding to immobilized antibody variants were measured using surface plasmon resonance.

| LD1 Ab | kd (nM) | kon (M · sec−1) | koff (sec−1) |
| --- | --- | --- | --- |
| chLD1 | 0.45 | 3.82e5 | 1.73e−4 |
| hLD1.vB | 0.97 | 2.88e5 | 2.80e−4 |
| hLD1.v22 | .043 | 9.10e5 | 3.90e−5 |

Figure 11A:
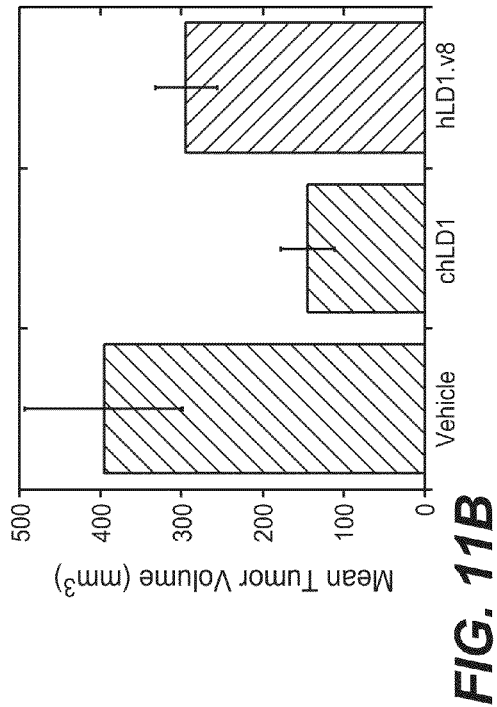
FIGS. 11A-11D: Pharmacokinetics and Distribution of anti-FGFR4 antibody variants. (A) Comparison of the binding of chLD1 and hLD1.vB to FGFR4 using the FGFR4 ELISA. (B) Comparison of day 16 tumor volumes of chLD1, hLD1.vB and vehicle in an HUH7 human hepatocelluar carcinoma xenograft model in CRL nu/nu mice. Antibodies were administered at 30 mg/kg twice weekly (10 mice per group). Only chLD1 was effective at reducing tumor growth relative to the PBS control (p value=0.014) while hLD1.vB was not significantly effective (p value=0.486). (C) Pharmacokinetics of chLD1 and hLD1.vBNCR nude mice were dosed at 1 or 20 mg/kg IV and samples were analyzed using the FGFR4 ELISA. Similar results were obtained using the IgG ELISA (not shown). (D) Tissue distribution of $^{125}$I-chLD1 and $^{125}$I-hLD1.vB in NCR nude mouse. Mice were dosed with either $^{125}$I-chLD1 or $^{125}$I-hLD1.vB and the percent of injected dose per gram of tissue (% ID/g) was determined at 2 hours post-dose as described in Methods.
Figure 11B:
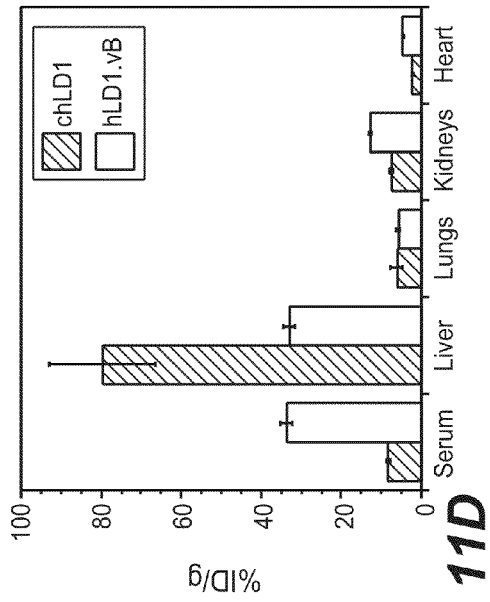

Surprisingly, despite similar FGFR4 binding affinity (FIG. 11A), hLD1.vB had diminished anti-tumor efficacy compared to chLD1 in the HUH7 human HCC xenograft model in nu/nu mouse (FIG. 11B). After 9 days, the HUH7 tumors of mice treated with PBS grew to an average volume of approximately 700 mm$^3$. In the chLD1 treated group, average HUH7 tumor volume was approximately 400 mm$^3$, representing a 43% inhibition of tumor growth compared to the tumor in the PBS-treated animals. However, the average tumor volume in mice treated with hLD1.vB was approximately 600 mm$^3$, representing a 14% inhibition of tumor growth compared to the tumor in the PBS-treated animals.

Figure 11C:
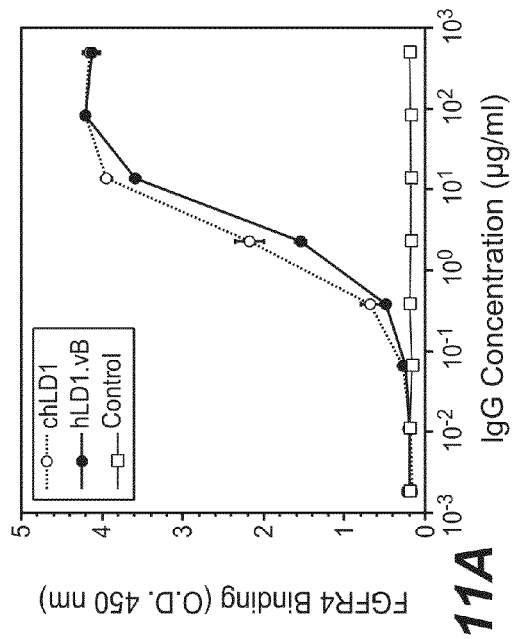

A pharmacokinetic evaluation of chLD1 and hLD1.vB conducted in athymic NCR nude mice revealed rapid clearance for both chLD1 and hLD1.vB at 1 mg/kg IV (140 and 132 mL/day/kg, respectively), suggesting a target mediated clearance mechanism. This clearance mechanism appeared to be saturated for chLD1 at a higher dose of 20 mg/kg. At this dose the observed clearance (11.7 mL/day/kg; FIG. 11C) was with in the range (6-12 mL/day/kg) of target-independent clearance observed for a typical humanized antibody in mouse (Ref 17 and P. Theil personal communication). However, hLD1.vB continued to be rapidly cleared (34.2 mL/day/kg; FIG. 11C). This suggested an additional clearance mechanism for hLD1.vB could be responsible for the apparent lack of efficacy in the mouse xenograft model.

Figure 11D:
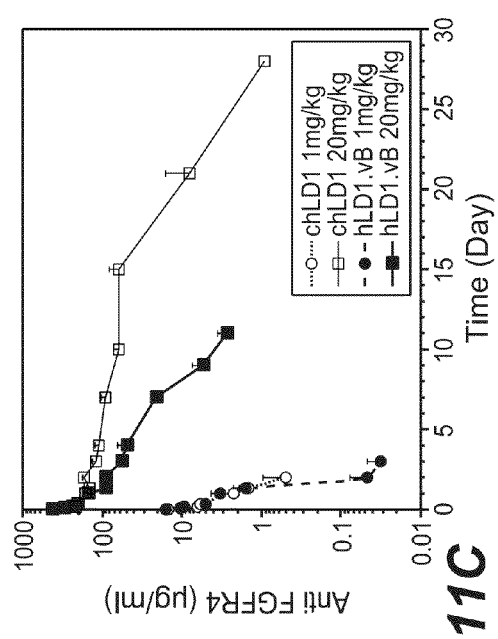

Consistent with the PK finding, a biodistribution study using $^{125}$I-chLD1 and $^{125}$I-hLD1.vB revealed significantly different distribution profiles (FIG. 11D). $^{125}$I-chLD1 distributed rapidly and specifically to the liver due to the high expression of FGFR4 on hepatocytes while only a limited amount of $^{125}$I-hLD1.vB was found in liver at an equivalent dose by 2 hours (~80 vs. 35% ID/g). In contrast, the observed distribution of these antibodies was reversed in blood suggesting that a competing interaction prevented distribution of hLD1.vB to the liver as opposed to a loss in antibody stability in vivo that would have led to a loss in overall radioactivity.

Identification of C3 Interference.

Figure 12A:
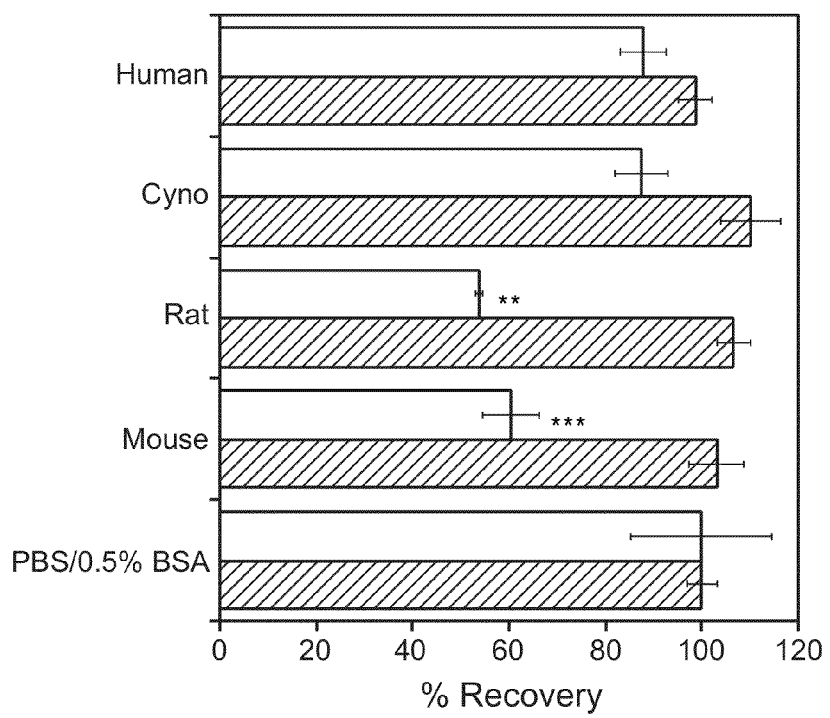
Figure 12B:
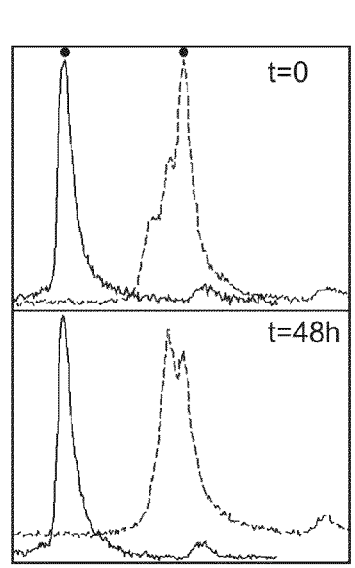

In an effort to reconcile the in vivo differences observed between chLD1 and hLD1.vB, we evaluated antibody stability in plasma as well as potential off-target plasma or tissue interactions that might affect their function. Plasma stability was evaluated by incubating chLD1 or hLD1.vB in mouse, rat, monkey or human plasma for 48 hours at 37° C. followed by an assessment of both the FGFR4 binding activity and the total human IgG concentration. While the total chLD1 or hLD1.vB concentration as measured by the IgG ELISA did not change (not shown), the recovery of hLD1.vB detected by the FGFR4 ELISA was significantly reduced (by ~30%) in mouse and rat plasma compared to a control incubation in PBS/BSA (FIG. 12A). In contrast, there was no loss of chLD1 FGFR4 binding activity in any condition tested. The significant reduction in hLD1.vB recovery, specifically from rodent plasma, suggested that the loss was not due to degradation, but more likely the formation of an interfering complex in rodent plasma. Since the interaction of hLD1.vB with mouse plasma might result in the generation of a higher molecular weight complex, iodinated chLD1 and hLD1.vB were also incubated in plasma and analyzed using size-exclusion HPLC. High molecular weight peaks were detected only in the mouse plasma samples containing $^{125}$I-hLD1.vB but not $^{125}$I-chLD1. In addition to the expected antibody peak at 150 kDa, peaks corresponding to ca. 270 and ca. 550 kDa were also detected initially (FIG. 12B), however by 48 h, only the 150 and 270 kDa peaks remained; the 550 kDa peak was no longer observed. These higher molecular weight peaks were not detected in cynomolgus monkey and human plasma or PBS/BSA containing hLD1.vB or in any sample containing chLD1 (FIG. 15). Interestingly, the presence of these high molecular weight peaks correlated directly with the antibody recovery data obtained in the FGFR4 ELISA. Further, the presence of these peaks was diminished when the analysis was performed at pH 4.0 (FIG. 15), further supporting the hLD1.vB dependent interaction with mouse serum.

Figure 12C:
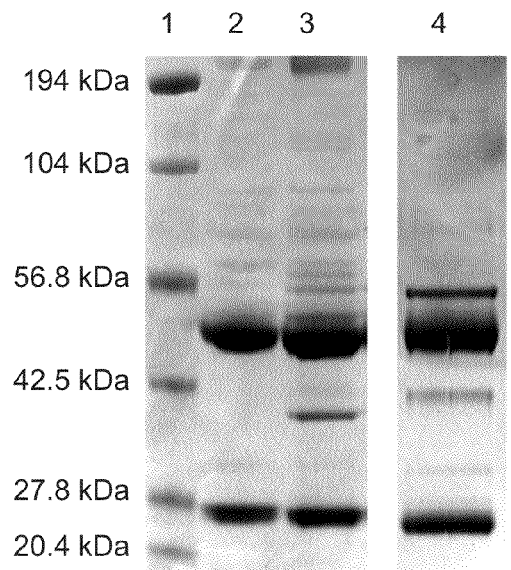
Figure 16A:
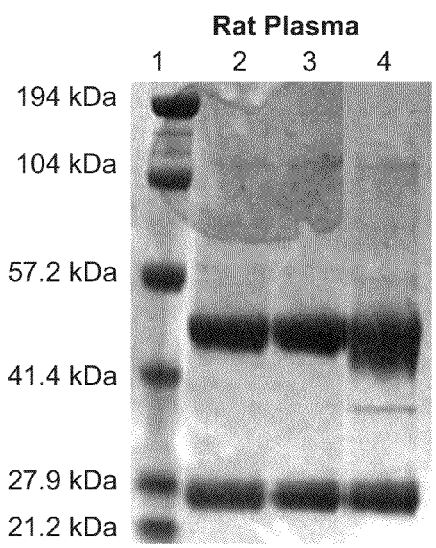
Figure 16B:
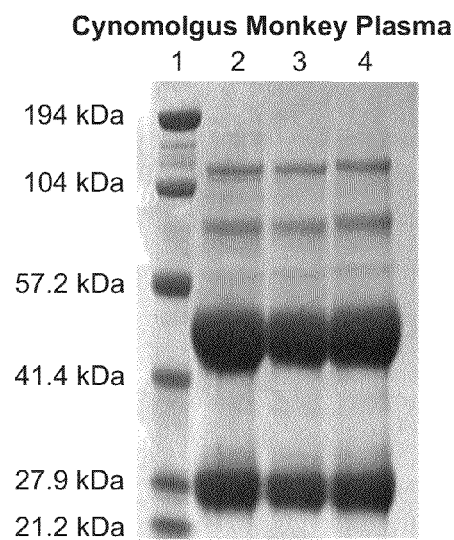
Figure 16C:
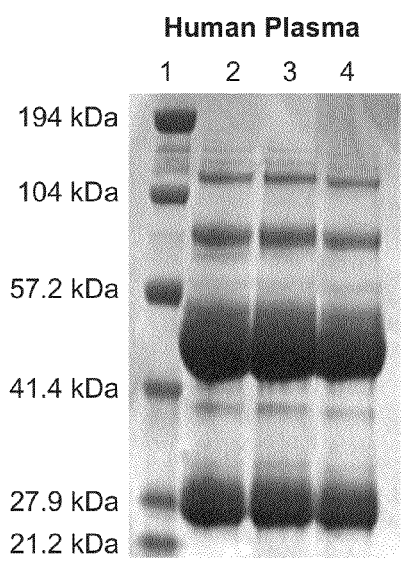
Figure 16D:
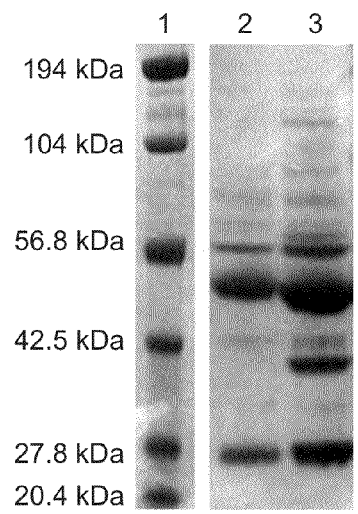

Immunoprecipitation of mouse plasma revealed a ca. 37 kDa protein that was selectively pulled down using hLD1.vB, but not chLD1 (FIG. 12C). Consistent with the findings from size-exclusion HPLC, this 37 kDa protein band was observed in rat but not cynomolgus monkey and human plasma samples (FIG. 16A-C). Furthermore, the protein was detected in the plasma from mice dosed with hLD1.vB (FIG. 16D). MS/MS analysis of tryptic peptides derived from the 37 kDa mouse plasma protein identified this band as being derived from mouse complement C3 (FIG. 12D). A direct involvement of C3 was supported by the full recovery of hLD1.vB incubated in plasma from C3 knock-out (ko) mice (FIG. 17).

Affinity Maturation and Re-Evaluation of C3 Binding.

Both chLD1 and hLD1.vB share the same human constant regions and complementary determining regions (CDRs) and thus differ only by their variable domain frameworks. Further, the light and heavy chain variable domain frameworks used to humanize hLD1.vB share a very high degree of homology with several humanized antibodies including trastuzumab that have not been reported to exhibit interactions with mouse serum proteins. Thus the off-target interaction of hLD1.vB with mouse C3 most likely resulted from the particular combination of the mouse LD1 CDRs with the human variable domain frameworks.

We reasoned that some of the changes in the CDR sequences of hLD1.vB, which resulted from affinity maturation of the Fab fragment displayed on phage, could lead to improved affinity for FGFR4 with a concomitant loss in mouse C3 binding. Phage selected variants were expressed as IgG and screened for FGFR4 binding affinity as well as for potential interaction with mouse C3 using an immunoprecipitation assay coupled with SDS-PAGE analysis. One variant, hLD1.v22, with 3 amino acid changes in CDR-H2 compared to hLD1.vB (H52L, S53V and D60E, FIG. 10), showed both improved binding affinity for FGFR4 (Table 3) and a loss of binding to complement C3 (FIG. 13B).

The degree to which mouse complement C3 altered the clearance of hLD1.vB and hLD1.v22 in vivo was assessed in a pharmacokinetic study comparing C3 ko mice to C3 wt mice at 20 mg/kg. As observed previously in NCR mice, hLD1.vB was rapidly cleared from circulation in C3 wt mice (29 mL/day/kg); however, both chLD1 and hLD1.vB had similar pharmacokinetic profiles (clearance of 8.7 and 9.3 mL/day/kg, respectively) in the C3 ko mice (FIG. 14A and Table 4).

TABLE 4

Pharmacokinetic parameters of anti-FGFR4 variants dosed at 20 mg/kg IV

| c | AUC (day*ug/mL) | Cmax (ug/mL) | CL (mL/day/kg) | Beta HL (day) | V1 (mL/kg) | Vss (mL/kg) |
| --- | --- | --- | --- | --- | --- | --- |
| chLD1 C3 ko | 2294 (203) | 483 (42) | 8.7 (0.77) | 7.1 (1) | 41 (3.6) | 86 (6.8) |
| hLD1.vB C3 ko | 2143 (161) | 530 (51) | 9.3 (0.70) | 5.9 (0.6) | 38 (3.6) | 78 (5.1) |
| chLD1 C3 wt | 2937 (325) | 489 (62) | 6.8 (0.76) | 7.9 (1.3) | 41 (5.2) | 76 (6.9) |
| hLD1.vB C3 wt | 688 (48) | 376 (30) | 29 (2.06) | 2.5 (0.3) | 53 (4.2) | 97 (8.8) |
| chLD1 NCR nude | 1696 (85) | 335 (21) | 11.8 (0.59) | 5.8 (0.4) | 60 (3.7) | 97 (4.5) |
| hLD1.vB NCR nude | 428 (22) | 256 (15) | 46.7 (2.46) | 2.3 (0.2) | 78 (4.6) | 139 (9.9) |
| hLD1.v22 NCR nude | 1777 (119) | 338 (24) | 11.3 (0.75) | 6.5 (0.6) | 59 (4.1) | 103 (5.6) |

These data are consistent with the tissue distribution data and confirm that specific interaction with mouse complement C3 in vivo leads to rapid clearance of hLD1.vB. Since the clearance of hLD1.vB is significantly improved in C3 ko mice and hLD1.v22 does not bind to C3, we anticipated that hLD1.v22 would have a pharmacokinetic profile similar to chLD1 in NCR nude mice. As shown in FIG. 14B, the clearance of chLD1 and hLD1.v22 are similar in NCR nude mice (11.8 and 11.3 mL/day/kg respectively) while consistent with our previous findings, hLD1.vB is rapidly cleared (46.7 mL/day/kg).

The ability of hLD1.v22 to inhibit tumor growth in the HUH7 HCC xenograft model was evaluated in comparison to chLD1 and hLD1.vB. After 21 days, the HUH7 tumors of mice treated with PBS grew to an average volume of approximately 2,100 mm$^3$ (FIG. 14C). Of the 15 animals in the PBS-treated group, three were euthanized before the end of study due to tumor volume limits (approximately 2,500 mm$^3$). In the hLD1.vB treated group, average HUH7 tumor volume was approximately 1,200 mm$^3$, representing a 43% inhibition of tumor growth compared to the tumor in the PBS-treated animals. However, the average tumor volume in mice treated with hLD1.v22 was approximately 530 mm$^3$. This result was comparable to the chLD1 treated mice where the average HUH7 tumor volume was approximately 350 mm$^3$. For both hLD1.v22 and chLD1 treated groups, this represents a 75% and 83% reduction in tumor size, respectively, compared to the PBS vehicle treatment group. The tumor doubling times of the groups treated with hLD1.vB (12.2 days), hLD1.v22 (15.8 days) or chLD1 (17.1 days) is significantly greater than that of the PBS-treated group (8.2 days). Additionally, the tumor doubling times of the hLD1.v22 or chLD1-treated groups were significantly longer than that for the hLD1.vB treated group. The similar in vivo performance of both hLD1.v22 and chLD1 compared to hLD1.vB, strongly implies that the specific off-target interaction with mouse complement C3 was causing the increased clearance resulting in lower exposure and reduced efficacy of hLD1.vB.

Thus, the generation of anti-FGFR4 antibody hLD1.v22 had the following steps: 1) the generation of a human chimeric LD1 (chLD1) containing the murine VL and VH domains of LD1 and the human IgG1 constant domain; 2) the graft of the 6 murine HVRs from chLD1 to human VL kappa I and human VH subgroup III variable domain frameworks, creating a direct-HCR graft, generating antibody hLD1.vA. Antibody hLD1.vA bound FGFR4 about 5 fold less than ChLD1; 3) introduction of light chain mutations P44F, L46I and Y49S resulted in antibody hLD1.vB. Antibody hLD1.vB bound human FGFR4 with about two-fold more weakly than did antibody chLD1, but hLD1.vB had reduced tumor efficacy in vivo, rapid clearance in vivo compared with chLD1, and was found to bind mouse complement protein C3; 4) affinity maturation was performed, and the addition of three changes to HVR H2 (H52L, S53V, D60E) improved binding affinity to FGFR4 and eliminated binding to mouse complement c3 protein. The resulting humanized and affinity matured antibody, antibody hLD1.v22, had comparable in vivo efficacy, pK and tissue distribution to chLD1. Furthermore, antibody hLD1.v22, has been determined to have at least comparable biological activity as the parent chLD1 antibody, for example in inhibiting cancer in human xenograft tumor studies.

PARTIAL REFERENCE LIST

1. James L C, Roversi P, Tawfik D S. Antibody multispecificity mediated by conformational diversity. Science 2003; 299:1362-7.
2. Krishnan L, Sahni G, Kaur K J, Salunke D M. Role of antibody paratope conformational flexibility in the manifestation of molecular mimicry. Biophys J 2008; 94:1367-76.
3. Notkins A L. Polyreactivity of antibody molecules. Trends Immunol 2004; 25:174-9.
4. Thorpe I F, Brooks C L, 3rd. Molecular evolution of affinity and flexibility in the immune system. Proc Natl Acad Sci USA 2007; 104:8821-6.
5. Yin J, Beuscher A Et, Andryski S E, Stevens R C, Schultz P G. Structural plasticity and the evolution of antibody affinity and specificity. J Mol Biol 2003; 330:651-6.
6. Thielges M C, Zimmermann J, Yu W, Oda M, Romesberg F E. Exploring the energy landscape of antibody-antigen complexes: protein dynamics, flexibility, and molecular recognition. Biochemistry 2008; 47:7237-47.
7. Feyen O, Lueking A, Kowald A, Stephan C, Meyer H E, Gobel U, et al. Off-target activity of TNF-α inhibitors characterized by protein biochips. Analytical and Bioanalytical Chemistry 2008; 391:1713-20.
8. Kijanka G, Ipcho S, Baars S, Chen H, Hadley K, Beveridge A, et al. Rapid characterization of binding specificity and cross-reactivity of antibodies using recombinant human protein arrays. J Immunol Methods 2009; 340:132-7.
9. Lueking A, Beator J, Patz E, Mullner S, Mehes G, Amersdorfer P. Determination and validation of off-target activities of anti-C D44 variant 6 antibodies using protein biochips and tissue microarrays. Biotechniques 2008; 45:Pi-v.
10. Wu H, Pfarr D S, Johnson S, Brewah Y A, Woods R M, Patel N K, et al. Development of motavizumab, an ultrapotent antibody for the prevention of respiratory syncytial virus infection in the upper and lower respiratory tract. J Mol Biol 2007; 368:652-65.
11. Rosenwald S, Kafri R, Lancet D. Test of a statistical model for molecular recognition in biological repertoires. J Theor Biol 2002; 216:327-36.
12. James L C, Tawfik D S. The specificity of cross-reactivity: promiscuous antibody binding involves specific hydrogen bonds rather than nonspecific hydrophobic stickiness. Protein Sci 2003; 12:2183-93.
13. Kramer A, Keitel T, Winkler K, Stocklein W, Hohne W, Schneider-Mergener J. Molecular basis for the binding promiscuity of an anti-p24 (HIV-1) monoclonal antibody. Cell 1997; 91:799-809.
14. French D M, Lin B C, Wang M, Hötzel K, Bolon B, Ferrando R, et al. Targeting FGFR4 Inhibits Hepatocellular Carcinoma in Preclinical Animal Models. J Clin Invest 2011; Submitted.
15. Dennis M S. Humanization by CDR Repair In: Shire S, Gombotz W, Bechtold-Peters K, Andya J, eds. Pharmaceutical Aspects of Monoclonal Antibodies. New York: Co-published by the Association for Pharmaceutical Scientists & Springer, 2010:9-28.
16. MacCallum R M, Martin A C R, Thornton J T. Antibody-antigen interactions: Contact analysis and binding site topography. Journal of Molecular Biology 1996; 262:732-45.
17. Adams C W, Allison D E, Flagella K, Presta L, Clarke J, Dybdal N, et al. Humanization of a recombinant monoclonal antibody to produce a therapeutic HER dimerization inhibitor, pertuzumab. Cancer Immunol Immunother 2006; 55:717-27.
18. Kim S J, Park Y, Hong H J. Antibody engineering for the development of therapeutic antibodies. Mol Cells 2005; 20:17-29.
19. Lutz H U, Jelezarova E. Complement amplification revisited. Mol Immunol 2006; 43:2-12.
20. Sahu A, Lambris J D. Structure and biology of complement protein C3, a connecting link between innate and acquired immunity. Immunological Reviews 2001; 180:35-48.
21. Manderson A P, Pickering M C, Botto M, Walport M J, Parish C R. Continual low-level activation of the classical complement pathway. Journal of Experimental Medince 2001; 194:747-56.

22. Thurman J M, Holers V M. The central role of the alternative complement pathway in human disease. The Journal of Immunology 2006; 176:1305-10.
23. Sahu A, Pangburn M K. Covalent attachment of human complement C3 to IgG. The Journal of Biological Chemistry 1994; 269:28997-9002.
24. Vidarte L, Pastor C, Mas S, Blazquez A B, de los Rios V, Guerrero R, et al. Serine 132 is the C3 covalent attachment point on the C H1 domain of human IgG1. J Biol Chem 2001; 276:38217-23.
25. Osmers I, Szalai A J, Tenner A J, Barnum S R. Complement in BuB/BnJ mice revisited: serum C3 levels and complement opsonic activity are not elevated. Mol Immunol 2006; 43:1722-5.
26. Otte L, Knaute T, Schneider-Mergener J, Kramer A. Molecular basis for the binding polyspecificity of an anti-cholera toxin peptide 3 monoclonal antibody. J Mol Recognit 2006; 19:49-59.
27. Arenkov P, Kukhtin A, Gemmell A, Voloshchuck S, Chupeeva V, Mirzabekov A. Protein microchips: use for immunoassay and enzymatic reactions. Analytical Biochemistry 2000; 278:123-31.
28. Ge H. U P A, a universal protein array system for quantitative detected protein-protein, protein-DNA, protein-RNA, and protein-ligand interactions. Nucleic Acids Research 2000; 28:i-vii.
29. Fodor S P, Read J L, Pirrung M C, Stryer L, Lu A T, Solas D. Light-directed, spatially addressable parallel chemical synthesis. Science 1991; 251:767-73.
30. Forster R, Valin M, Lemarchand T, Palate B, Fifre A. Validation of tissue cross reactivity (TCR) studies: Tissue cross reactivity of anti-human C D209 in cynomolgus tissues. Toxicology Letters 2009; 189:5100-5.
31. Kallioniemi O-P, Wagner U, Kononen J, Sauter G. Tissue microarray technology for high-throughput molecular profiling of cancer. Human Molecular Genetics 2001; 10:657-62.
32. Lynch C, Grewel I. Preclinical safety evaluation of monoclonal antibodies. In: Chernajovsky Y, Nissim A, eds. Therapeutic Antibodies: Handbook of Experimental Pharmacology. Berlin: Springer-Verlag, 2008:19-44.
33. Dennis M S. CDR Repair: A novel approach to antibody humaization. In: Shire S J, Gombotz W, Bechtold-Peters K, Adndya J, eds. Current Trends in Monoclonal Antibody Development and Manufacturing. New York: Springer, 2010:9-28.
34. Gallop M A, Barrett R W, Dower W J, Fodor S P A, Gordon E M. Applications of combinatorial technologies to drug discovery. 1. Background and peptide combinatorial libraries. J Med Chem 1994; 37:1233-51.
35. Lee C V, Liang W—C, Dennis M S, Eigenbrot C, Sidhu S S, Fuh G. High-affinity human antibodies from phage-displayed synthetic Fab libraries with a single framework scaffold. J Mol Bio 2004; 340:1073-93.
36. Circolo A, Garnier G, Fukuda W, Wang X, Hidvegi T, Szalai A J, et al. Genetic disruption of the murine complement C3 promoter region generates deficient mice with extrahepatic expression of C3 mRNA. Immunopharmacology 1999; 42:135-49.
37. Chizzonite R, Truitt T, Podlaski F J, Wolitzky A G, Quinn P M, Nunes P, et al. I L-12:Monocloncal antibodies specific for the 40-kDa subunit block receptor binding and biological activity on activated human lymphoblasts. The Journal of Immunology 1991; 147:1548-56.
38. Jin Z, L1 Y, Pitti R, Lawrence D, Pham V C, Lill J R, et al. Cullin3-based polyubiquitination and p62-dependent aggregation of caspase-8 mediate extrinsic apoptosis signaling. Cell 2009; 137:721-35.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated antibody that binds to human FGFR4, wherein the antibody comprises (a) HVR-H1 comprising the amino acid sequence of SEQ ID NO:1; (b) HVR-H2 comprising the amino acid sequence of SEQ ID NO:2; (c) HVR-H3 comprising the amino acid sequence of SEQ ID NO:3; (d) HVR-L1 comprising the amino acid sequence of SEQ ID NO:4; (e) HVR-L2 comprising the amino acid sequence of SEQ ID NO:5; and (f) HVR-L3 comprising the amino acid sequence of SEQ ID NO:6.

2. The antibody of claim 1, further comprising a light chain variable domain framework sequence of SEQ ID NO: 9, 10, 11 and/or 12.

3. The antibody of claim 2, further comprising a heavy chain variable domain framework sequence of SEQ ID NO: 13, 14, 15 and/or 16.

4. An isolated antibody that binds to human FGFR4 comprising a VH sequence of SEQ ID NO:7 and a VL sequence of SEQ ID NO:8.

5. The antibody of claim 1 or 4, which is a full length IgG1 antibody.

6. A pharmaceutical formulation comprising the antibody of claim 1 or 4 and a pharmaceutically acceptable carrier.

7. A pharmaceutical formulation comprising the antibody of claim 1 and a pharmaceutically acceptable carrier.

8. A pharmaceutical formulation comprising the antibody of claim 4 and a pharmaceutically acceptable carrier.

\* \* \* \* \*

SEQUENCE LISTING

```
<160> NUMBER OF SEQ ID NOS: 39

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn His Trp Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Ile Leu Pro Val Asp Ser Glu Thr Thr Leu Glu Gln Lys Phe Lys
1               5                   10                  15

Asp
```

```
<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Asp Ile Ser Leu Phe Asp Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Thr Ser Gln Asp Ile Ser Asn Phe Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Thr Ser Arg Leu His Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Gly Asn Ala Leu Pro Tyr Thr
1               5

<210> SEQ ID NO 7
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn His
            20                  25                  30

Trp Met Asn Trp Val Arg Gln Ala Pro Gly Lys Gly Leu Glu Trp Val
        35                  40                  45

Gly Met Ile Leu Pro Val Asp Ser Glu Thr Thr Leu Glu Gln Lys Phe
    50                  55                  60
```

-continued

```
Lys Asp Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Thr Arg Gly Asp Ile Ser Leu Phe Asp Tyr Trp Gly Gln Gly Thr Leu
            100                 105                 110

Val Thr Val Ser Ser
        115

<210> SEQ ID NO 8
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
 1               5                  10                  15

Asp Arg Val Thr Ile Thr Cys Arg Thr Ser Gln Asp Ile Ser Asn Phe
             20                  25                  30

Leu Asn Trp Tyr Gln Gln Lys Pro Gly Lys Ala Phe Lys Ile Leu Ile
         35                  40                  45

Ser Tyr Thr Ser Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Ala Leu Pro Tyr
                 85                  90                  95

Thr Phe Gly Gln Gly Thr Lys Val Glu Ile Lys Arg
            100                 105

<210> SEQ ID NO 9
<211> LENGTH: 23
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
 1               5                  10                  15

Asp Arg Val Thr Ile Thr Cys
             20

<210> SEQ ID NO 10
<211> LENGTH: 15
<212> TYPE: PRT
<213> ORGANISM: Homo sapiens

<400> SEQUENCE: 10

Trp Tyr Gln Gln Lys Pro Gly Lys Ala Phe Lys Ile Leu Ile Ser
 1               5                  10                  15

<210> SEQ ID NO 11
<211> LENGTH: 32
<212> TYPE: PRT
<213> ORGANISM: Homo sapiens

<400> SEQUENCE: 11

Gly Val Pro Ser Arg Phe Ser Gly Ser Gly Ser Gly Thr Asp Phe Thr
```

```
                1               5                   10                  15
Leu Thr Ile Ser Ser Leu Gln Pro Glu Asp Phe Ala Thr Tyr Tyr Cys
                20                  25                  30

<210> SEQ ID NO 12
<211> LENGTH: 10
<212> TYPE: PRT
<213> ORGANISM: Homo sapiens

<400> SEQUENCE: 12

Phe Gly Gln Gly Thr Lys Val Glu Ile Lys
1               5                   10

<210> SEQ ID NO 13
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Val Arg Gln Ala Pro Gly Lys Gly Leu Glu Trp Val
1               5                   10

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Gly Gln Gly Thr Leu Val Thr Val Ser Ser
1               5                   10
```

```
<210> SEQ ID NO 17
<211> LENGTH: 39
<212> TYPE: PRT
<213> ORGANISM: Mus sp.

<400> SEQUENCE: 17

Asp Val Pro Ala Ala Asp Leu Ser Asp Gln Val Pro Asp Thr Asp Ser
1               5                   10                  15

Glu Thr Arg Ile Ile Leu Gln Gly Ser Pro Val Val Gln Met Ala Glu
            20                  25                  30

Asp Ala Val Asp Gly Glu Arg
        35

<210> SEQ ID NO 18
<211> LENGTH: 19
<212> TYPE: PRT
<213> ORGANISM: Mus sp.

<400> SEQUENCE: 18

Arg Gln Glu Ala Leu Glu Leu Ile Lys Lys Gly Tyr Thr Gln Gln Leu
1               5                   10                  15

Ala Phe Lys

<210> SEQ ID NO 19
<211> LENGTH: 18
<212> TYPE: PRT
<213> ORGANISM: Mus sp.

<400> SEQUENCE: 19

Ala Ala Phe Asn Asn Arg Pro Pro Ser Thr Trp Leu Thr Ala Tyr Val
1               5                   10                  15

Val Lys

<210> SEQ ID NO 20
<211> LENGTH: 17
<212> TYPE: PRT
<213> ORGANISM: Mus sp.

<400> SEQUENCE: 20

Ala Ala Asn Leu Ile Ala Ile Asp Ser His Val Leu Cys Gly Ala Val
1               5                   10                  15

Lys

<210> SEQ ID NO 21
<211> LENGTH: 23
<212> TYPE: PRT
<213> ORGANISM: Mus sp.

<400> SEQUENCE: 21

Gln Lys Pro Asp Gly Val Phe Gln Glu Asp Gly Pro Val Ile His Gln
1               5                   10                  15

Glu Met Ile Gly Gly Phe Arg
            20

<210> SEQ ID NO 22
<211> LENGTH: 64
<212> TYPE: PRT
<213> ORGANISM: Mus sp.

<400> SEQUENCE: 22

Glu Ala Asp Val Ser Leu Thr Ala Phe Val Leu Ile Ala Leu Gln Glu
1               5                   10                  15
```

Ala Arg Asp Ile Cys Glu Gly Gln Val Asn Ser Leu Pro Gly Ser Ile
            20                  25                  30

Asn Lys Ala Gly Glu Tyr Ile Glu Ala Ser Tyr Met Asn Leu Gln Arg
        35                  40                  45

Pro Tyr Thr Val Ala Ile Ala Gly Tyr Ala Leu Ala Leu Met Asn Lys
    50                  55                  60

<210> SEQ ID NO 23
<211> LENGTH: 16
<212> TYPE: PRT
<213> ORGANISM: Mus sp.

<400> SEQUENCE: 23

Trp Glu Glu Pro Asp Gln Gln Leu Tyr Asn Val Glu Ala Thr Ser Tyr
1               5                   10                  15

<210> SEQ ID NO 24
<211> LENGTH: 30
<212> TYPE: PRT
<213> ORGANISM: Mus sp.

<400> SEQUENCE: 24

Tyr Tyr Gly Gly Gly Tyr Gly Ser Thr Gln Ala Thr Phe Met Val Phe
1               5                   10                  15

Gln Ala Leu Ala Gln Tyr Gln Thr Asp Val Pro Asp His Lys
            20                  25                  30

<210> SEQ ID NO 25
<211> LENGTH: 12
<212> TYPE: PRT
<213> ORGANISM: Mus sp.

<400> SEQUENCE: 25

Gly Thr Leu Ser Val Ala Val Tyr His Ala Lys
1               5                   10

<210> SEQ ID NO 26
<211> LENGTH: 11
<212> TYPE: PRT
<213> ORGANISM: Mus sp.

<400> SEQUENCE: 26

Asp Leu Glu Leu Leu Ala Ser Gly Val Asp Arg
1               5                   10

<210> SEQ ID NO 27
<211> LENGTH: 9
<212> TYPE: PRT
<213> ORGANISM: Mus sp.

<400> SEQUENCE: 27

Asn Thr Leu Ile Ile Tyr Leu Glu Lys
1               5

<210> SEQ ID NO 28
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Trp Tyr Gln Gln Lys Pro Gly Lys Ala Pro Lys Leu Leu Ile Tyr
1               5                   10                  15

<210> SEQ ID NO 30
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Phe Gly Gln Gly Thr Lys Val Glu Ile Lys
1               5                   10

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Val Leu Leu Leu Leu Ala Gly Leu Tyr Arg Gly Lys Met Lys Ser
1               5                   10                  15

Gly

<210> SEQ ID NO 33
<211> LENGTH: 81
<212> TYPE: PRT
<213> ORGANISM: Homo sapiens

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
```

```
                    20                  25                  30

Pro Lys Leu Leu Ile Tyr Gly Val Pro Ser Arg Phe Ser Gly Ser Gly
            35                  40                  45

Ser Gly Thr Asp Phe Thr Leu Thr Ile Ser Ser Leu Gln Pro Glu Asp
        50                  55                  60

Phe Ala Thr Tyr Tyr Cys Phe Gly Gln Gly Thr Lys Val Glu Ile Lys
65                  70                  75                  80

Arg

<210> SEQ ID NO 34
<211> LENGTH: 108
<212> TYPE: PRT
<213> ORGANISM: Mus sp.

<400> SEQUENCE: 34

Asp Ile Gln Met Thr Gln Thr Thr Ser Ser Leu Ser Ala Ser Leu Gly
1               5                   10                  15

Asp Arg Val Thr Ile Thr Cys Arg Thr Ser Gln Asp Ile Ser Asn Phe
            20                  25                  30

Leu Asn Trp Tyr Gln Gln Lys Pro Asp Gly Thr Phe Lys Ile Leu Ile
        35                  40                  45

Ser Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Thr Leu Glu Gln
65                  70                  75                  80

Glu Asp Phe Ala Thr Tyr Phe Cys Gln Gln Gly Asn Ala Leu Pro Tyr
                85                  90                  95

Thr Phe Gly Gly Gly Thr Lys Leu Glu Ile Glu Arg
            100                 105

<210> SEQ ID NO 35
<211> LENGTH: 82
<212> TYPE: PRT
<213> ORGANISM: Homo sapiens

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Ala Asp Thr Ser Lys
        35                  40                  45

Asn Thr Ala Tyr Leu Gln Met Asn Ser Leu Arg Ala Glu Asp Thr Ala
    50                  55                  60

Val Tyr Tyr Cys Phe Asp Tyr Trp Gly Gln Gly Thr Leu Val Thr Val
65                  70                  75                  80

Ser Ser

<210> SEQ ID NO 36
<211> LENGTH: 117
<212> TYPE: PRT
<213> ORGANISM: Mus sp.

<400> SEQUENCE: 36

Glu Val Gln Leu Gln Gln Pro Gly Ala Val Leu Val Arg Pro Gly Thr
1               5                   10                  15

Ser Val Lys Leu Ser Cys Lys Ala Ser Gly Tyr Thr Phe Thr Asn His
```

```
                    20                  25                  30
Trp Met Asn Trp Val Lys Gln Arg Pro Gly Gln Gly Leu Glu Trp Ile
            35                  40                  45
Gly Met Ile His Pro Ser Asp Ser Glu Thr Thr Leu Asp Gln Lys Phe
        50                  55                  60
Lys Asp Lys Ala Thr Leu Thr Val Asp Lys Ser Ser Thr Ala Tyr
65                  70                  75                  80
Met Gln Leu Asn Arg Pro Thr Ser Glu Asp Ser Ala Val Tyr Tyr Cys
                85                  90                  95
Thr Arg Gly Asp Ile Ser Leu Phe Asp Tyr Trp Gly Gln Gly Thr Thr
            100                 105                 110
Val Thr Val Ser Ser
        115

<210> SEQ ID NO 37
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Leu Val Gln Pro Gly Gly
1               5                   10                  15
Ser Leu Arg Leu Ser Cys Ala Ala Ser Gly Tyr Thr Phe Thr Asn His
            20                  25                  30
Trp Met Asn Trp Val Arg Gln Ala Pro Gly Lys Gly Leu Glu Trp Val
        35                  40                  45
Gly Met Ile His Pro Ser Asp Ser Glu Thr Thr Leu Asp Gln Lys Phe
    50                  55                  60
Lys Asp Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Thr Arg Gly Asp Ile Ser Leu Phe Asp Tyr Trp Gly Gln Gly Thr Leu
            100                 105                 110
Val Thr Val Ser Ser
        115

<210> SEQ ID NO 38
<211> LENGTH: 1663
<212> TYPE: PRT
<213> ORGANISM: Mus sp.

<400> SEQUENCE: 38

Met Gly Pro Ala Ser Gly Ser Gln Leu Leu Val Leu Leu Leu Leu Leu
1               5                   10                  15
Ala Ser Ser Pro Leu Ala Leu Gly Ile Pro Met Tyr Ser Ile Ile Thr
            20                  25                  30
Pro Asn Val Leu Arg Leu Glu Ser Glu Glu Thr Ile Val Leu Glu Ala
        35                  40                  45
His Asp Ala Gln Gly Asp Ile Pro Val Thr Val Thr Val Gln Asp Phe
    50                  55                  60
Leu Lys Arg Gln Val Leu Thr Ser Glu Lys Thr Val Leu Thr Gly Ala
65                  70                  75                  80
Ser Gly His Leu Arg Ser Val Ser Ile Lys Ile Pro Ala Ser Lys Glu
```

```
                85                  90                  95
Phe Asn Ser Asp Lys Glu Gly His Lys Tyr Val Thr Val Ala Asn
            100                 105                 110
Phe Gly Glu Thr Val Val Glu Lys Ala Val Met Val Ser Phe Gln Ser
        115                 120                 125
Gly Tyr Leu Phe Ile Gln Thr Asp Lys Thr Ile Tyr Thr Pro Gly Ser
    130                 135                 140
Thr Val Leu Tyr Arg Ile Phe Thr Val Asp Asn Leu Leu Pro Val
145                 150                 155                 160
Gly Lys Thr Val Val Ile Leu Ile Glu Thr Pro Asp Gly Ile Pro Val
                165                 170                 175
Lys Arg Asp Ile Leu Ser Ser Asn Asn Gln His Gly Ile Leu Pro Leu
            180                 185                 190
Ser Trp Asn Ile Pro Glu Leu Val Asn Met Gly Gln Trp Lys Ile Arg
        195                 200                 205
Ala Phe Tyr Glu His Ala Pro Lys Gln Ile Phe Ser Ala Glu Phe Glu
    210                 215                 220
Val Lys Glu Tyr Val Leu Pro Ser Phe Glu Val Arg Val Glu Pro Thr
225                 230                 235                 240
Glu Thr Phe Tyr Tyr Ile Asp Asp Pro Asn Gly Leu Glu Val Ser Ile
                245                 250                 255
Ile Ala Lys Phe Leu Tyr Gly Lys Asn Val Asp Gly Thr Ala Phe Val
            260                 265                 270
Ile Phe Gly Val Gln Asp Gly Asp Lys Lys Ile Ser Leu Ala His Ser
        275                 280                 285
Leu Thr Arg Val Val Ile Glu Asp Gly Val Gly Asp Ala Val Leu Thr
    290                 295                 300
Arg Lys Val Leu Met Glu Gly Val Arg Pro Ser Asn Ala Asp Ala Leu
305                 310                 315                 320
Val Gly Lys Ser Leu Tyr Val Ser Val Thr Val Ile Leu His Ser Gly
                325                 330                 335
Ser Asp Met Val Glu Ala Glu Arg Ser Gly Ile Pro Ile Val Thr Ser
            340                 345                 350
Pro Tyr Gln Ile His Phe Thr Lys Thr Pro Lys Phe Phe Lys Pro Ala
        355                 360                 365
Met Pro Phe Asp Leu Met Val Phe Val Thr Asn Pro Asp Gly Ser Pro
    370                 375                 380
Ala Ser Lys Val Leu Val Val Thr Gln Gly Ser Asn Ala Lys Ala Leu
385                 390                 395                 400
Thr Gln Asp Asp Gly Val Ala Lys Leu Ser Ile Asn Thr Pro Asn Ser
                405                 410                 415
Arg Gln Pro Leu Thr Ile Thr Val Arg Thr Lys Lys Asp Thr Leu Pro
            420                 425                 430
Glu Ser Arg Gln Ala Thr Lys Thr Met Glu Ala His Pro Tyr Ser Thr
        435                 440                 445
Met His Asn Ser Asn Asn Tyr Leu His Leu Ser Val Ser Arg Met Glu
    450                 455                 460
Leu Lys Pro Gly Asp Asn Leu Asn Val Asn Phe His Leu Arg Thr Asp
465                 470                 475                 480
Pro Gly His Glu Ala Lys Ile Arg Tyr Tyr Thr Tyr Leu Val Met Asn
                485                 490                 495
Lys Gly Lys Leu Leu Lys Ala Gly Arg Gln Val Arg Glu Pro Gly Gln
            500                 505                 510
```

```
Asp Leu Val Val Leu Ser Leu Pro Ile Thr Pro Glu Phe Ile Pro Ser
            515                 520                 525

Phe Arg Leu Val Ala Tyr Tyr Thr Leu Ile Gly Ala Ser Gly Gln Arg
    530                 535                 540

Glu Val Val Ala Asp Ser Val Trp Val Asp Val Lys Asp Ser Cys Ile
545                 550                 555                 560

Gly Thr Leu Val Val Lys Gly Asp Pro Arg Asp Asn His Leu Ala Pro
                565                 570                 575

Gly Gln Gln Thr Thr Leu Arg Ile Glu Gly Asn Gln Gly Ala Arg Val
            580                 585                 590

Gly Leu Val Ala Val Asp Lys Gly Val Phe Val Leu Asn Lys Lys Asn
        595                 600                 605

Lys Leu Thr Gln Ser Lys Ile Trp Asp Val Val Glu Lys Ala Asp Ile
            610                 615                 620

Gly Cys Thr Pro Gly Ser Gly Lys Asn Tyr Ala Gly Val Phe Met Asp
625                 630                 635                 640

Ala Gly Leu Ala Phe Lys Thr Ser Gln Gly Leu Gln Thr Glu Gln Arg
                645                 650                 655

Ala Asp Leu Glu Cys Thr Lys Pro Ala Ala Arg Arg Arg Arg Ser Val
            660                 665                 670

Gln Leu Met Glu Arg Arg Met Asp Lys Ala Gly Gln Tyr Thr Asp Lys
        675                 680                 685

Gly Leu Arg Lys Cys Cys Glu Asp Gly Met Arg Asp Ile Pro Met Arg
    690                 695                 700

Tyr Ser Cys Gln Arg Arg Ala Arg Leu Ile Thr Gln Gly Glu Asn Cys
705                 710                 715                 720

Ile Lys Ala Phe Ile Asp Cys Cys Asn His Ile Thr Lys Leu Arg Glu
                725                 730                 735

Gln His Arg Arg Asp His Val Leu Gly Leu Ala Arg Ser Glu Leu Glu
            740                 745                 750

Glu Asp Ile Ile Pro Glu Glu Asp Ile Ile Ser Arg Ser His Phe Pro
        755                 760                 765

Gln Ser Trp Leu Trp Thr Ile Glu Glu Leu Lys Glu Pro Glu Lys Asn
    770                 775                 780

Gly Ile Ser Thr Lys Val Met Asn Ile Phe Leu Lys Asp Ser Ile Thr
785                 790                 795                 800

Thr Trp Glu Ile Leu Ala Val Ser Leu Ser Asp Lys Lys Gly Ile Cys
                805                 810                 815

Val Ala Asp Pro Tyr Glu Ile Arg Val Met Gln Asp Phe Phe Ile Asp
            820                 825                 830

Leu Arg Leu Pro Tyr Ser Val Val Arg Asn Glu Gln Val Glu Ile Arg
        835                 840                 845

Ala Val Leu Phe Asn Tyr Arg Glu Gln Glu Glu Leu Lys Val Arg Val
    850                 855                 860

Glu Leu Leu His Asn Pro Ala Phe Cys Ser Met Ala Thr Ala Lys Asn
865                 870                 875                 880

Arg Tyr Phe Gln Thr Ile Lys Ile Pro Pro Lys Ser Ser Val Ala Val
                885                 890                 895

Pro Tyr Val Ile Val Pro Leu Lys Ile Gly Gln Gln Glu Val Glu Val
            900                 905                 910

Lys Ala Ala Val Phe Asn His Phe Ile Ser Asp Gly Val Lys Lys Thr
        915                 920                 925
```

-continued

```
Leu Lys Val Val Pro Glu Gly Met Arg Ile Asn Lys Thr Val Ala Ile
930                 935                 940

His Thr Leu Asp Pro Glu Lys Leu Gly Gln Gly Gly Val Gln Lys Val
945                 950                 955                 960

Asp Val Pro Ala Ala Asp Leu Ser Asp Gln Val Pro Asp Thr Asp Ser
            965                 970                 975

Glu Thr Arg Ile Ile Leu Gln Gly Ser Pro Val Val Gln Met Ala Glu
            980                 985                 990

Asp Ala Val Asp Gly Glu Arg Leu Lys His Leu Ile Val Thr Pro Ala
        995                 1000                1005

Gly Cys Gly Glu Gln Asn Met Ile Gly Met Thr Pro Thr Val Ile
    1010                1015                1020

Ala Val His Tyr Leu Asp Gln Thr Glu Gln Trp Glu Lys Phe Gly
    1025                1030                1035

Ile Glu Lys Arg Gln Glu Ala Leu Glu Leu Ile Lys Lys Gly Tyr
    1040                1045                1050

Thr Gln Gln Leu Ala Phe Lys Gln Pro Ser Ser Ala Tyr Ala Ala
    1055                1060                1065

Phe Asn Asn Arg Pro Pro Ser Thr Trp Leu Thr Ala Tyr Val Val
    1070                1075                1080

Lys Val Phe Ser Leu Ala Ala Asn Leu Ile Ala Ile Asp Ser His
    1085                1090                1095

Val Leu Cys Gly Ala Val Lys Trp Leu Ile Leu Glu Lys Gln Lys
    1100                1105                1110

Pro Asp Gly Val Phe Gln Glu Asp Gly Pro Val Ile His Gln Glu
    1115                1120                1125

Met Ile Gly Gly Phe Arg Asn Ala Lys Glu Ala Asp Val Ser Leu
    1130                1135                1140

Thr Ala Phe Val Leu Ile Ala Leu Gln Glu Ala Arg Asp Ile Cys
    1145                1150                1155

Glu Gly Gln Val Asn Ser Leu Pro Gly Ser Ile Asn Lys Ala Gly
    1160                1165                1170

Glu Tyr Ile Glu Ala Ser Tyr Met Asn Leu Gln Arg Pro Tyr Thr
    1175                1180                1185

Val Ala Ile Ala Gly Tyr Ala Leu Ala Leu Met Asn Lys Leu Glu
    1190                1195                1200

Glu Pro Tyr Leu Gly Lys Phe Leu Asn Thr Ala Lys Asp Arg Asn
    1205                1210                1215

Arg Trp Glu Glu Pro Asp Gln Gln Leu Tyr Asn Val Glu Ala Thr
    1220                1225                1230

Ser Tyr Ala Leu Leu Ala Leu Leu Leu Lys Asp Phe Asp Ser
    1235                1240                1245

Val Pro Pro Val Val Arg Trp Leu Asn Glu Gln Arg Tyr Tyr Gly
    1250                1255                1260

Gly Gly Tyr Gly Ser Thr Gln Ala Thr Phe Met Val Phe Gln Ala
    1265                1270                1275

Leu Ala Gln Tyr Gln Thr Asp Val Pro Asp His Lys Asp Leu Asn
    1280                1285                1290

Met Asp Val Ser Phe His Leu Pro Ser Arg Ser Ser Ala Thr Thr
    1295                1300                1305

Phe Arg Leu Leu Trp Glu Asn Gly Asn Leu Leu Arg Ser Glu Glu
    1310                1315                1320

Thr Lys Gln Asn Glu Ala Phe Ser Leu Thr Ala Lys Gly Lys Gly
```

```
                    1325                1330                1335

Arg Gly Thr Leu Ser Val Val Ala Val Tyr His Ala Lys Leu Lys
        1340                1345                1350

Ser Lys Val Thr Cys Lys Lys Phe Asp Leu Arg Val Ser Ile Arg
        1355                1360                1365

Pro Ala Pro Glu Thr Ala Lys Lys Pro Glu Glu Ala Lys Asn Thr
        1370                1375                1380

Met Phe Leu Glu Ile Cys Thr Lys Tyr Leu Gly Asp Val Asp Ala
        1385                1390                1395

Thr Met Ser Ile Leu Asp Ile Ser Met Met Thr Gly Phe Ala Pro
        1400                1405                1410

Asp Thr Lys Asp Leu Glu Leu Leu Ala Ser Gly Val Asp Arg Tyr
        1415                1420                1425

Ile Ser Lys Tyr Glu Met Asn Lys Ala Phe Ser Asn Lys Asn Thr
        1430                1435                1440

Leu Ile Ile Tyr Leu Glu Lys Ile Ser His Thr Glu Glu Asp Cys
        1445                1450                1455

Leu Thr Phe Lys Val His Gln Tyr Phe Asn Val Gly Leu Ile Gln
        1460                1465                1470

Pro Gly Ser Val Lys Val Tyr Ser Tyr Asn Leu Glu Glu Ser
        1475                1480                1485

Cys Thr Arg Phe Tyr His Pro Glu Lys Asp Asp Gly Met Leu Ser
        1490                1495                1500

Lys Leu Cys His Ser Glu Met Cys Arg Cys Ala Glu Glu Asn Cys
        1505                1510                1515

Phe Met Gln Gln Ser Gln Glu Lys Ile Asn Leu Asn Val Arg Leu
        1520                1525                1530

Asp Lys Ala Cys Glu Pro Gly Val Asp Tyr Val Tyr Lys Thr Glu
        1535                1540                1545

Leu Thr Asn Ile Lys Leu Leu Asp Asp Phe Asp Glu Tyr Thr Met
        1550                1555                1560

Thr Ile Gln Gln Val Ile Lys Ser Gly Ser Asp Glu Val Gln Ala
        1565                1570                1575

Gly Gln Gln Arg Lys Phe Ile Ser His Ile Lys Cys Arg Asn Ala
        1580                1585                1590

Leu Lys Leu Gln Lys Gly Lys Lys Tyr Leu Met Trp Gly Leu Ser
        1595                1600                1605

Ser Asp Leu Trp Gly Glu Lys Pro Asn Thr Ser Tyr Ile Ile Gly
        1610                1615                1620

Lys Asp Thr Trp Val Glu His Trp Pro Glu Ala Glu Glu Cys Gln
        1625                1630                1635

Asp Gln Lys Tyr Gln Lys Gln Cys Glu Glu Leu Gly Ala Phe Thr
        1640                1645                1650

Glu Ser Met Val Val Tyr Gly Cys Pro Asn
        1655                1660

<210> SEQ ID NO 39
<211> LENGTH: 805
<212> TYPE: PRT
<213> ORGANISM: Homo sapiens

<400> SEQUENCE: 39

Met Arg Leu Leu Leu Ala Leu Leu Gly Val Leu Leu Ser Val Pro Gly
1               5                   10                  15
```

-continued

```
Pro Pro Val Leu Ser Leu Glu Ala Ser Glu Val Glu Leu Glu Pro
         20                  25                  30

Cys Leu Ala Pro Ser Leu Glu Gln Gln Glu Gln Glu Leu Thr Val Ala
         35                  40                      45

Leu Gly Gln Pro Val Arg Leu Cys Cys Gly Arg Ala Glu Arg Gly Gly
         50                  55                      60

His Trp Tyr Lys Glu Gly Ser Arg Leu Ala Pro Ala Gly Arg Val Arg
65                      70                  75                  80

Gly Trp Arg Gly Arg Leu Glu Ile Ala Ser Phe Leu Pro Glu Asp Ala
                     85                  90                  95

Gly Arg Tyr Leu Cys Leu Ala Arg Gly Ser Met Ile Val Leu Gln Asn
             100                 105                 110

Leu Thr Leu Ile Thr Gly Asp Ser Leu Thr Ser Ser Asn Asp Asp Glu
         115                 120                 125

Asp Pro Lys Ser His Arg Asp Pro Ser Asn Arg His Ser Tyr Pro Gln
         130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                 165                 170                 175

Asn Pro Thr Pro Thr Ile Arg Trp Leu Lys Asp Gly Gln Ala Phe His
             180                 185                 190

Gly Glu Asn Arg Ile Gly Gly Ile Arg Leu Arg His Gln His Trp Ser
         195                 200                 205

Leu Val Met Glu Ser Val Val Pro Ser Asp Arg Gly Thr Tyr Thr Cys
         210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                 245                 250                 255

Ala Asn Thr Thr Ala Val Val Gly Ser Asp Val Glu Leu Leu Cys Lys
             260                 265                 270

Val Tyr Ser Asp Ala Gln Pro His Ile Gln Trp Leu Lys His Ile Val
         275                 280                 285

Ile Asn Gly Ser Ser Phe Gly Ala Asp Gly Phe Pro Tyr Val Gln Val
         290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                 325                 330                 335

Asn Ser Ile Gly Leu Ser Tyr Gln Ser Ala Trp Leu Thr Val Leu Pro
             340                 345                 350

Glu Glu Asp Pro Thr Trp Thr Ala Ala Ala Pro Glu Ala Arg Tyr Thr
         355                 360                 365

Asp Ile Ile Leu Tyr Ala Ser Gly Ser Leu Ala Leu Ala Val Leu Leu
         370                 375                 380

Leu Leu Ala Gly Leu Tyr Arg Gly Gln Ala Leu His Gly Arg His Pro
385                 390                 395                 400

Arg Pro Pro Ala Thr Val Gln Lys Leu Ser Arg Phe Pro Leu Ala Arg
                 405                 410                 415

Gln Phe Ser Leu Glu Ser Gly Ser Gly Lys Ser Ser Ser Ser Leu
             420                 425                 430

Val Arg Gly Val Arg Leu Ser Ser Ser Gly Pro Ala Leu Leu Ala Gly
```

```
                    435                 440                 445
Leu Val Ser Leu Asp Leu Pro Leu Asp Pro Leu Trp Glu Phe Pro Arg
            450                 455                 460
Asp Arg Leu Val Leu Gly Lys Pro Leu Gly Glu Gly Cys Phe Gly Gln
465                 470                 475                 480
Val Val Arg Ala Glu Ala Phe Gly Met Asp Pro Ala Arg Pro Asp Gln
                    485                 490                 495
Ala Ser Thr Val Ala Val Lys Met Leu Lys Asp Asn Ala Ser Asp Lys
            500                 505                 510
Asp Leu Ala Asp Leu Val Ser Glu Met Glu Val Met Lys Leu Ile Gly
            515                 520                 525
Arg His Lys Asn Ile Ile Asn Leu Leu Gly Val Cys Thr Gln Glu Gly
        530                 535                 540
Pro Leu Tyr Val Ile Val Glu Cys Ala Ala Lys Gly Asn Leu Arg Glu
545                 550                 555                 560
Phe Leu Arg Ala Arg Arg Pro Pro Gly Pro Asp Leu Ser Pro Asp Gly
                565                 570                 575
Pro Arg Ser Ser Glu Gly Pro Leu Ser Phe Pro Val Leu Val Ser Cys
                580                 585                 590
Ala Tyr Gln Val Ala Arg Gly Met Gln Tyr Leu Glu Ser Arg Lys Cys
            595                 600                 605
Ile His Arg Asp Leu Ala Ala Arg Asn Val Leu Val Thr Glu Asp Asn
        610                 615                 620
Val Met Lys Ile Ala Asp Phe Gly Leu Ala Arg Gly Val His His Ile
625                 630                 635                 640
Asp Tyr Tyr Lys Lys Thr Ser Asn Gly Arg Leu Pro Val Lys Trp Met
                645                 650                 655
Ala Pro Glu Ala Leu Phe Asp Arg Val Tyr Thr His Gln Ser Asp Val
                660                 665                 670
Trp Ser Phe Gly Ile Leu Leu Trp Glu Ile Phe Thr Leu Gly Gly Ser
            675                 680                 685
Pro Tyr Pro Gly Ile Pro Val Glu Glu Leu Phe Ser Leu Leu Arg Glu
        690                 695                 700
Gly His Arg Met Asp Arg Pro Pro His Cys Pro Pro Glu Leu Tyr Gly
705                 710                 715                 720
Leu Met Arg Glu Cys Trp His Ala Ala Pro Ser Gln Arg Pro Thr Phe
                725                 730                 735
Lys Gln Leu Val Glu Ala Leu Asp Lys Val Leu Leu Ala Val Ser Glu
                740                 745                 750
Glu Tyr Leu Asp Leu Arg Leu Thr Phe Gly Pro Tyr Ser Pro Ser Gly
            755                 760                 765
Gly Asp Ala Ser Ser Thr Cys Ser Ser Ser Asp Ser Val Phe Ser His
        770                 775                 780
Asp Pro Leu Pro Leu Gly Ser Ser Ser Phe Pro Phe Gly Ser Gly Val
785                 790                 795                 800
Gln Thr Glu Phe Thr
                805
```